United States Patent
Tufaro et al.

(10) Patent No.: US 11,090,344 B2
(45) Date of Patent: Aug. 17, 2021

(54) ADENOVIRUS AND IMMUNOMODULATOR COMBINATION THERAPY

(71) Applicants: DNATRIX, INC., Houston, TX (US); BOARD OF REGENTS, THE UNIVERSITY OF TEXAS SYSTEM, Austin, TX (US)

(72) Inventors: Frank Tufaro, Rancho Santa Fe, CA (US); Juan Fueyo-Margareto, Houston, TX (US); Candelaria Gomez-Manzano, Houston, TX (US); Charles Conrad, Spring, TX (US); W. K. Alfred Yung, Houston, TX (US); Hong Jiang, Houston, TX (US)

(73) Assignees: DNATRIX, INC., Houston, TX (US); BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 119 days.

(21) Appl. No.: 16/304,359

(22) PCT Filed: May 30, 2017

(86) PCT No.: PCT/US2017/035041
§ 371 (c)(1),
(2) Date: Nov. 26, 2018

(87) PCT Pub. No.: WO2017/205875
PCT Pub. Date: Nov. 30, 2017

(65) Prior Publication Data
US 2019/0201462 A1    Jul. 4, 2019

Related U.S. Application Data

(60) Provisional application No. 62/342,482, filed on May 27, 2016.

(51) Int. Cl.
| | |
|---|---|
| A61K 35/761 | (2015.01) |
| C07K 16/28 | (2006.01) |
| C12N 15/86 | (2006.01) |
| A61K 9/00 | (2006.01) |
| A61K 39/395 | (2006.01) |
| A61P 35/04 | (2006.01) |

(52) U.S. Cl.
CPC .......... *A61K 35/761* (2013.01); *A61K 9/0019* (2013.01); *C07K 16/28* (2013.01); *C12N 15/86* (2013.01); *A61K 39/39541* (2013.01); *A61P 35/04* (2018.01); *C07K 16/2827* (2013.01); *C12N 2710/10332* (2013.01); *C12N 2710/10343* (2013.01)

(58) Field of Classification Search
None
See application file for complete search history.

(56) References Cited

U.S. PATENT DOCUMENTS

| | | | |
|---|---|---|---|
| 8,217,149 B2 | 7/2012 | Irving et al. | |
| 8,354,509 B2 | 1/2013 | Carven et al. | |
| 8,563,694 B2 | 10/2013 | Mataraza et al. | |
| 8,779,108 B2 | 7/2014 | Queva et al. | |
| 8,841,418 B2 | 9/2014 | Karsunky et al. | |
| 2002/0039581 A1 | 4/2002 | Carreno et al. | |
| 2002/0086014 A1 | 7/2002 | Korman et al. | |
| 2003/0138405 A1 | 7/2003 | Fueyo et al. | |
| 2005/0201994 A1 | 9/2005 | Korman et al. | |
| 2006/0147420 A1 | 7/2006 | Fueyo et al. | |
| 2010/0233183 A1 | 9/2010 | Triebel et al. | |
| 2011/0150892 A1 | 6/2011 | Thudium et al. | |
| 2012/0294796 A1 | 11/2012 | Johnson et al. | |
| 2014/0294861 A1 | 10/2014 | Scholler et al. | |
| 2014/0377221 A1 | 12/2014 | Tufaro et al. | |
| 2015/0368349 A1 | 12/2015 | Gonzalez et al. | |

FOREIGN PATENT DOCUMENTS

| | | | | |
|---|---|---|---|---|
| EP | 3293201 A1 | 3/1918 | | |
| WO | WO-2013112942 A1 * | 8/2013 | .............. | A61P 15/00 |
| WO | WO2013116778 A2 | 8/2013 | | |
| WO | WO 2015/077624 | 5/2015 | | |
| WO | WO-2015077624 A1 * | 5/2015 | .............. | A61P 35/00 |

OTHER PUBLICATIONS

Burke, J., Cytokine & Growth Factor Reviews, vol. 21, Issues 2-3, pp. 99-102 (Year: 2010).*
International Search Report and Written Opinion issued in International Application No. PCT/US17/35041, dated Aug. 15, 2017.
Jiang, et al. "Oncolytic adenovirus: preclinical and clinical studies in patients with human malignant gliomas." *Current gene therapy* 9.5 (2009): 422-427.
Jones, et al. "Tim-3 expression defines a novel population of dysfunctional T cells with highly elevated frequencies in progressive HIV-1 infection," *Journal of Experimental Medicine* 205.12 (2008): 2763-2779.
Romagné, et al. "Preclinical characterization of 1-7F9, a novel human anti-KIR receptor therapeutic antibody that augments natural killer-mediated killing of tumor cells." *Blood* 114.13 (2009): 2667-2677.
Andarini, S, et al.; "Adenovirus vector-mediated in vivo gene transfer of OX40 ligand to tumor cells enhances antitumor immunity of tumor-bearing hosts."; *Cancer Res.* May 1, 2004;64(9):3281-7.
Jiang, H. et al.; "Localized Treatment with Oncolytic Adenovirus Delta-24-RGDOX Induces Systemic Immunity against Disseminated Subcutaneous and Intracranial Melanomas." *Clin Cancer Res.* Nov. 15, 2019;25(22):6801-6814. doi: 10.1158/1078-0432.CCR-19/0405. Epub Aug. 27, 2019.
Rivera-Molina, Y, e al.;"GITRL-armed Delta-24-RGD oncolytic adenovirus prolongs survival and induces anti-glioma immune memory." *Neurooncol Adv.* May-Dec. 2019;1(1):vdz009. doi: 10.1093/noajnl/vdz009. Epub Jun. 5, 2019.

(Continued)

*Primary Examiner* — Shanon A. Foley
*Assistant Examiner* — Myron G Hill
(74) *Attorney, Agent, or Firm* — Parker Highlander PLLC

(57) ABSTRACT

Certain embodiments include the enhancement of effectiveness for an adenoviral cancer therapy.

14 Claims, 16 Drawing Sheets

Specification includes a Sequence Listing.

(56) References Cited

OTHER PUBLICATIONS

Sanmamed, MF, et al.; "Agonists of Co-stimulation in Cancer Immunotherapy Directed Against CD137, OX40, GITR, CD27, CD28, and ICOS." *Semin Oncol.* Aug. 2015;42(4):640-55. doi: 10.1053/j.seminoncol.2015.05.014. Epub Jun. 11, 2015.
Supplemental European Search Report issued in EP17803756 dated Jan. 23, 2020.

\* cited by examiner

Immunocompetent model (C57BL/6 mouse)

Immunodeficient model (athymic mouse)

SEQUENCE LISTING

```
<160> NUMBER OF SEQ ID NOS: 3

<210> SEQ ID NO 1
<211> LENGTH: 8
<212> TYPE: PRT
<213> ORGANISM: Artificial Sequence
<220> FEATURE:
<223> OTHER INFORMATION: Synthetic Immunogenic EGFRvIII peptide

<400> SEQUENCE: 1

Glu Lys Lys Gly Asn Tyr Val Val
1               5

<210> SEQ ID NO 2
<211> LENGTH: 11
<212> TYPE: PRT
<213> ORGANISM: Artificial Sequence
<220> FEATURE:
<223> OTHER INFORMATION: Synthetic Immunogenic EGFRvIII peptide

<400> SEQUENCE: 2

Leu Glu Glu Lys Lys Gly Asn Tyr Val Val Thr
1               5                   10

<210> SEQ ID NO 3
<211> LENGTH: 14
<212> TYPE: PRT
<213> ORGANISM: Artificial Sequence
<220> FEATURE:
<223> OTHER INFORMATION: Synthetic Immunogenic NY-ESO-1 peptide

<400> SEQUENCE: 3

Ser Leu Leu Met Trp Ile Thr Gln Cys Phe Leu Pro Val Phe
1               5                   10
```

ADENOVIRUS AND IMMUNOMODULATOR COMBINATION THERAPY

CROSS-REFERENCE TO RELATED APPLICATIONS

This application is a national phase application under 35 U.S.C. § 371 of International Application No. PCT/US2017/035041, filed May 30, 2017, which claims the benefit of U.S. Provisional Patent Application Ser. No. 62/342,482, filed May 27, 2016, the full disclosure of each of which is incorporated herein by reference.

INCORPORATION BV REFERENCE OF A SEQUENCE LISTING PROVIDED AS A TEXT FILE

A Sequence Listing is provided herewith as a text file, "011863-5006WO-DNAtrix_ST25.txt" created on May 30, 2017 and having a size of 2 KB. The contents of the text file are incorporated by reference herein in its entirety.

BACKGROUND

Field of Invention

The present invention relates generally to the fields of oncology and cancer therapy. More particularly, it concerns replicative oncolytic viruses genetically modified to express an antagonist of an inhibitory signal of an immune cell such as a PD-1 or PD-L1 inhibitor and/or an immune cell stimulatory receptor agonist and pharmaceutical combinations comprising (i) a replicative oncolytic virus genetically modified to express an antagonist of an inhibitory signal of an immune cell and/or an immune cell co-stimulatory receptor agonist and (ii) a separately administered immune cell stimulatory receptor agonist and/or immune checkpoint inhibitor for use in treating cancer.

Background

Cancer remains one of the leading causes of morbidity and mortality in humans worldwide. Although surgery, chemotherapy and radiation have been utilized with some success to cure cancer, novel strategies are needed. Viruses that replicate in tumor cells better than in normal cells have shown promise as oncolytic agents. The feasibility of gene transfer and tumor lysis using adenoviruses has been well established.

There remains a need for additional anti-cancer therapeutics.

SUMMARY

The present invention relates to novel replication-competent oncolytic viruses expressing one or more antagonists of an inhibitory signal of an immune cell, pharmaceutical composition comprising the replication competent oncolytic virus and their use in treating a variety of cancers. The present invention also relates to a pharmaceutical combination comprising (i) a replication-competent oncolytic virus expressing one or more antagonists of an inhibitory signal of an immune cell and/or one or more immune cell stimulatory receptor agonists and (ii) an immune cell stimulatory receptor agonist and/or antagonist of an inhibitory signal of an immune cell. In preferred embodiments, a pharmaceutical combination is provided comprising (i) a replication-competent adenovirus expressing an immune cell stimulatory receptor agonist such as OX40L and/or GITL and (ii) an immune checkpoint inhibitor, wherein the adenovirus and immune checkpoint inhibitor are for separate, sequential or simultaneous administration. The replication-competent oncolytic virus will present the immune cell stimulatory receptor agonist and/or antagonist of an inhibitory signal of an immune cell from the first replication cycle, triggering a persistent effector anti-tumor immune response by activating lymphocytes that recognize tumor antigens and reversing the immune suppressive environment surrounding the tumor. In certain aspects, administration of the engineered replication-competent oncolytic virus to a subject with cancer provides an enhanced and even synergistic anti-tumor immunity compared to the unmodified virus (i.e. not expressing an immune cell stimulatory receptor agonist or antagonist of an inhibitory signal of an immune cell) and the immune cell stimulatory receptor agonist and/or antagonist of an inhibitory signal of an immune cell when administered separately. In related aspects, the anti-tumor effects of the replication-competent oncolytic virus persist even after clearance of the virus and even extend to one or more non-infected tumors.

In several embodiments, the replication-competent oncolytic virus is engineered to express an antagonist of an inhibitory signal of an immune cell. The antagonist of an inhibitory signal of an immune cell is preferably an inhibitor of an immune checkpoint protein such as, without limitation, cytotoxic T-lymphocyte antigen-4 (CTLA4), programmed cell death protein 1 (PD-1), B7-H3, B7-H4, T cell membrane protein 3 (TIM), galectin 9 (GAL9), lymphocyte activation gene 3 (LAGS), V-domain immunoglobulin (Ig)-containing suppressor of T-cell activation (VISTA), Killer-Cell Immunoglobulin-Like Receptor (KIR), B and T lymphocyte attenuator (BTLA), or T cell immunoreceptor with Ig and ITIM domains (TIGIT). The oncolytic virus may be engineered to express an inhibitor of a ligand of an immune checkpoint protein including without limitation a ligand of CTLA4, PD-1, B7-113, B7-H4, TIM3, GAL9, LAGS, VISTA, KIR, or BTLA.

In certain preferred embodiments, a replication-competent oncolytic virus (e.g. adenovirus) is provided that expresses an antagonist of PD-1 and/or an antagonist of either of its ligands PD-L1 and PD-L2. PD-L1 has been identified as a negative regulator of antitumor T cells and is expressed in up to 50% of human cancer. Binding of PD-L1 on tumor cells to PD-1 on activated effector T cells results in activation of PI3 kinase-signaling cascade which in turn blocks the production of cytotoxic mediators required for killing tumor cells. As used herein, a PD-L1, PD-L2 or PD-1 antagonist is a molecule that disrupts the interaction between PD-1 and either or both of its ligands PD-L1 and PD-L2. In one aspect, the replication-competent oncolytic virus is an adenovirus that comprises heterologous nucleic acid encoding a PD-L1, PD-L2 and/or PD-1 antagonist inserted into a non-essential region of the adenovirus genome. In related aspects, the heterologous nucleic acid encodes an anti-PD-L1 monoclonal antibody such as BMS-936559 (MDX-1105), atezolizumab (Tecentriq; MPDL3280A) disclosed in U.S. Pat. No. 8,217,149, durvalumab (MEDI4736) disclosed in U.S. Pat. No. 8,779,108, the contents of which are incorporated herein by reference, MIH1 (Affymetrix, obtainable via eBioscience (16.5983.82) or avelumab (MSB0010718C; Merck KgaA), or an anti-PD-1 monoclonal antibody such as nivolumab (BMS-936558), pembrolizumab or lambrolizumab. In other embodiments, the heterologous nucleic acid encodes a PD-L1 or PD-1 antagonist such as those described in US Patent Application Publication Nos. 2009/0217401, 20110195068 and 20120251537 and U.S. Pat. No. 8,217,149, the contents of each which are incorporated herein by reference. In a preferred embodiment, the replication-competent oncolytic virus is an adenovirus expressing a PD-L1 and/or PD-1 antagonist. In one preferred embodiment, the adenovirus is Delta-24 or Delta-24-RGD adenovirus.

In other preferred embodiments, a replication-competent oncolytic virus (e.g. adenovirus) is provided that expresses an antagonist of CTLA4. In one aspect, the replication-competent oncolytic virus is an adenovirus that comprises heterologous nucleic acid encoding a CTLA4 antagonist inserted into a non-essential region of the adenovirus genome. In related aspects, the heterologous nucleic acid encodes an anti-CTLA4 monoclonal antibody such as ipilimumab or tremelimumab.

In related embodiments, a replication-competent oncolytic virus (e.g. adenovirus) is provided that is engineered to express an antagonist of an inhibitory signal of an immune cell and also to express an agonist of an immune cell stimulatory receptor. In certain embodiments, the replication competent oncolytic virus expresses an antagonist of an inhibitory signal of an immune cell and also expresses an agonist of an immune cell stimulatory receptor selected from the group consisting of CD28, OX40 (CD134), glucocorticoid-induced TNF-receptor (GITR), CD137 (4-1BB), herpes virus entry mediator A (HVEM), inducible T-cell costimulator (ICOS or CD278), CD27, CD40, CD226, cytotoxic and regulatory T cell molecule (CRTAM), death receptor 3 (DR3), lymphotoxin-beta receptor (LTBR), transmembrane activator and CAML interactor (TACI), B cell-activating factor receptor (BAFFR) and B cell maturation protein (BCMA). In a preferred embodiment, a replication competent adenovirus expressing (i) a GITR polypeptide ligand and/or an OX40 polypeptide ligand and (ii) a PD-1, PD-L1, PD-L2 and/or CTLA4 inhibitor is provided. In some embodiments, the replication competent oncolytic virus expresses a PD-L1 or PD-1 antagonist in addition to expressing an immune cell stimulatory agonist such as GITR polypeptide ligand and/or OX40 polypeptide ligand.

In certain embodiments, the replication-competent oncolytic virus, in addition to expressing an immune checkpoint inhibitor and optionally an immune cell stimulatory receptor agonist, also expresses one or more tumor antigens. In preferred embodiments, the one or more tumor antigens are expressed on the surface of the virus, in which case insertion of nucleic acid(s) encoding the tumor antigen(s) into the virus genome should be done "in frame". In certain aspects, 1, 2, 3, 4, or 5 antigens are expressed on the surface of the virus, for example, by inserting nucleic acid encoding each antigen into a separate gene encoding an adenovirus surface protein. In a preferred embodiment, the tumor associated antigen(s) are EGFRvIII (epidermal growth factor receptor variant III) and/or NY-ESO-1 (New York oesophageal squamas cell carcinoma 1). The tumor antigens can be expressed as part of the capsid or fiber, or produced as exogenous proteins linked to autophagy-related proteins such as LC3 to increase the presentation of the exogenous protein during the adenoviral infection and replication. Targeting multiple antigens will help generate a consistent and effective immune response.

In certain aspects, the replication-competent oncolytic virus expresses an immune cell stimulatory receptor agonist and/or expresses an antagonist of an inhibitory signal of an immune cell from heterologous nucleic acid incorporated into a non-essential region of the viral genome, the heterologous nucleic acid comprising a nucleic acid sequence encoding the immune cell stimulatory receptor agonist or antagonist of an inhibitory signal of an immune cell under the control of a sequence permitting expression of the antagonist of an inhibitory signal of an immune cell or immune cell stimulatory receptor agonist in a cell. In some embodiments, the replication-competent oncolytic virus is an adenovirus and expression of the immune cell stimulatory receptor agonist and/or antagonist of an inhibitory signal of an immune cell is under the control of an endogenous adenovirus promoter such as the E3 promoter or a late adenoviral promoter such as the major late promoter. In other embodiments, the replication-competent oncolytic virus is an adenovirus and the nucleic acid encoding the immune cell stimulatory receptor agonist and/or antagonist of an inhibitory signal of an immune cell is under the control of (i.e. operatively linked to) a non-adenoviral transcriptional and/or translational control sequence such as an enhancer, promoter and/or leader sequence from cytomegalovirus (CMV) (e.g. a CMV promoter), rous sarcoma virus (RSV) (e.g. an RSV promoter) or simian virus 40 (SV40) (e.g. an SV40 promoter). A "heterologous" region of the construct is an identifiable segment of nucleic acid within a larger nucleic acid molecule that is not found in association with the larger molecule in nature. The immune cell stimulatory receptor agonist expressed by the oncolytic virus and/or the antagonist of an inhibitory signal of an immune cell expressed by the oncolytic virus may be expressed on the surface of a tumor cell (i.e. may be inserted into the membrane of the tumor cell) or may be secreted from the tumor cell.

Tumor associated antigens (TAA) include, but are not limited to tumor associated antigens that have been identified as occurring in patients with brain cancers such as gliomas representative examples of which include: AIM2 (absent in melanoma 2), BMI1 (BMI1 polycomb ring finger oncogene), COX-2 (cyclooxygenase-2), TRP-1 (tyrosine related protein 2) TRP-2 (tyrosine related protein 2), GP100 (glycoprotein 100), EGFRvIII (epidermal growth factor receptor variant III), EZH2 (enhancer of zeste homolog 2), LICAM (human L1 cell adhesion molecule), Livin, Livinβ, MRP-3 (multidrug resistance protein 3), Nestin, OLIG2 (oligodendrocyte transcription factor), SOX2 (SRY-related HMG-box 2), ART1 (antigen recognized by T cells 1), ART4 (antigen recognized by T cells 4), SART1 (squamous cell carcinoma antigen recognized by T cells 1), SART2, SART3, B-cyclin, b-catenin, Gli1 (glioma-associated oncogene homolog 1), Cav-1 (caveolin-1), cathepsin B, CD74 (cluster of Differentiation 74), E-cadherin (epithelial calcium-dependent adhesion), EphA2/Eck (EPH receptor A2/epithelial kinase), Fra-1/Fosl 1 (fos-related antigen 1), GAGE-1 (G antigen 1), Ganglioside/GD2, GnT-V, β1,6-N (acetylglucosaminyltransferase-V), Her2/neu (human epidermal growth factor receptor 2), Ki67 (nuclear proliferation-associated antigen of antibody Ki67), Ku70/80 (human Ku heterodimer proteins subunits), IL-13Ra2 (interleukin-13 receptor subunit alpha-2), MAGE-A (melanoma-associated antigen 1), MAGE-A3 (melanoma-associated antigen 3), NY-ESO-1 (New York oesophageal squamos cell carcinoma 1), MART-1 (melanoma antigen recognized by T cells), PROX1 (prospero homeobox protein 1), PSCA (prostate stem cell antigen), SOX10 (SRY-related HMG-box 10), SOX11, Survivin, UPAR (urokinase-type plasminogen activator receptor, and WT-1 (Wilms' tumor protein 1). The replication-competent oncolytic virus (e.g. adenovirus) may express the full length tumor associated antigen or an immunogenic peptide thereof.

In one aspect, the replication-competent oncolytic virus, in addition to expressing an immune checkpoint inhibitor and optionally an immune cell stimulatory receptor agonist, also expresses EGFRvIII or an immunogenic peptide thereof on its surface. The sequence of EGFRvIII is described in U.S. Pat. No. 6,455,498, the content of which is hereby incorporated by reference. Immunogenic EGFRvIII peptides include those described in U.S. Patent Application Publication No. 2009/0155282, the content of which is hereby incorporated by reference, particularly those at paragraph [0362] and Tables 4.1-4.3. Preferably, the oncolytic virus is an adenovirus and EGFRvIII or an immunogenic peptide thereof is inserted into the gene encoding the fiber protein, preferably in the H1 loop. Nucleic acid encoding EGFRvIII or an immunogenic peptide thereof may be inserted into genes encoding one or more surface proteins of any adenovirus. The term "immunogenic EGFRvIII peptide" as used herein means a peptide of suitable length e.g. at least 10 or 12 amino acids and up to 15, 20, 25 or 30 amino acids or more which spans the mutated splice junction of the corresponding EGFRvIII protein, preferably human EGFRvIII. In a preferred embodiment, the nucleic acid inserted into an adenovirus surface protein encodes an 8-20 amino acid peptide consisting of, consisting essentially of, or comprising the sequence EKKGNYVV (SEQ ID NO: 1). In a particularly preferred embodiment, the EGFRvIII immunogenic peptide is LEEKKGNYVVT (SEQ ID NO: 2) and is inserted into the gene encoding the fiber protein, preferably in the H1 loop. In other embodiments, nucleic acid encoding the entire EGFRvIII extracellular domain is inserted into a gene encoding a surface protein of the adenovirus.

In a related aspect, the replication-competent oncolytic virus, in addition to expressing an immune checkpoint inhibitor and optionally an immune cell stimulatory receptor agonist, also expresses NY-ESO-1 (GenBank U87459.1) or an immunogenic peptide thereof (e.g. SLLMWITQCFLPVF (SEQ ID NO: 3)) on its surface. Preferably, the replication-competent oncolytic virus is an adenovirus and the nucleic acid encoding NY-ESO-1 or an immunogenic peptide thereof is inserted into a gene encoding a surface protein, whereby the adenovirus expresses a chimeric surface protein comprising the NY-ESO-1 or an immunogenic peptide thereof. In one aspect, nucleic acid encoding NY-ESO-1 or an immunogenic peptide thereof is inserted into the hypervariable region 5 of the gene encoding the hexon of the adenovirus.

Certain embodiments are directed to methods of treating and/or preventing cancer and/or treating and/or preventing a metastasis comprising administering to a tumor an effective amount of a replication competent oncolytic virus (e.g. adenovirus) expressing one or more immune checkpoint inhibitors as described above and/or expressing one or more immune cell stimulatory receptor agonists and optionally also expressing one or more tumor antigens, or administering an effective amount of a pharmaceutical composition comprising the replication-competent oncolytic virus. In certain aspects, the methods comprise administering to a tumor a Delta-24 or Delta-24-RGD adenovirus comprising one or more heterologous nucleic acid sequences encoding one or more immune checkpoint inhibitors and/or encoding one or more immune cell stimulatory receptor agonists and/or one or more tumor antigens inserted into one or more non-essential regions of the Delta-24 or Delta-24-RGD adenovirus backbone. In a preferred embodiment, part of the E3 region or all of the E3 region of the Delta-24 or Delta-24-RGD adenovirus genome is deleted and replaced with the heterologous nucleic acid(s). In some embodiments, the replication-competent adenovirus is administered to the tumor by one or more intratumoral injections. In certain preferred embodiments, the cancer is a glioma, primary or metastatic breast cancer or primary or metastatic lung cancer. In some embodiments, the replication competent oncolytic virus as described herein is administered to a human subject predisposed or susceptible to cancer in order to prevent the onset of cancer. In other embodiments, the replication competent oncolytic virus as described herein is administered to a human subject diagnosed with cancer. In related embodiments, the subject has metastatic cancer.

In a particularly preferred embodiment, the present invention provides a method for treating cancer (e.g. glioma) in a human subject by administering to the subject an effective amount of a Delta-24-RGD adenovirus comprising a heterologous nucleic acid sequence encoding an immune checkpoint inhibitor and/or comprising a heterologous nucleic acid sequence encoding an immune cell stimulatory receptor agonist (e.g. OX40L) and/or a heterologous nucleic acid encoding a tumor antigen, inserted into a non-essential region of the adenovirus backbone (e.g. a deleted E3 region). In certain preferred embodiments, the cancer is a glioma, primary or metastatic breast cancer or primary or metastatic lung cancer. In related preferred embodiments, a method for treating and/or preventing a metastasis in a subject diagnosed with cancer is provided comprising administering to the subject an effective amount of a replication-competent oncolytic virus expressing an immune checkpoint inhibitor and/or expressing an immune cell stimulatory receptor agonist and/or tumor antigen. In some embodiments, an oncolytic virus as described herein is administered to a subject predisposed or susceptible to cancer in order to prevent the onset of cancer. In other embodiments, an oncolytic virus as described herein is administered to a subject diagnosed with cancer. In related embodiments, the subject has metastatic cancer.

In certain preferred embodiments, a method for treating and/or preventing cancer (e.g. a glioma or primary or metastatic breast or lung cancer) in a human subject is provided comprising administering to the subject an effective amount of a Delta-24 or Delta-24-RGD adenovirus comprising one or more heterologous nucleic acid sequences encoding a PD-L1, PD-1 and/or CTLA4 inhibitor, wherein the PD-L1, PD-1 and/or CTLA4 inhibitor is expressed in a cancer cell of the subject.

In other preferred embodiments, a method for treating and/or preventing cancer (e.g. a glioma or primary or metastatic breast or lung cancer) in a human subject is provided comprising administering to the subject an effective amount of a Delta-24 or Delta-24-RGD adenovirus comprising (i) one or more heterologous nucleic acid sequences encoding a PD1, PD-L1, PD-L2 and/or CTLA4 inhibitor and/or (ii) one or more heterologous nucleic acid sequences encoding an OX40 ligand polypeptide and/or a GITR ligand polypeptide, wherein the OX40 ligand polypeptide and/or GITR ligand polypeptide and/or PD1 inhibitor and/or PD-L1 inhibitor and/or PD-L2 inhibitor and/or CTLA4 inhibitor is expressed in a cancer cell of the subject.

In one aspect, the subject to be treated is a human with a cancer that is refractory to treatment with one or more chemotherapeutic agents and/or refractory to treatment with one or more antibodies. For example, an oncolytic virus (e.g. adenovirus) expressing an immune checkpoint inhibitor may be administered to a human with cancer identified as a candidate for checkpoint inhibitor therapy.

In some aspects, treatment is determined by a clinical outcome such as, without limitation, increase, enhancement or prolongation of anti-tumor activity by T cells, an increase in the number of anti-tumor T cells or activated T cells as compared with the number prior to treatment or a combination thereof. In another aspect, clinical outcome is tumor stabilization, tumor regression, or tumor shrinkage.

The present invention also relates to a pharmaceutical combination for treating and/or preventing cancer and/or treating and/or preventing a metastasis.

Thus, in some embodiments, a combination therapy for use in the treatment and/or prevention of cancer and/or the establishment of metastases in a subject is provided comprising co-administering to the subject (i) a replication-competent oncolytic virus (e.g. adenovirus) expressing one or more immune cell stimulatory receptor agonists (e.g. OX40L and/or GITRL) in combination with (ii) one or more immune checkpoint inhibitors. In certain preferred embodiments, the oncolytic virus of the combination therapy is an adenovirus engineered to express an agonist for CD28, OX40 (CD134), GITR, CD137 (4-1BB), HVEM, ICOS (CD278), CD27, CD40, CD226, CRTAM, DR3, LTBR, TACI, BAFFR or BCMA. In particularly preferred embodiments, the oncolytic virus of the combination therapy is a modified Ad5 virus such as Delta-24 or Delta-24-RGD engineered to express an OX40 agonist (e.g. OX40L) and/or a GYM agonist (e.g. GITRL). In other preferred embodiments, the immune checkpoint inhibitor of the combination therapy is a monoclonal antibody, a humanized antibody, an antibody fragment, a fusion protein or a combination thereof that specifically binds to PD-1, PD-L1, PD-L2 or CTLA4. In particularly preferred embodiments, a combination therapy for use in the treatment and/or prevention of cancer (e.g. glioma) and/or the establishment of metastases in a subject is provided comprising co-administering to the subject (i) a replication competent Delta-24 or Delta-24-RGD adenovirus engineered to express OX40L and/or GITRL in combination with (ii) an anti-PD-1 and/or anti-PD-L1 monoclonal antibody. In some embodiments, the replication-competent oncolytic virus (e.g. adenovirus) of the combination also expresses an immune checkpoint inhibitor, in which case the immune checkpoint inhibitor expressed by the oncolytic virus of the combination and the immune checkpoint inhibitor of the combination preferably inhibit distinct immune checkpoint proteins. The oncolytic virus (e.g. adenovirus) and immune checkpoint inhibitor of the combination are administered simultaneously or sequentially in either order to the subject in need thereof and may be administered as part of the same formulation or in different formulations. In preferred embodiments, a first dose of the oncolytic virus is administered prior to a first dose of the immune checkpoint protein inhibitor. In other preferred embodiments, the oncolytic virus and the immune checkpoint protein inhibitor are administered intratumorally.

In other embodiments, a combination therapy for use in the treatment and/or prevention of cancer and/or the establishment of metastases in a subject is provided comprising co-administering to the subject (1) a replication-competent oncolytic virus (e.g. adenovirus) expressing an immune checkpoint inhibitor in combination with (ii) one or more agonists of an immune cell stimulatory receptor. In certain preferred embodiments, the oncolytic virus of the combination therapy is an adenovirus engineered to express an inhibitor of CTLA4, PD-1, B7-H3, B7-H4, TIM3, GAL9, LAG3, VISTA, KIR, TIGIT or BTLA or an inhibitor of a ligand thereof. In particularly preferred embodiments, the oncolytic virus of the combination therapy is a modified Ad5 virus such as Delta-24 or Delta-24-RGD engineered to express a PD-1, PD-L1 or CTLA4 inhibitor. In other preferred embodiments, the immune cell stimulatory receptor agonist of the combination therapy is an agonist of GITR or OX40. In particularly preferred embodiments, a combination therapy for use in the treatment and/or prevention of cancer and/or the establishment of metastases in a subject is provided comprising co-administering to the subject (1) a replication competent Delta-24 or Delta-24-RGD adenovirus engineered to express a PD-1, PD-L1 or CTLA4 inhibitor in combination with (ii) a GITR or OX40 agonist. In some embodiments, the replication-competent oncolytic virus (e.g. adenovirus) of the combination also expresses an immune cell stimulatory receptor agonist, in which case the immune cell stimulatory receptor agonist expressed by the oncolytic virus of the combination preferably binds to a different immune cell stimulatory receptor than the immune cell stimulatory receptor agonist of the combination. The oncolytic virus (e.g. adenovirus) and immune cell stimulatory receptor agonist of the combination are administered simultaneously or sequentially in either order to the subject in need thereof and may be administered as part of the same formulation or in different formulations. In some preferred embodiments, the oncolytic virus and the immune cell stimulatory receptor agonist are administered intratumorally.

In some embodiments, the replication competent oncolytic virus of a combination as described herein also expresses one or more tumor antigens.

In one aspect, the subject to be treated with a combination therapy as herein described is a human with a cancer that is refractory to treatment with one or more chemotherapeutic agents and/or refractory to treatment with one or more antibodies. For example, a checkpoint inhibitor (e.g. anti-PD-1 and/or anti-PD-L1) and oncolytic virus (e.g. adenovirus) expressing an immune cell stimulatory receptor agonist (e.g. OX40L) may be co-administered to a human with cancer identified as a candidate for checkpoint inhibitor therapy or even to a human with cancer who has failed one or more treatments with an immune checkpoint inhibitor.

In other embodiments, a replication-competent oncolytic virus expressing an immune cell stimulatory receptor agonist and/or expressing an antagonist of an inhibitory signal of an immune cell is combined with an additional cancer therapy such as radiotherapy, chemotherapy, hormone therapy, surgery and combinations thereof to treat and/or prevent cancer and/or treat and/or prevent metastasis in a subject.

DNA encoding an immune cell stimulatory receptor agonist or encoding an antagonist of an inhibitory signal of an immune cell can be inserted e.g. at any nonessential location in the oncolytic virus so long as the oncolytic virus remains replication competent. In one embodiment, the oncolytic virus is an adenovirus with a heterologous nucleic acid comprising a sequence encoding an immune cell stimulatory receptor agonist or a sequence encoding an antagonist of an inhibitory signal of an immune cell inserted downstream of the adenovirus fiber gene whereby expression of the encoded protein is driven by the adenovirus major late promoter. In a preferred embodiment, a heterologous nucleic acid comprising a sequence encoding an immune cell stimulatory receptor agonist or a sequence encoding an antagonist of an inhibitory signal of an immune cell is inserted in the E3 region of a replication-competent adenovirus backbone. The E3 region is nonessential for viral replication; however, the E3 proteins play a role in regulating host immune response. The replication-competent adenovirus can comprise a full or partial E3 deletion. For example, the replication-competent adenovirus can comprise deletions of one, two, three or more open reading frames (ORFs) in the E3 region and the heterologous nucleic acid inserted in its place. In one embodiment, the gp19k and 6.7K genes are deleted and the heterologous nucleic acid is inserted into a gp19k16.71 (deleted E3 region. In a related embodiment, the region between the BglII restriction enzyme sites at 78.3 and 85.8 map units of adenovirus type 5 genome may be deleted and the heterologous nucleic acid inserted into the deleted E3 region, as described in Bett et al., J. Virol., 67(10):5911-5922 (1993), the contents of which are incorporated herein by reference. In related aspects, the full E3 region is deleted from the replication-competent adenovirus backbone and the heterologous nucleic acid is inserted into a location containing the full E3 deletion. In a particularly preferred embodiment, the present invention provides a Delta-24 or Delta-24-RGD adenovirus comprising one or more heterologous nucleic acid sequences inserted in place of a partially or completely deleted E3 region, wherein the one or more heterologous nucleic acid sequences comprise a sequence encoding an OX40 agonist, preferably OX40L and/or a sequence encoding a GITR agonist, preferably GITRL and/or a sequence encoding a PD-1, PD-L1, PD-L2 and/or CTLA4 inhibitor and expression of the OX40 agonist, GITR agonist, PD-1 inhibitor, PD-L1 inhibitor, PD-L2 inhibitor and/or CTLA4 inhibitor is under the control of one or more non-adenoviral promoters such as a CMV promoter.

In some embodiments, the human subject exhibits a Th1 interluekine pattern. In other embodiments, the human subject exhibits a Th2 interleukine pattern. A subject is determined to exhibit a Th2 interleukine pattern if the subject has an IL-12/IL-4 ratio of less than about 20, less than about 15, or less than about 10. Subjects exhibiting a Th1 interleukine pattern will generally exhibit an IL-12/IL-4 ratio of greater than 20 and in some cases greater than 50, greater than 100 and even greater than 300. The IL-12/IL-4 ratio can be determined in the subject by obtaining a sample from the subject (e.g. a blood or serum sample), contacting the sample with antibodies against IL-12 and IL-4 and determining the amount of IL-12 and IL-4 in the sample as a function of the amount of binding of the antibodies to their respective antigens (e.g. by ELISA).

In related embodiments, one or more Th1 stimulating agents is co-administered with the replication competent oncolytic virus expressing one or more immune cell stimulatory receptor agonists and/or immune checkpoint inhibitors as described above to treat cancer (e.g. glioblastoma) in a subject. In some embodiments, the subject has an IL-12/IL-4 ratio of less than about 20 (i.e. exhibits a Th2 interluekine pattern). In other embodiments, the subject has an IL-12/IL-4 ratio of greater than about 20 (i.e. exhibits a Th1 interleukine pattern). Th1 stimulating agents include, without limitation, (i) Th1 cytokines such as IL-12p70, IL-2 and IFN-γ, (ii) agents that increase production of Th1 cytokines such as REVLIMID (lenalidomide) (iii) agents that suppress regulatory T cells (e.g. alkylating agents such as temozolomide (4-methyl-5-oxo-2,3,4,6,8-pentazabicyclo [4.3.0] nona-2,7,9-triene-9-carboxamide), cyclophosphamide ((RS)—N,N-bis(2-chloroethyl)-1,3,2-oxazaphosphinan-2-amine 2-oxide), lomustine (CCNU; N-(2-chloroethyl)-M-cyclohexyl-N-nitrosourea), bis-chloroethylnitrosourea (BCNU), melphalan hydrochloride (4 [bis(chloroethyl)amino]phenylalanine), busulfan (butane-1,4-diyl dimethanesulfonate), mechlorethamine (nitrogen mustard), chlorambucil, ifosfamide, streptozocin, dacarbazine (DTIC), thiotepa, altretamine (hexamethylmelamine), cisplatin, carboplatin, and oxalaplatin) and (iv) agents that stimulate cell mediated immune response (e.g. Ipilimumab, Tremelimumab, MDX-1106, MK-3475, AMP-224, Pidilizumab, and MDX-1105). Preferred Th1 stimulating agents to for co-administration with a replication competent oncolytic virus of the invention include IFN-γ (preferably recombinant) and temozolomide. The replication-competent oncolytic virus of the invention and a Th1 stimulating agent may be separately, concurrently or consecutively administered to a subject with cancer to treat the cancer. In one embodiment, the Th1 stimulating agent is administered to the subject and thereafter the replication-competent oncolytic virus is administered. In other related embodiments, a composition or kit is provided comprising (i) a Th1 stimulating agent and (ii) a replication-competent oncolytic adenovirus expressing one or more immune cell stimulatory receptor agonists and/or one or more immune checkpoint inhibitors as herein described, each in an amount effective to treat cancer in a subject in combination with the other. In a preferred embodiment, the composition or kit comprises (i) a Th1 stimulating agent selected from the group consisting of: recombinant IFN-γ, temozolomide, CCNU, BCNU, melphalan hydrochloride and busulfan and (ii) a replication-competent oncolytic adenovirus (e.g. Delta-24 or Delta-24-RGD) expressing an OX40 agonist (e.g. OX40L) and/or a GITR agonist (e.g. GITRL).

In other related embodiments, a method for monitoring responsiveness of a treatment with a replication competent oncolytic virus expressing one or more immune checkpoint inhibitors is provided comprising measuring a Th1 cytokine (e.g. IFNγ) in a sample (e.g. peripheral blood) from a patient treated with the virus, wherein an increased level of Th1 cytokine in the sample as compared to a reference (e.g. a level prior to treatment) indicates responsiveness to the treatment.

In another related embodiment, a method for monitoring responsiveness of a combination treatment with (i) a replicative oncolytic virus genetically modified to express an antagonist of an inhibitory signal of an immune cell and/or an immune cell co-stimulatory receptor agonist and (ii) a separately administered immune cell stimulatory receptor agonist and/or immune checkpoint inhibitor is provided comprising measuring a Th1 cytokine (e.g. IFNγ) in a sample (e.g. peripheral blood) from a patient treated with the combination, wherein an increased level of Th1 cytokine in the sample as compared to a reference (e.g. a level prior to treatment) indicates responsiveness to the combination treatment.

In a further aspect, a kit for use in inducing an immune response in a mammal is provided including (i) a replication competent oncolytic virus, preferably an adenovirus, engineered to express one or more immune cell stimulatory agonists and/or immune checkpoint inhibitors and (ii) an immune cell stimulatory agonist or immune checkpoint inhibitor. In some embodiments, the kit comprises (i) a replication competent oncolytic adenovirus comprising an adenovirus serotype 5 (Ad5) nucleic acid backbone or a hybrid nucleic acid backbone comprising an Ad5 component and a heterologous nucleic acid sequence encoding a Galt agonist or an OX40 agonist inserted in a nonessential region of the adenovirus genome, wherein the inserted heterologous nucleic acid sequence is under the control of a sequence permitting expression of the GITR agonist or OX40 agonist in a cell and (ii) a monoclonal antibody that specifically binds to PD-1, PD-L1, PD-L2 and/or CTLA4. The kit may further comprise instructions for using the combination for treating cancer. Certain aspects do not require the complete resection of the tumor, which is a limiting factor in recruitment of patients in other approaches. Furthermore, certain aspects of the current methods and compositions have the potential to generate memory in the immune system and preventing or reducing the probability of tumor recurrence.

The term "replication competent" refers to any viral vector that is not deficient in any gene function required for viral replication in specific cells or tissues. The vector must be capable of replicating and being packaged, but might replicate only conditionally in specific cells or tissues. Replication competent adenoviral vectors of the present invention are engineered as described herein to reduce or eliminate their ability to replicate in normal cells while retaining their ability to replicate efficiently in specific tumor disease cell types. Typically, a replication competent adenovirus comprises enough of the E1, E2, and E4 regions that the adenovirus is capable of replicating and being packaged without the need for elements to be supplied in trans.

The term "therapeutic benefit" or "treatment" refers to anything that promotes or enhances the well-being of the subject with respect to the medical treatment of his/her condition, which includes treatment of pre-cancer, cancer, and hyperproliferative diseases. A list of nonexhaustive examples of this includes extension of the subject's life by any period of time, decrease or delay in the neoplastic development of the disease, decrease in hyperproliferation, reduction in tumor growth, delay of metastases, reduction in cancer cell or tumor cell proliferation rate, and a decrease in pain to the subject that can be attributed to the subject's condition.

A "T regulatory cell" or "regulatory T cell" refers to a cell that can inhibit a T cell response. Regulatory T cells express the transcription factor Foxp3, which is not upregulated upon T cell activation and discriminates regulatory T cells from activated effector cells. Regulatory T cells are identified by the cell surface markers CD25, CD45RB, CTLA4, and GITR. Regulatory T cell development is induced by myeloid suppressor cell activity. Several regulatory T cell subsets have been identified that have the ability to inhibit autoimmune and chronic inflammatory responses and to maintain immune tolerance in tumor-bearing hosts. These subsets include interleukin 10- (IL-10-)secreting T regulatory type 1 (TrI) cells, transforming growth factor-β- (TGF-β-)secreting T helper type 3 (Th3) cells, and "natural" CD4+/CD25+ Tregs (Tm) (Fehervari and Sakaguchi. J. Clin. Invest. 2004, 1 14: 1209-1217; Chen et al. Science. 1994, 265: 1237-1240; Groux et al. Nature. 1997, 389: 737-742).

As used herein, an "agonist," e.g., an OX40 agonist, is a molecule which enhances the biological activity of its target, e.g., OX40. In certain aspects OX40 agonists, comprising, e.g., anti-OX40 antibodies or OX40 ligand compositions, substantially enhance the biological activity of OX40. Desirably, the biological activity is enhanced by 10%, 20%, 30%, 50%, 70%, 80%, 90%, 95%, or even 100%. In certain aspects, OX40 agonists as disclosed herein include OX40 binding molecules, e.g. binding polypeptides, anti-OX40 antibodies, OX40L, or fragments or derivatives of these molecules that specifically bind to OX40, e.g. human OX40. By "specifically bind" it is meant that the binding molecules exhibit essentially background binding to non-target (e.g. non-OX40) molecules. An isolated binding molecule that specifically binds OX40 may, however, have cross-reactivity to OX40 molecules from other species. In one embodiment, an immune cell co-stimulatory receptor agonist enhances the co-stimulatory signal mediated by or through cell surface proteins expressed on the immune cell.

As used herein, an "antagonist," e.g., a PD-1 antagonist, is a molecule which reduces the biological activity of its target, e.g. PD-1 by inhibiting the interaction of the target, e.g. PD-1, with one or more of its binding partners, e.g. PD-L1 or PD-L2. In certain aspects PD-1 antagonists, comprising, e.g., anti-PD-1 antibodies, substantially reduce the biological activity of PD-1. Desirably, the biological activity is reduced by 10%, 20%, 30%, 50%, 70%, 80%, 90%, 95%, or even 100%. In certain aspects, PD-1 antagonists as disclosed herein include PD-1 binding molecules, e.g. binding polypeptides, anti-PD-1 antibodies or fragments or derivatives of these molecules that specifically bind to PD-1, e.g. human PD-1. In one embodiment, an antagonist of an inhibitory signal of an immune cell reduces the negative co-stimulatory signal mediated by or through cell surface proteins expressed on the immune cell.

As used herein, a "checkpoint inhibitor" or "immune checkpoint inhibitor" means an agent which acts on surface proteins which are members of either the TNF receptor or B7 superfamilies, including agents which bind to negative co-stimulatory molecules including without limitation CTLA-4, PD-1, TIM-3, BTLA, VISTA, LAG-3, and/or their respective ligands, including PD-L1

The terms "Programmed Death 1", "Programmed Cell Death 1", "Protein PD-1" "PD-1" and "PD1" are used interchangeably, and include variants, isoforms, species homologs of human PD-1, and analogs having at least one common epitope with PD-1. The complete PD-1 sequence can be found under GenBank Accession No. U64863.

The terms "cytotoxic T lymphocyte-associated antigen-4," "CTLA-4," "CTLA4," and "CTLA-4 antigen" are used interchangeably, and include variants, isoforms, species homologs of human CTLA-4, and analogs having at least one common epitope with CTLA-4. The complete CTLA-4 nucleic acid sequence can be found under GenBank Accession No. L15006.

It is to be understood that "combination therapy" envisages the simultaneous, sequential or separate administration of the components of the combination. In one aspect of the invention, "combination therapy" envisages simultaneous administration of the oncolytic virus and checkpoint inhibitor or immune cell stimulatory receptor agonist. In a further aspect of the invention, "combination therapy" envisages sequential administration of the oncolytic virus and checkpoint inhibitor or immune cell stimulatory receptor agonist. In another aspect of the invention, "combination therapy" envisages separate administration of the oncolytic virus and checkpoint inhibitor or immune cell stimulatory receptor agonist. Where the administration of the oncolytic virus and checkpoint inhibitor or immune cell stimulatory receptor agonist is sequential or separate, the oncolytic virus and checkpoint inhibitor or immune cell stimulatory receptor agonist are administered within time intervals that allow that the therapeutic agents show a cooperative e.g., synergistic, effect. In preferred embodiments, the oncolytic virus and checkpoint inhibitor are administered within 1, 2, 3, 6, 12, 24, 48, 72 hours, or within 4, 5, 6 or 7 days or within 8, 9, 10, 11, 12, 13, 14, 15, 16, 17, 18, 19, 20, 21, 22, 23, 24, 25, 26, 27, 28, 29, 30 or 31 days of each other.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa. Furthermore, compositions and kits of the invention can be used to achieve methods of the invention.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 6A: D24-RGD and D24-RGDOX induce release of HMGB1. GL261 cells were infected with the indicated viruses at 200 pfu/cell. 24 hour slater, the concentration of FBS was lowered from 10% to 2%. Culture medium (M) and whole cell lysates (W) were collected at the indicated time points and HSP90 and HMGB1 expression levels were analyzed with immunoblotting. The relative levels of HMGB1 in the medium are shown at the bottom of the panel. FIG. 6B: GL261 cells were infected with the indicated viruses at 100 pfu/cell. 72 hours later, the cell lysates were analyzed with immunoblotting for the cytosolic form of microtubule-associated protein 1A/1B-light chain 3 (LC3 I), or its phosphatidylethanolamine conjugate (LC3 II). The LC3 II/I ratio is used to monitor autophagy. The E1A levels were used as an indicator of the relative viral dose and normalized to the value in the D24-RGD group, which was set to 1. α-tubulin levels are shown as a protein loading control. AdGFP was used as a replication-deficient viral vector control. FIG. 6C: GL261 cells were infected with the indicated viruses at 100 pfu/cell. Cells were harvested after 72 hours and cell lysis (cell death) was monitored with ethidium homodimer-1 staining and analyzed with flow cytometry. FIGS. 6D and 6E: To assess immunogenic cell death induced by the viruses, GL261 cells were infected with the indicated viruses at 100 pfu/cell. After 72 hours, culture medium was collected and assayed for the amount of ATP (FIG. 6D) or HMGB1 (FIG. 6E). The relative ATP levels (FIG. 6D, 1=average amount of ATP in mock-treated cells) and HMGB1 concentrations (FIG. 6E) are shown. Values represent the mean±standard deviation (n=3). NS: not significant (P≥0.05); * P<0.0002, **P=0.001, 2-tailed Student's t test. Mock: PBS; D24RGD: Delta-24-RGD; D24-RGDOX; Delta-24-RGDOX.

FIG. 7A: Cartoon depiction of the treatment scheme. i.e.: intracranial; i.t.: intratumoral. FIGS. 7B-C: GL261 cells were implanted into the brain of C57BL/6 mice. Animals were randomly separated by groups (n=9-10) and treated (by intratumoral injections on days 3, 6 and 8 after tumor implantation) with PBS, D24-RGDOX ($5 \times 10^7$ pfu), D24-RGD ($5 \times 10^7$ pfu), OX86 (a-mouse OX40 antibody) (25 μg), or D24-RGD in combination with OX86 ($5 \times 10^7$ pfu+25 μg respectively). Survival plots of the different treatment groups in C57BL/6 (immunocompetent, FIG. 7B) or athymic (immunodeficient, FIG. 7C) mice (n=10 per group, except n=9 per group for OX86+Delta-24-RGD in FIG. 7B) are shown. FIG. 7D: cells from a selected clone of GL261 (GL261-5), characterized by a slower growing rate, were implanted into the brain of C57BL/6 mice. Animals were randomly separated into groups (n=10, except n=8 for D-24-RGD) and treated with PBS, D24-RGDOX or D24-RGD by intratumoral injections on days 6, 8 and 10 after tumor implantation. Survival plots of mice in the treatment groups bearing slow-growing GL261-5 gliomas (n=6) are shown. FIG. 7E: Survival plots for surviving members of the group treated with Delta-24-RGDOX, as shown in FIG. 7D, when rechallenged with GL261-5 (n=6). FIG. 7F: Survival plots for surviving members of the group treated with Delta-24-RGDOX when rechallenged with B16-F10 cells (n=4). FIG. 7G: Delta-24-RGDOX induced necrosis (necr.) in gliomas taken from C57BL/6 mice. Upper panel: representative hematoxylin and eosin-stained sections of the brains from treatment groups showing tumor (T) and normal brain (N) tissue. Lower panel: enlarged images of areas within the tumor. Representative results from at least 6 mice from each group in FIG. 7B are shown. The numbers at the bottom indicate the number of days between tumor implantation and the sacrificing of the mice. Scale: upper panel, 200 µm; lower panel, 50 µm. NS: not significant (P≥0.05); P<0.001, log-rank test. D24RGD: Delta-24-RGD; D24-RGDOX; Delta-24-RGDOX.

FIG. 8A: Lymphocyte infiltration at the tumor site induced by Delta-24-RGDOX. GL261 cells ($5 \times 10^4$) were grafted into the caudate nucleus of C57BL/6 mice. Gliomas in C57BL/6 mice were treated with the indicated viruses (D24-RGD or D24-RGDOX administered intratumorally) or PBS on days 6, 8, and 10 after GL261 cell intracranial implantation. On day 14 of the experiment, brains were collected and analyzed. Brain-infiltrating leukocytes (BILs) from brain hemispheres with tumors of glioma-bearing mice treated with PBS or the indicated viruses were isolated and examined for the indicated cell surface markers using flow cytometry to assess numbers of tumor-infiltrating lymphocytes (CD45+CD3+), helper T lymphocytes (CD45+CD3+CD4+) and cytotoxic T lymphocytes (CD45+CD3+CD8+) at the tumor site. P values are indicated (Student's t-test, double sided). D24-RGDOX treatment is shown to result in higher recruitment of immune cells into the tumor bed than D24-RGD. FIGS. 8B and 8C: Immune response against glioma cells induced by Delta-24-RGDOX. Gliomas were treated as described for FIG. 8A. On day 14 after tumor implantation, BILs (FIG. 8B) or splenocytes (FIG. 8C) taken from the three groups of mice described above (5 mice per group) were stimulated with pre-fixed GL261 cells that were uninfected, or had been infected with the indicated virus, 40 hours later, the concentration of IFNγ in the supernatant was assessed using a standard ELISA. FIG. 8D: Inhibition of Delta-24-REDOX-mediated activation of BILs by an anti-mouse OX40L antibody. BILs from hemispheres (taken from 9 mice) with Delta-24-RGDOX-treated tumors were isolated and stimulated with pre-fixed GL261 cells that had been infected with Delta-24-RGD or Delta-24-RGDOX in the presence of control immunoglobulin G (IgG) or anti-mouse OX40L antibody (4 µg/ml) as described for FIG. 8B. The concentration of IFNγ in the supernatant was assessed using ELISA. Values represent the mean±SD (n=3). NS: not significant (P≥0.05); * P<0.0001, **P<0.05, 2-tailed Student's t test. D24RGD: Delta-24-RGD; D24-RGDOX; Delta-24-RGDOX.

FIG. 9A: D24-RGDOX induced in vitro proliferation of lymphocytes recognizing tumor-associated antigen (TAA). OVA-specific CD8+ T cells (from the spleens of 4 OT-I mice; OVA-specific TCR transgenic line of mice described in Hogquist et al., Cell, 76:17-27 (1994)) pre-stained with CFSE were incubated with the indicated pre-fixed target cells. After 4 days, the cells were analyzed with flow cytometry for CFSE amount to measure cell proliferation. Right panel: Cells were gated for CD8+ and representative dot plots are shown. The numbers at the upper left corners indicate the percentage of proliferating T-cells. Unstimulated T-cells (no stimulation) were used as a negative control and T cells stimulated with pre-fixed mouse dendritic cells (mDCs) primed with OVA (257-264) peptide (mDC/OVA (257-264) were used as a positive control. Left panel: Quantification of the proliferating T-cells. Shown are the percentages of the proliferating CD8+ cells after stimulation with the indicated pre-fixed target cells::GL261-OVA cells ($1^{st}$ bar); GL261-OVA cells infected with Delta-24-RGD ($2^{nd}$ bar); GL261-OVA cells infected with D24-RGDOX ($3^{rd}$ bar); and GL261 cells infected with D24-RGDOX ($4^{th}$ bar) FIGS. 9B-9C: Tumor-specific immunity induced by Delta-24-RGDOX. GL261-OVA cells ($5 \times 10^4$) were grafted into the caudate nucleus of C57BL/6 mice. Tumors were established as in FIG. 8A, D24-RGD or D24-RGDOX ($5 \times 10^7$ pfu) or PBS (control) were injected intratumorally on days 6, 8 and 10 after tumor implantation. FIG. 9B: On day 14 after tumor implantation, OVA-specific CD8+ T cells were isolated from mouse spleens (5 mouse spleens per treatment group) of GL261-OVA glioma-bearing mice and then stimulated (co-cultured) with pre-fixed mouse dendritic cells (mDCs) primed with OVA. (257-264) peptide for 40 hours. FIG. 9C: splenocytes isolated from the above treatment groups were stimulated (co-cultured) with pre-fixed mouse astrocytes (MAs) or GL261-OVA cells for 40 hours. The concentration of IFNγ in the supernatant in each case was assessed with standard ELISA. Values represent mean±SD (n=3). P≤0.001, 2-tailed Student's t test. D24-RGD: Delta-24-RGD; D24-RGDOX: Delta-24-RGDOX. Phosphate buffered saline (PBS) was used as a vehicle to dilute virus stocks.

FIG. 12A: PD-L1 expression in human glioma stem cells (GSCs with serial numbers), Cells were cultured with or without human IFNγ (200 U/ml) for 48 hours and then stained with anti-human PD-L1 APC (eBiosciences) and analyzed for PD-L1 expression by median fluorescence intensity (MFI) Data are shown as mean±SD (n=3). FIG. 12B: PD-L1 expression in mouse glioma GL261-5 cells. Cells were mock infected with PBS or infected with Delta-24-REDOX (100 PFU/cell) in the presence or absence of mouse IFNγ (100 units/ml) for 48 hours and then stained with anti-mouse PD-L1 APC and analyzed with flow cytometry for PD-L1 expression. Data on MFI are shown as numerical values. FIG. 12C: PD-L1 expression was assessed in vivo in mice bearing GL261.GFP-derived intracranial xenografts according to the indicated schedule. FIG. 12D: PD-L1 expression in glioma cells from implanted tumors. Fourteen days after implantation of GL261 cells expressing enhanced green fluorescent protein (EGFP), Delta-24-REDOX (D24-RGDOX) was injected intratumorally. After 24 hours, the tumors (taken from 3 mice/group) were harvested, dissociated, and analyzed with flow cytometry for PD-L1 expression. Tumor cells were gated from EGFP+. IgG staining was used as a negative control. The colored numbers indicate the MFI for the curve of the same color in FIGS. 12B and 12C (FIG. 12B "Mock": 37.4=α-PD-L1; 661=IFNγ/α-PD-L1; FIG. 12B "D24-RGDOX": 59.7=α-PD-L1; 529=IFNγ/α-PD-L1) (FIG. 12C: 750=Mock/α-PD-L1; 1176=D24-RGDOX/α-PD-L1). FIG. 12E: Effect of Delta-24-RGDOX on CTLA-4 and PD-1 expression in CD8+ T cells. Expression of CTLA-4 or PD-1 on the T cells from BILs in glioma-bearing mice treated with PBS or Delta-24-REDOX as shown in FIG. 8A was assessed with flow cytometry. The relative expression levels are shown. The values from the mock-treated (PBS) group were set to 100%. Data are shown as relative MFI (Mean±SD). NS: not significant (P≥0.05); * P=0.0007, 2-tailed Student's t test.

FIG. 13A: Scheme of the schedule treatment and testing of anti-tumor immune memory in the GL261-5 murine glioma model. i.e.: intracranial; i.t.: intratumoral. Gliomas were treated with 2 doses of D24-RGDOX (intratumoral injection of 5×10$^7$ pfu) on days 6 and 10 and/or rat IgG or anti-PD-L1 (25 μg injected intratumorally) on days 8 and 13 after tumor implantation as illustrated in the treatment scheme, FIG. 13B: Complete tumor regression induced by the combination of Delta-24-RGDOX and anti-PD-L1 antibody in long-term surviving mice. A representative hematoxylin and eosin-stained, whole-mount coronal mouse brain section (left, sacrificed on day 104 after tumor implantation) from the long-term surviving mice treated with the combination is shown. The arrow marks a residue dent left by the screw for guiding the tumor implantation and viral injections. Tumor sequel (marked with dashed lines in the left panel, also enlarged on the right) is present at the tumor implantation site. FIG. 13C: Kaplan-Meier survival plots of the overall survival outcome of C57BL/6 mice bearing GL261-5 gliomas mock treated (n=19) or treated with anti-PD-L1 antibody (αPD-L1) (n=20), Delta-24-REDOX (n=18) or the combination of Delta-24-RGDOX and αPD-L1) (n=20). P value was obtained using the log rank test. FIG. 13D: Kaplan-Meier survival plots of the group treated with Delta-24-RGDOX together with α-PD-L1 in FIG. 13C when re-challenged with GL261-5 in the contralateral hemisphere rather than the hemisphere with the originally treated tumor. Naïve: n=10; Survivor: n=6, *P≤0.0001, log-rank test, D24-RGDOX: Delta-24-RGDOX.

DESCRIPTION

Figure 1:
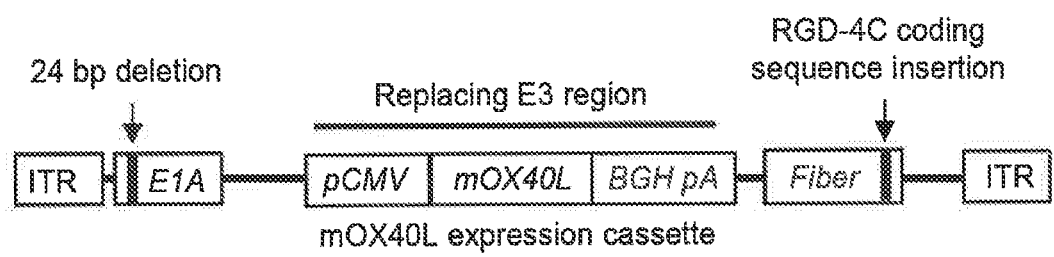
FIG. 1, Schematic representation of the Delta-24-RGDOX genome, including a 24-base pair deletion in the E1A gene that encodes an RB-binding region and an insertion in the fiber gene that encodes an integrin-binding motif (RGD-4C) in the HI loop of the protein. The mouse OX40L (mOX40L) expression cassette, including the cytomegalovirus (CMV) promoter (pCMV), mOX40L cDNA, bovine growth hormone poly-adenylation signal (BGH pA), replaced the E3 region of the human Adenovirus 5 genome. ITR: inverted terminal repeat. In another construct, cDNA encoding mouse OX40L was inserted downstream of the fiber gene of the adenoviral genome and expression of OX40L was driven by the endogenous adenoviral late promoter.

Methods and compositions of the present invention include the construction and verification of oncolytic viruses (e.g. adenoviruses) comprising heterologous nucleic acid sequence(s) encoding one or more immune checkpoint protein inhibitors, and/or one or more immune cell co-stimulatory receptor agonists and/or tumor antigens, that exhibit enhanced and even synergistic anti-tumor effects compared to the unmodified oncolytic virus (i.e. genetically similar or identical oncolytic virus not containing heterologous nucleic acid encoding an immune checkpoint protein inhibitor) and the immune cell stimulatory receptor agonist and/or immune checkpoint inhibitor when administered separately. A pharmaceutical combination for treating and/or preventing cancer and for treating and/or preventing a metastasis is also provided comprising (i) a replication-competent oncolytic virus expressing an immune cell stimulatory receptor agonist and/or immune checkpoint inhibitor and (ii) an immune cell stimulatory receptor antagonist or immune checkpoint inhibitor.

In several aspects, a replication-competent adenovirus engineered to comprise a heterologous nucleic acid encoding an inhibitor of an immune checkpoint protein selected from the group consisting of: CTLA4, PD-1, PD-L1, PD-L2, B7-H3, B7-H4, TIM3, GAL9, LAG3, VISTA, KIR, TIGIT and BTLA, a pharmaceutical composition comprising such a replication-competent adenovirus and the use of such a replication-competent adenovirus in treating and/or preventing cancer and its use in treating and/or preventing metastases is provided.

In other aspects, a replication-competent adenovirus engineered to comprise a heterologous nucleic acid encoding an agonist of an immune cell stimulatory receptor selected from the group consisting of CD28, OX40, GITR, CD137, HVEM, ICOS, CD27, CD40, CD226, CRTAM, DR3, LTBR, TALI, BAFFR and BCMA, a pharmaceutical composition comprising such a replication-competent adenovirus and the use of such a replication-competent adenovirus in treating and/or preventing cancer and its use in treating and/or preventing metastases is provided. In some preferred embodiments, the replication-competent adenovirus is engineered to comprise heterologous nucleic acid encoding an antibody or antibody fragment that specifically binds to (and inhibits) an immune checkpoint protein. A heterologous nucleic acid encoding either or both of a $V_H$ region or $V_L$ region can be used to produce an antibody or antibody fragment that specifically binds to an immune checkpoint inhibitor. For example, the heterologous nucleic acid may comprise a single gene encoding a single chain protein containing a $V_H$ region and $V_L$ region connected by a linker, such as a scFv, or may comprise distinct regions to, for example, produce both $V_H$ and $V_L$ regions. In some embodiments, the replication-competent adenovirus comprises a heterologous nucleic acid containing sequences encoding the heavy and light chains of a human monoclonal antibody that specifically binds to (and inhibits) an immune checkpoint protein under the control of regulatory elements directing their expression.

Monoclonal antibodies that specifically bind to (and block) CTLA4 include, without limitation, Ipilimumab (Yervoy®) and Tremelimumab (CP 675,206), as well as antibodies disclosed in U.S. Patent Application Publication Nos. 2005/0201994, 2002/0039581, and 2002/086014, the contents of each of which are incorporated herein by reference.

Monoclonal antibodies that specifically bind to (and block) PD-1 include, without limitation, lambrolizumab and other humanized antibodies described in U.S. Pat. No. 8,354,509, incorporated herein by reference, Nivolumab (BMS-936558), Pembrolizumab (Keytruda®) and Pidilizumab (CT-011).

Monoclonal antibodies that specifically bind to (and block) PD-L1 include, without limitation, BMS-936559 (MDX-1105), pembrolizumab (MK-3475), Atezolizumab (MPDL33280A), Durvalumab (MEDI4736), MIH1, and Avelumab (MSB0010718C) as well as antibodies disclosed in U.S. Pat. Nos. 8,779,108 and 8,217,149, the contents of which are incorporated herein by reference.

Antibodies that specifically bind to (and block) human LAG3 include BMS-986016 as well as those described in U.S. Patent Application Publication Nos. 2010-0233183 and 2011-0150892, each of which is incorporated herein by reference.

Antibodies that specifically bind to (and block) BLTA include antibody 4C7 disclosed in U.S. Pat. No. 8,563,694, the contents of which are incorporated herein by reference.

Antibodies that specifically bind to (and block) B7H4 include antibodies disclosed in U.S. Patent Application Publication No. 2014/0294861, the contents of which are incorporated herein by reference.

Antibodies that specifically bind to (and block) B7-H3 include antibody MGA271 and others disclosed U.S. Patent Application Publication No. 20120294796, the contents of which are incorporated herein by reference.

Antibodies that specifically bind to (and block) TIM3 include antibodies disclosed in U.S. Pat. No. 8,841,418, incorporated herein by reference and the TIM3 blocking antibody F38-2E2 disclosed by Jones et al., J. Exp. Med., 205(12):2763-79 (2008).

Antibodies that specifically bind to (and block) KIR include the antibody lirilumab (described in Romagne et al., Blood, 114(13):2667-2677 (2009).

In a preferred embodiment, the replication-competent oncolytic virus comprises (i) an adenovirus serotype 5 (Ad5) nucleic acid backbone (ii) a heterologous nucleic acid sequence encoding a PD-1 inhibitor and/or (iii) a heterologous nucleic acid sequence encoding a PD-L1 inhibitor and/or (iv) a heterologous nucleic acid sequence encoding a PD-L2 inhibitor and/or (v) a heterologous nucleic acid sequence encoding a CTLA4 inhibitor and optionally (vi) a 24 bp deletion (D24) in the Rb binding constant region 2 of E1 and optionally (vii) an insertion of the RGD-4C sequence into the H1 loop of the fiber knob protein. In a particularly preferred embodiment, the replication-competent oncolytic virus comprises a Delta-24 or Delta-24-RGD adenovirus nucleic acid backbone engineered to comprise one or more heterologous nucleic acid sequences encoding a PD1, PD-L1 or CTLA-4 inhibitor each operably linked to a suitable promoter. In related embodiments, the heterologous nucleic acid sequence encoding a PD1, PD-L1 or CTLA-4 inhibitor is in the place of a deleted E3 region (e.g. adenoviral genes gpl9K/6.7K). In other related embodiments, the heterologous nucleic acid sequence encodes an antibody or antibody fragment.

In other preferred embodiments, the replication-competent adenovirus is engineered to comprise heterologous nucleic acid encoding a soluble form of a checkpoint protein or a fusion protein comprising a soluble form of a checkpoint protein fused to another polypeptide such as the Fc region of human IgG, that blocks the immune checkpoint protein. Nonlimiting examples include AMP-224, a recombinant fusion protein comprising the extracellular domain of PD-L2 and the Fe region of human IgG that block PD-1, IMP321, soluble LAG3 Ig fusion proteins that block LAG3, and soluble recombinant forms of B71714 disclosed in U.S. Patent Application Publication No. 20120177645, incorporated herein by reference, that block LAG3.

In several aspects, a replication-competent adenovirus is provided that is engineered to comprise (i) heterologous nucleic acid sequence encoding an inhibitor of an immune checkpoint protein selected from the group consisting of: CTLA4, PD-1, PD-L1, PD-L2, B7-H3, B7-H4, TIM3, GAL9, LAG3, VISTA, KIR, and BTLA; and (ii) heterologous nucleic acid sequence encoding an agonist of an immune cell stimulatory receptor selected from the group consisting of CD28, OX40, GITR, 4-1BB, HVEM, ICOS, CD27, CD40, CD226, CRTAM, DR3, LTBR, TACI, BAFFR and BCMA, a pharmaceutical composition comprising such a replication-competent adenovirus and the use of such a replication-competent adenovirus in treating and/or preventing cancer and its use in treating and/or preventing metastases.

In one embodiment, the replication-competent adenovirus expresses an immune checkpoint inhibitor and also expresses a CD28 agonist such as human CD80 (B7.1), GenBank Accession Nos. NM_005191 (mRNA) and NP_005182 (protein) or CD86 (B7.2), GenBank Accession No. NM_175862 (mRNA) and accession no. P42081 in the Swiss-Prot database. In another embodiment, the replication-competent adenovirus expresses an immune checkpoint inhibitor and also expresses an agonist of 4-1BB such as human 4-1BBL, the full amino acid sequence of which can be found under accession no. P41273 in the Swiss-Prot database. In another embodiment, the replication-competent adenovirus expresses an immune checkpoint inhibitor and also expresses an agonist of HVEM such as human lymphotoxin-like (LIGHT), the full amino acid sequence of which can be found under accession no. 043557 in the Swiss-Prot database.

In one preferred embodiment, the replication-competent adenovirus expresses an immune checkpoint inhibitor and also expresses an agonist of GITR such as human GITR ligand or a GITR receptor-binding fragment of GITR ligand or a GITR ligand fusion protein (e.g. consisting of amino acids 50-177 of human GITRL fused to an Fc fragment of an immunoglobulin). Human GITR ligand (a.k.a. GITR-L, TNFSF18 (tumor necrosis factor (ligand) superfamily, member 18)) is a type II membrane protein containing 177 amino acids (see sequence in Swiss Prot Id no. Q9UNG2). GITR ligand contains a cytoplasmic domain at residues 1-28, a transmembrane domain at resides 29-49 and an extracellular domain at residues 50-177. The nucleotide sequence of GITR-L is publicly available (e.g. Genbank accession no. NM 005092.2). Preferably, GITR ligand shares at least 80% amino acid sequence identity, preferably at least 90% sequence identity, more preferably at least 95% sequence identity and even more preferably at least 98% sequence identity with GITR-L as defined in Swiss Prot Id. no. Q9UNG2, Other GITR agonists that can be expressed by the replication competent oncolytic adenovirus include antibodies against GITR such as those described in U.S. Patent Application Publication No. 2015/0353637, the contents of which are incorporated herein by reference and those described in U.S. Pat. No. 8,709,424, the contents of which are incorporated herein by reference. Other non-limiting examples of anti-GITR antibodies that can be expressed by the replication competent oncolytic adenovirus include DTA-1 (anti-mouse GITR mAb), TRX518 (humanized anti-GITR mAb) and MK-4166 (anti-human GITR mAb).

In another preferred embodiment, the replication-competent adenovirus expresses an immune checkpoint inhibitor and also expresses an agonist of OX40 such as OX40 ligand (OX40L or gp34) or an OX40 receptor-binding fragment of OX40L or an OX40L fusion protein such as those described in U.S. Pat. No. 7,959,925, the content of which is incorporated herein by reference. A functionally active soluble form of OX40 ligand may be produced by deleting the intracellular and transmembrane domains as described in U.S. Pat. No. 5,457,035 and WO 95/21915. Methods of making and using OX40 ligand and its derivatives are described in WO 95/21915, which also describes proteins comprising the soluble form of OX-40 ligand linked to other peptides, such as human Ig Fc regions, that can be produced e.g. to enhance the stability of the molecule after in vivo administration to a mammal. The amino acid sequence of human OX40L is described at GenBank Accession Number NP 003317.1 and Swiss Prot Id. no. P23510. Full cDNA encoding human OX40L is at NCBI Reference Sequence: NM_003326.3. Human OX40L shares 46% amino acid sequence identity with its mouse counterpart. Preferably, OX40 ligand shares at least 80% amino acid sequence identity, preferably at least 90% sequence identity, more preferably at least 95% sequence identity and even more preferably at least 98% sequence identity with OX40 ligand as defined in Swiss Prot Id. no. P23510. Other OX40 agonists that can be expressed by the replication-competent oncolytic adenovirus include antibodies against OX40 (e.g. anti-human OX40 antibodies) such as those described in U.S. Pat. Nos. 6,312,700, 7,504,101, 7,291,331, 7,550,140, 7,807,156, and 7,960,515, the entire contents of each of which are incorporated herein by reference. Specific non-limiting examples of OX40 antibody include MEDI6469, MEDI0562, MEDI6383, LI 06 BD, 112F32, 112V8, 112Y55, 112Y131, 112Z5, mAb 315, mAb131, mAb 2G2, IF7, ACT35, mAb L106 and mAb OX86. Other OX40 agonists include those described in U.S. Patent Application Publication No. US20060281072, the entire content of which is incorporated herein by reference.

In another preferred embodiment, the replication-competent oncolytic virus comprises (i) an adenovirus serotype 5 (Ad5) nucleic acid backbone (ii) heterologous nucleic acid sequence(s) encoding an OX40 agonist and/or a GITR agonist (iii) heterologous nucleic acid sequence(s) encoding a PD-1, PD-L1, PD-L2 and/or CTLA4 inhibitor and optionally (iv) a 24 bp deletion (D24) in the Rb binding constant region 2 of E1 and optionally (v) an insertion of the RGD-4C sequence into the H1 loop of the fiber knob protein. In a particular) preferred embodiment, the replication-competent oncolytic virus comprises a Delta-24 or Delta-24-RGD adenovirus nucleic acid backbone engineered to comprise (i) heterologous nucleic acid sequence(s) encoding an OX40 ligand polypeptide and/or a GITR ligand polypeptide and (ii) heterologous nucleic acid sequence(s) encoding a PD-1 and/or PD-L1 and/or CTLA4 inhibitor, the heterologous nucleic acid sequence in each case operably linked to a suitable promoter. In related embodiments, heterologous nucleic acid sequence encoding OX40 ligand polypeptide and/or GITR ligand polypeptide and heterologous nucleic acid sequence encoding PD-1 and/or PD-L1 and/or CTLA4 inhibitor is in the place of a deleted E3 region (e.g. adenoviral genes gpl9K/6.7K). In other related embodiments, the heterologous nucleic acid sequence encoding an immune cell stimulatory receptor agonist encodes a soluble or membrane bound OX40 ligand polypeptide and/or a soluble or membrane bound GITR ligand polypeptide and the heterologous nucleic acid sequence encoding an immune checkpoint inhibitor encodes a monoclonal antibody or antibody fragment that specifically binds to PD-1 and/or PD-L1 and/or CTLA4.

In another preferred embodiment, the replication-competent adenovirus expresses an agonist of GITR such as human GITR ligand or a GITR receptor-binding fragment of GITR ligand or a GITR ligand fusion protein (e.g. consisting of amino acids 50-177 of human GITRL fused to an Fc fragment of an immunoglobulin). Preferably, GITR ligand shares at least 80% amino acid sequence identity, preferably at least 90% sequence identity, more preferably at least 95% sequence identity and even more preferably at least 98% sequence identity with GITR-L as defined in Swiss Prot Id. no. Q9UNG2. Other GITR agonists that can be expressed by the replication competent oncolytic adenovirus include antibodies against GITR such as those described in U.S. Patent Application Publication No. 2015/0353637, the contents of which are incorporated herein by reference and those described in U.S. Pat. No. 8,709,424, the contents of which are incorporated herein by reference. Other non-limiting examples of anti-GITR antibodies that can be expressed by the replication competent oncolytic adenovirus include DTA-1 (anti-mouse GITR TRX518 (humanized anti-GITR mAb) and MK-4166 (anti-human GITR mAb).

In another preferred embodiment, the replication-competent adenovirus expresses an agonist of OX40 such as OX40 ligand (OX40l, or gp34) or an OX40 receptor-binding fragment of OX40L or an OX40L fusion protein such as those described in U.S. Pat. No. 7,959,925, the content of which is incorporated herein by reference. Preferably, OX40 ligand shares at least 80% amino acid sequence identity, preferably at least 90% sequence identity, more preferably at least 95% sequence identity and even more preferably at least 98% sequence identity with OX40 ligand as defined in Swiss Prot Id. no. P23510. Other OX40 agonists that can be expressed by the replication-competent oncolytic adenovirus include antibodies against OX40 (e.g. anti-human OX40 antibodies) such as those described in U.S. Pat. Nos. 6,312,700, 7,504,101, 7,291,331, 7,550,140, 7,807,156, and 7,960,515, the entire contents of each of which are incorporated herein by reference. Specific non-limiting examples of OX40 antibody include MEDI6469, MEDI0562, MEDI6383, LI 06 BD, 112F32, 112V8, 112Y55, 112Y131, 112Z5, mAb 315, mAb131, mAb 2G2, IF7, ACT35, mAb L106 and mAb OX86. Other OX40 agonists include those described in U.S. Patent Application Publication No. US20060281072, the entire content of which is incorporated herein by reference.

In some aspects, a combination therapy for treating and/or preventing cancer and or for treating and/or preventing metastases is provided comprising co-administering to a subject in need thereof an effective amount of: (1) a replication-competent adenovirus engineered to comprise a heterologous nucleic acid encoding an agonist of an immune cell stimulatory receptor selected from the group consisting of: CD28, OX40, GITR, 4-1BB, HVEM, ICOS, CD27, CD40, CD226, CRTAM, DR3, LTBR, TACI, BAFFR and BCMA; and (ii) an inhibitor of an immune checkpoint protein selected from the group consisting of: CTLA4, PD-1, PD-L1, PD-L2, B7-H3,137-H4, TIM3, GAL9, LAG3, VISTA, KIR, TIGIT and BMA.

An immune checkpoint inhibitor for use in the pharmaceutical combination herein described is any compound capable of inhibiting the function of an immune checkpoint protein. Inhibition includes reduction of function as well as full blockade. In particular, the immune checkpoint protein is a human checkpoint protein. Thus, the immune checkpoint inhibitor is preferably an inhibitor of a human immune checkpoint.

In preferred embodiments, the immune checkpoint inhibitor of the combination is an antibody. The term "antibody" as used herein encompasses naturally occurring and engineered antibodies as well as full length antibodies or functional fragments or analogs thereof that are capable of binding e.g. the target immune checkpoint or epitope (i.e. retaining the antigen-binding portion). The antibody for use according to the methods described herein may be from any origin including, without limitation, human, humanized, animal or chimeric and may be of any isotype with a preference for an IgG1 or IgG4 isotype and further may be glycosylated or non-glycosylated. The term antibody also includes bispecific or multispecific antibodies so long as the exhibit the binding specificity herein described.

Humanized antibodies refer to non-human (e.g. murine, rat, etc.) antibody whose protein sequence has been modified to increase similarity to a human antibody. Chimeric antibodies refer to antibodies comprising one or more element(s) of one species and one or more element(s) of another specifies, for example a non-human antibody comprising at least a portion of a constant region (Fe) of a human immunoglobulin.

Many forms of antibody can be engineered for use in the combination of the invention, representative examples of which include an Fab fragment (monovalent fragment consisting of the VL, VH, CL and CH1 domains), an F(ab')2 fragment (bivalent fragment comprising two Fab fragments linked by at least one disulfide bridge at the hinge region), a Fd fragment (consisting of the VH and CH1 domains), a Fv fragment (consisting of the VL and VH domains of a single arm of an antibody), a dAb fragment (consisting of a single variable domain fragment (VH or VL domain), a single chain Fv (scFv) comprising the two domains of a Fv fragment, VL and VH, that are fused together, eventually with a linker to make a single protein chain.

A preferred immune checkpoint inhibitor of the combination is an antibody or antibody fragment specific for an immune checkpoint inhibitor such as CTLA4, PD-1, PD-L1 or PD-L2. In particularly preferred embodiments, the immune checkpoint inhibitor is a monoclonal antibody, a fully human antibody, a chimeric antibody, a humanized antibody or fragment thereof that is capable of at least partly antagonizing PD-1, PD-L1 or PD-L2. In some embodiments, PD-1, PD-L1, and PD-L2 are human PD-1, PD-L1 and PD-L2. The amino acid sequence of an exemplary human PD-1 is shown in UniProtKB/Swiss-Prot Accession No. Q1511.6. The amino acid sequence of an exemplary human PD-L1 is shown in UniProtKB/Swiss-Prot Accession No, Q9NZQ7.1. The amino acid sequence of an exemplary human PD-L2 is shown in UniProtKB/Swiss-Prot Accession No. Q9BQ51. In a related embodiment, CTLA4 is human CTLA4. The amino acid sequence of an exemplary human CTLA4 (precursor) shown in Swiss-Prot Accession No. P16410.

Monoclonal antibodies against PD-1 include, without limitation, lambrolizumab (e.g. disclosed as hPD109A and its humanized derivatives h409A11, h409A16 and h409A17 in U.S. Pat. No. 8,354,509, incorporated herein by reference), Nivolumab (Opdivo®; Bristol-Myers Squibb; code name BMS-936558) disclosed in U.S. Pat. No. 8,008,449, incorporated herein by reference, Pembrolizumab (Keytruda®) and Pidilizumab (CT-011; disclosed in Rosenblatt et al., Immunother. 34:409-418 (2011)) or an antibody comprising the heavy and light chain regions of these antibodies. Other anti-PD-1 antibodies are described in e.g. WO2004/004771, WO2004/056875, WO2006/121168, WO2008/156712, WO2009/014708, WO2009/114335, WO2013/043569 and WO2014/047350. In a related embodiment, the checkpoint inhibitor of the pharmaceutical combination is an anti-PD-1 fusion protein such as AMP-224 (composed of the extracellular domain of PD-L2 and the Fc region of human IgG1).

Monoclonal antibodies against PD-L1 include, without limitation, BMS-936559 (MDX-1105), Atezolizumab (Genentech/Roche; MPDL33280A) disclosed in U.S. Pat. No. 8,217,149, the contents of which are incorporated herein by reference, Durvalumab (AstraZeneca/MedImmune; MEDI4736) disclosed in U.S. Pat. No. 8,779,108, incorporated herein by reference, MIH1 (Affymetrix obtainable via eBioscience (16.5983.82)) and Avelumab (MSB0010718C; Merck KGaA) or an antibody comprising the heavy and light chain variable regions of any of these antibodies. In a related embodiment, the immune checkpoint inhibitor is an anti-PD-L1 fusion protein such as the PD-L2-Fc fusion protein known as AMP-224 (disclosed in Mkritchyan M., et al., J. Immunol., 189:2338-47 (2010).

In preferred embodiments, the replication-competent oncolytic adenovirus of the combination comprises an Ad5 nucleic acid backbone engineered to comprise a heterologous nucleic acid encoding an OX40 ligand polypeptide and/or a heterologous nucleic acid encoding a GITR ligand polypeptide operably linked to a suitable promoter and the immune checkpoint inhibitor of the combination is an antibody that inhibits CTLA4, PD1, PD-L1 or PD-L2. In a particularly preferred embodiment, the replication competent oncolytic adenovirus of the combination comprises a Delta-24 or Delta-24-RGD adenovirus nucleic acid backbone engineered to comprise a heterologous nucleic acid encoding OX40 ligand and/or a heterologous nucleic acid encoding GITR ligand polypeptide operably linked to a suitable promoter and the checkpoint inhibitor of the combination is a monoclonal antibody that inhibits PD1, PD-L1 and/or PD-L2.

In some aspects, a combination therapy for treating and/or preventing cancer and or for treating and/or preventing metastases is provided comprising co-administering to a subject in need thereof an effective amount of (i) a replication-competent adenovirus engineered to comprise a heterologous nucleic acid encoding an inhibitor of an immune checkpoint protein selected from the group consisting of: CTLA4, PD-1, PD-L1, PD-L2, B7-H3, B7-H4, TIM3, GAL9, LAG3, VISTA, KIR, and BMA; and (ii) an agonist of an immune cell stimulatory receptor selected from the group consisting of: CD28, OX40, GITR, 4-1BB, HVEM, ICOS, CD27, CD40, CD226, CRTAM, DR3, LTBR, TACI, BAFFR and BCMA.

The immune cell stimulatory receptor agonist may be an antibody or antibody fragment that specifically binds to an immune cell stimulatory receptor or may be a ligand of an immune cell stimulatory receptor. In preferred embodiments, the immune cell stimulatory receptor agonist is an antibody, antibody fragment or ligand that specifically binds to OX40 or GITR.

In some embodiments, the replication-competent oncolytic adenovirus of the combination comprises an Ad5 nucleic acid backbone engineered to comprise heterologous nucleic acid encoding a PD-1, PD-L2 and/or a CTLA4 inhibitor operably linked in each case to a suitable promoter and the immune cell stimulatory receptor agonist of the combination is an antibody, antibody fragment or ligand that specifically binds to OX40 or GITR. In a particularly preferred embodiment, the replication competent oncolytic adenovirus of the combination comprises a Delta-24 or Delta-24-RGD adenovirus nucleic acid backbone engineered to comprise heterologous nucleic acid encoding a PD-1, PD-L1, PD-L2 and/or CTLA4 monoclonal antibody or antibody fragment, in each case operably linked to a suitable promoter, and the checkpoint inhibitor of the combination is an antibody, antibody fragment or ligand that specifically binds to OX40 or GITR.

In some embodiments, a replication competent oncolytic virus as described above further expresses one or more tumor associated antigens. In some aspects, the replication competent oncolytic virus comprises an Ad5 nucleic acid backbone and comprises heterologous nucleic acid sequence encoding a tumor-associated antigen, wherein the tumor-associated antigen is displayed on the surface (capsid) of the adenovirus. In other aspects, the replication competent oncolytic virus comprises an Ad5 nucleic acid backbone and comprises heterologous nucleic acid sequence encoding a tumor-associated antigen, wherein the tumor-associated antigen is expressed in an infected target (i.e. cancer) cell. In related embodiments, a pharmaceutical composition comprising such a replication competent oncolytic virus is provided as well as the use of such a composition in the treatment and/or prevention of cancer and/or the prevention and/or treatment of metastases. In a preferred embodiment, the replication competent oncolytic virus comprises a Delta-24 or Delta-24-RGD adenovirus nucleic acid backbone engineered to comprise heterologous nucleic acid sequence encoding a tumor-associated antigen or immunogenic epitope thereof (e.g. EGFR or NY-ESO-1) and (i) heterologous nucleic acid sequence(s) encoding a PD-1 and/or PD-L1 and/or CTLA4 inhibitor and optionally (ii) heterologous nucleic acid sequence(s) encoding an OX40 ligand polypeptide and/or a GITR ligand polypeptide.

Any replication competent oncolytic virus described herein may be administered to a subject in combination with any other replication competent oncolytic virus described herein to treat and/or prevent cancer and/or treat and/or prevent metastases. Thus in some embodiments, a method for treating and/or preventing cancer and/or treating and/or preventing metastases is provided comprising administering to a subject in need of such treatment effective amounts of (i) a first oncolytic virus expressing a first immune checkpoint inhibitor and (ii) a second oncolytic virus expressing a second immune checkpoint inhibitor. In yet other embodiments, a method for treating and/or preventing cancer and/or treating and/or preventing metastasis is provided comprising administering to a subject in need of such treatment effective amounts of (i) a first oncolytic virus expressing an immune checkpoint inhibitor and (ii) a second oncolytic virus expressing an immune cell stimulatory agonist. Preferably, the first and second oncolytic viruses are adenoviruses each comprising a modified Ad5 nucleic acid backbone.

In other embodiments, an oncolytic virus (e.g. adenovirus) comprising heterologous nucleic acid encoding an inhibitor of an immune checkpoint protein and optionally comprising heterologous nucleic acid encoding an immune cell co-stimulatory receptor agonist is co-administered to a subject with an additional cancer therapeutic in order to treat and/or prevent cancer and or treat and/or prevent metastases in the subject. In one embodiment, a replication competent adenovirus expressing an antibody or antibody fragment that specifically binds PD-1, PD-11, PD-L2 or CTLA4 is co-administered to a subject with an effective amount of an IDO inhibitor. Suitable IDO inhibitors include, without limitation, NLG919 (NewLink Genetics), molecular analogues of tryptophan such as D-1-methyl-tryptophan (NLG8189), and hydroxyamidine inhibitors such as hydroxyamidine 1 (epacadostat; INCB024360).

I. Replication Competent Oncolytic Viruses

Replication-competent oncolytic viruses expressing one or more immune cell stimulatory receptor agonists according to the present invention include any naturally occurring (e.g. from a "field source") or modified replication-competent oncolytic virus. The oncolytic virus, in addition to expressing one or more immune cell stimulatory receptor agonists, may for example, be modified to increase selectivity of the virus for cancer cells.

Replication-competent oncolytic viruses according to the invention include, but are not limited to, oncolytic viruses that are a member in the family of myoviridae, siphoviridae, podpviridae, teciviridae, corticoviridae, plastnaviridae, lipothrixviridae, fuselloviridae, poxyiridae, iridoviridae, phycodnaviridae, baculoviridae, herpesviridae, adnoviridae, papovaviridae, polydnaviridae, inoviridaeonicroviridae, geminiviridae, circoviridae, parvoviridae, hepadnaviridae, retroviridae, cyctoviridae, reoviridae, birnaviridae, paramyxoviridae, rhabdoviridae, filoviridae, orthoinyxoviridae, bunyaviridae, arenaviridae, leviviridae, picornaviridae, sequiviridae, comoviridae, potyviridae, caliciviridae, astroviridae, nodaviridae, tetraviridae, tombusviridae, coronaviridae, glaviviridae, togaviridae, and barnaviridae.

Particular examples of replication-competent oncolytic viruses for use in the practice of the invention include adenovirus, retrovirus, reovirus, rhabdovirus, Newcastle Disease virus (NDV), polyoma virus, vaccinia virus, herpes simplex virus, picornavirus, coxsackie virus and parvovirus In one embodiment, the replication-competent oncolytic virus is a rhabdovirus selected from a vesicular stomatitis virus (VSV) and a Maraba strain, optionally modified to increase cancer selectivity. Such modifications include, but are not limited to, mutations in the matrix (M) gene that render the virus susceptible to a host IFN response.

In another embodiment, the replication-competent oncolytic virus is a vaccinia virus, non-limiting examples of which include Western Reserve, Wyeth, and Copenhagen strains optionally modified to increase cancer selectivity. Such modifications include, but are not limited to: nonfunctional thymidine kinase gene, nonfunctional vaccinia growth factor gene, and non-functional type 1 interferon-binding gene.

In another aspect, the replication competent oncolytic virus is selected from a herpes simplex virus (HSV) virus (such as HSV-1 or HSV1716) and a Newcastle disease virus (NDV).

Adenoviruses are particularly preferred replication-competent oncolytic viruses.

Adenovirus (Ad) is a large (~36 kb) DNA virus that infects humans, but which display a broad host range. Physically, adenovirus is an icosahedral virus containing a double-stranded, linear DNA genome. There are approximately 50 serotypes of human adenovirus, which are divided into six families based on molecular, immunological, and functional criteria. By adulthood, virtually every human has been infected with the more common adenovirus serotypes, the major effect being cold-like symptoms.

Adenoviral infection of host cells results in adenoviral DNA being maintained episomally, which reduces the potential genotoxicity associated with integrating vectors. Also, adenoviruses are structurally stable, and no genome rearrangement has been detected after extensive amplification. Adenovirus can infect virtually most epithelial cells regardless of their cell cycle stage. So far, adenoviral infection appears to be linked only to mild disease such as acute respiratory disease in humans Members of any of the 57 human adenovirus serotypes (HAdV-1 to 57) may incorporate heterologous nucleic acid encoding an immune cell stimulatory receptor agonist according to the invention. Human Ad5 is well characterized genetically and biochemically (GenBank M73260; AC_000008). Thus, in a preferred embodiment, the oncolytic adenovirus is a replication competent Ad5 serotype or a hybrid serotype comprising an Ad5 component. The adenovirus may be a wild type strain but is preferably genetically modified to enhance tumor selectivity, for example by attenuating the ability of the virus to replicate within normal quiescent cells without affecting the ability of the virus to replicate in tumor cells. Non-limiting examples of replication competent oncolytic adenoviruses encompassed by the present invention include Delta-24, Delta-24-RGD, ICOVIR-5, ICOVIR-7, ONYX-015, ColoAd1, H101 and AD5/3-D24-GMCSF. Onyx-015 is a hybrid of virus serotype Ad2 and Ad5 with deletions in the E1B-55K and E3B regions to enhance cancer selectivity. H101 is a modified version of Onyx-015. ICOVIR-5 and ICOVIR-7 comprise an Rb-binding site deletion of E1A and a replacement of the E1A promoter by an E2F promoter. ColoAd1 is a chimeric Add11p/Ad3 serotype. AD5/3-D24-CFMCSF (CGTG-102) is a serotype 5/3 capsid-modified adenovirus encoding GM-CSF (the Ad5 capsid protein knob is replaced with a knob domain from serotype 3).

In one particularly preferred embodiment, the replication competent oncolytic adenovirus is Delta-24 or Delta-24-RGD. Delta-24 is described in U.S. Patent Application Publication Nos. 20030138405, and 20060147420, each of which are incorporated herein by reference. The Delta-24 adenovirus is derived from adenovirus type 5 (Ad-5) and contains a 24-base-pair deletion within the CR2 portion of the E1A gene that encompasses the area responsible for binding Rb protein (nucleotides 923-946) corresponding to amino acids 122-129 in the encoded E1A protein (Fueyo J et al., Oncogene, 19:2-12 (2000)). Delta-24-RGD further comprises an insertion of the RGD-4C sequence (which hinds strongly to αvβ3 and αvβ5 integrins) into the H1 loop of the fiber knob protein (Pasqualini R. et al., Nat Biotechnol, 15:542-546 (1997)). The E1A deletion increases the selectivity of the virus for cancer cells; the RGD-4C sequence increases the infectivity of the virus in gliomas.

Oncolytic adenoviruses injected into a tumor induce cell death and release of new adenovirus progeny that, by infecting the neighbor cells, generates a treatment wave that, if not halted, may lead to the total destruction of the tumor. Significant antitumor effects of Delta-24 have been shown in cell culture systems and in malignant glioma xenograft models. Delta-24-RGD has shown surprising anti-tumor effects in a Phase 1 clinical trial and is currently the subject of additional clinical trials. Although lysis of tumor cells is the main anti-cancer mechanism proposed for Delta-24-RGD oncolytic adenovirus, data from the Phase 1 clinical trial in patients with recurrent glioma and other observations indicate that the direct oncolytic effect may be enhanced by the adenovirus-mediated trigger of anti-tumor immune response. Thus, approximately 10% of patients treated with Delta-24-RGD showed an infiltration of the tumor by immune cells that in certain cases is quite massive. In these cases, representing a small minority of those treated, a Th1-predominant immune response was observed that appears to correlate with optimum anti-tumor response. Aspects of the current invention are directed at enhancing this anti-tumor efficacy in the majority of patients. The replication-competent oncolytic adenovirus of the invention is designed to accomplish this by (i) enhancing the Th1 immune response against both adenoviral and tumor antigens and (2) reversing the immune suppressive environment of the tumor. Administration of oncolytic adenovirus of the invention leads to the activation of the population of lymphocytes that recognize cancer cells with or without virus infection and accordingly provides an enhanced and prolonged antitumor effect that persists even after the virus is eradicated. Oncolytic adenovirus of the invention provides a significant advantage compared to separately administering the adenovirus and the checkpoint inhibitor by localizing the inhibitor to the site of the tumor thereby reducing unwanted side-effects accompanying systemic administration of the inhibitor.

The infectious cycle of the adenovirus takes place in 2 steps: the early phase which precedes initiation of the replication of the adenoviral genome, and which permits production of the regulatory proteins and proteins involved in the replication and transcription of the viral DNA, and the late phase which leads to the synthesis of the structural proteins. The early genes are distributed in 4 regions that are dispersed in the adenoviral genome, designated E1 to E4 (E denotes "early"). The early regions comprise at least-six transcription units, each of which possesses its own promoter. The expression of the early genes is itself regulated, some genes being expressed before others. Three regions, E1, E2, and E4 are essential to replication of the virus. Thus, if an adenovirus is defective for one of these functions this protein will have to be supplied in trans, or the virus cannot replicate.

The E1 early region is located at the 5' end of the adenoviral genome, and contains 2 viral transcription units, E1A and E1B. This region encodes proteins that participate very early in the viral cycle and are essential to the expression of almost all the other genes of the adenovirus. In particular, the E1A transcription unit codes for a protein that transactivates the transcription of the other viral genes, inducing transcription from the promoters of the E1B, E2A, E2B, E3, E4 regions and the late genes. Typically, exogenous sequences are integrated in place of all or part of the E3 region The adenovirus enters the permissive host cell via a cell surface receptor, and it is then internalized. The viral DNA associated with certain viral proteins needed for the first steps of the replication cycle enters the nucleus of the infected cells, where transcription is initiated. Replication of the adenoviral DNA takes place in the nucleus of the infected cells and does not require cell replication. New viral particles or virions are assembled after which they are released from the infected cells, and can infect other permissive cells.

The adenovirus is an attractive delivery system. Embodiments of the invention can utilize a suspension cell process with average yields of $1 \times 10^{16}$ viral particles per batch. The process can be free of or essentially free of protein, serum, and animal derived components making it suitable for a broad range of both prophylactic and therapeutic vaccine products.

Several factors favor the use of oncolytic adenoviruses for the treatment of brain tumors. First, gliomas are typically localized, and therefore an efficient local approach should be enough to cure the disease. Second, gliomas harbor several populations of cells expressing different genetic abnormalities. Thus, the spectrum of tumors sensitive to the transfer of a single gene to cancer cells may be limited. Third, replication competent adenoviruses can infect and destroy cancer cells that are arrested in G0. Since gliomas invariably include non-cycling cells, this property is important. Finally, the p16-Rb pathway is abnormal in the majority of gliomas, thus making Delta-24 adenovirus particularly effective for treating these tumors, although the loss of the retinoblastoma tumor suppressor gene function has been associated with the causes of various types of tumors and is not limited to treatment of gliomas.

If an adenovirus has been mutated so that it is conditionally replicative (replication-competent under certain conditions), a helper cell may be required for viral replication. When required, helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, for example Vero cells or other monkey embryonic mesenchymal or epithelial cells. In certain aspects a helper cell line is 293. Various methods of culturing host and helper cells may be found in the art, for example Racher et al., 1995.

In certain aspects, the oncolytic adenovirus is replication-competent in cells with a mutant Rb pathway. After transfection, adenoviral plaques are isolated from the agarose-overlaid cells and the viral particles are expanded for analysis. For detailed protocols the skilled artisan is referred to Graham and Prevac, 1991.

Alternative technologies for the generation of adenovirus vectors include utilization of the bacterial artificial chromosome (BAC) system, in vivo bacterial recombination in a recA+bacterial strain utilizing two plasmids containing complementary adenoviral sequences, and the yeast artificial chromosome (YAC) system (PCT publications 95/27071 and 96/33280, which are incorporated herein by reference).

Adenovirus is easy to grow and manipulate and exhibits broad host range in vitro and in vivo. This group of viruses can be obtained in high titers (e.g., greater than $10^9$ plaque forming units (pfu) per ml), and they are highly infective. The life cycle of adenovirus does not require integration into the host cell genome.

Modifications of oncolytic adenovirus described herein may be made to improve the ability of the oncolytic adenovirus to treat cancer. Such modifications of an oncolytic adenovirus have been described by Jiang et al. (Curr Gene Ther. 2009 October 9(5):422-427), see also U.S. Patent Application No. 20060147420, each of which are incorporated herein by reference.

The absence or the presence of low levels of the coxsackievirus and adenovirus receptor (CAR) on several tumor types can limit the efficacy of the oncolytic adenovirus. Various peptide motifs may be added to the fiber knob, for instance an RGD motif (RGD sequences mimic the normal ligands of cell surface integrins), Tat motif, polylysine motif, NGR motif, CTT motif, CNGRL motif, CPRECES motif or a strept-tag motif (Rouslahti and Rajotte, 2000). A motif can be inserted into the HI loop of the adenovirus fiber protein. Modifying the capsid allows CAR independent target cell infection. This allows higher replication, more efficient infection, and increased lysis of tumor cells (Suzuki et al., 2001, incorporated herein by reference). Peptide sequences that bind specific human glioma receptors such as EGFR or uPR may also be added. Specific receptors found exclusively or preferentially on the surface of cancer cells may be used as a target for adenoviral binding and infection, such as EGFRvIII.

II. Expression Cassettes

In certain embodiments of the present invention, the methods set fourth herein involve nucleic acid sequences encoding an immune cell stimulatory receptor agonist wherein the nucleic acid is comprised in an "expression cassette." The term "expression cassette" is meant to include any type of genetic construct containing a nucleic acid coding for a gene product in which part or all of the nucleic acid encoding sequence is capable of being transcribed.

Promoters and Enhancers—In order for the expression cassette to effect expression of a transcript, the nucleic acid encoding gene will be under the transcriptional control of a promoter. A "promoter" is a control sequence that is a region of a nucleic acid sequence at which initiation and rate of transcription are controlled. The phrases "operatively positioned," "operatively linked," "under control," and "under transcriptional control" mean that a promoter is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence.

Any promoter known to those of ordinary skill in the art that would be active in a cell in a subject is contemplated as a promoter that can be applied in the methods and compositions of the present invention. One of ordinary skill in the art would be familiar with the numerous types of promoters that can be applied in the present methods and compositions. In certain embodiments, for example, the promoter is a constitutive promoter, an inducible promoter, or a repressible promoter. The promoter can also be a tissue selective promoter. A tissue selective promoter is defined herein to refer to any promoter that is relatively more active in certain tissue types compared to other tissue types. Examples of promoters include the CMV promoter.

The promoter will be one that is active in a cell and expression from the promoter results in the presentation of an antigenic determinant to a subject's immune system. For instance, where the cell is an epithelial cell the promoter used in the embodiment will be one having activity in that particular cell type.

A promoter may be one naturally associated with a gene or sequence, as may be obtained by isolating the 5'-non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™ (see U.S. Pat. Nos. 4,683,202 and 5,928,906, each incorporated herein by reference).

Naturally, it will be important to employ a promoter and/or enhancer that effectively directs the expression of the DNA segment in the cell type, organelle, and organism chosen for expression. Those of skill in the art of molecular biology generally understand the use of promoters, enhancers, and cell type combinations for protein expression, for example, see Sambrook et al. (2001), incorporated herein by reference. The promoter may be heterologous or endogenous.

The particular promoter that is employed to control the expression of the nucleic acid of interest is not believed to be critical, so long as it is capable of expressing the polynucleotide in the targeted cell at sufficient levels. Thus, where a human cell is targeted, it is preferable to position the polynucleotide coding region adjacent to and under the control of a promoter that is capable of being expressed in a human cell. Generally speaking, such a promoter might include either a human or viral promoter.

In various embodiments, the human cytomegalovirus (CMV) immediate early gene promoter, the SV40 early promoter and the Rous sarcoma virus long terminal repeat can be used. The use of other viral or mammalian cellular or bacterial phage promoters, which are well-known in the art to achieve expression of polynucleotides, is contemplated as well, provided that the levels of expression are sufficient to produce an immune response.

Additional examples of promoters/elements that may be employed, in the context of the present invention include the following, which is not intended to be exhaustive of all the possible promoter and enhancer elements, but, merely, to be exemplary thereof: Immunoglobulin Heavy Chain; Immunoglobulin Light Chain; T Cell Receptor; HLA DQ α and/or DQ β; β Interferon; Interleukin-2; Interleukin-2 Receptor; MHC Class II; MHC Class II HLA-DRα; β-Actin; Muscle Creatine Kinase (MCK); Prealbumin (Transthyretin); Elastase I; Metallothionein (MTII); Collagenase; Albumin; α-Fetoprotein; t-Globin; β-Globin; c-fos; c-HA-ras; Insulin; Neural Cell Adhesion Molecule (NCAM); α1-Antitrypsin; H2B (TH2B) Histone; Mouse and/or Type I Collagen; Glucose-Regulated Proteins (GRP94 and GRP78); Rat Growth Hormone; Human Serum Amyloid A (SAA); Troponin I (TN I); Platelet-Derived Growth Factor (PDGF); Duchenne Muscular Dystrophy; SV40; Polyoma; Retroviruses; Papilloma Virus; Hepatitis B Virus; Human Immunodeficiency Virus; Cytomegalovirus (CMV); and Gibbon Ape Leukemia Virus.

Enhancers were originally detected as genetic elements that increased transcription from a promoter located at a distant position on the same molecule of DNA. The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have very similar modular organization. Additionally, any promoter/enhancer combination (as per the Eukaryotic Promoter Data Base EPDB) could also be used to drive expression of a gene. Further selection of a promoter that is regulated in response to specific physiologic signals can permit inducible expression of a construct. For example, with the polynucleotide under the control of the human PAI-1 promoter, expression is inducible by tumor necrosis factor. Examples of inducible elements, which are regions of a nucleic acid sequence that can be activated in response to a specific stimulus include (Element/Inducer); MT II/Phorbol Ester (TFA) or Heavy metals; MMTV (mouse mammary tumor virus)/Glucocorticoids; β-Interferon/poly(rI)x or poly(rc); Adenovirus 5 E2/E1A; Collagenase/Phorbol Ester (TPA); Stromelysin/Phorbol Ester (TPA); SV40/Phorbol Ester (TPA); Murine MX Gene/Interferon, Newcastle Disease Virus; GRP78 Gene/A23187; α-2-Macroglobulin/IL-6; Vimentin/Serum; MHC Class I Gene H-2κb/Interferon; HSP70/E1A, SV40 Large T Antigen; Proliferin/Phorbol Ester-TPA; Tumor Necrosis Factor/PMA; and Thyroid Stimulating Hormone a Gene/Thyroid Hormone.

Initiation Signals—A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals.

IRES—In certain embodiments of the invention, the use of internal ribosome entry sites (IRES) elements are used to create multigene, or polycistronic, messages. IRES elements are able to bypass the ribosome scanning model of 5' methylated Cap dependent translation and begin translation at internal sites. IRES elements from two members of the picornavirus family (polio and encephalomyocarditis) have been described, as well an IRES from a mammalian message. IRES elements can be linked to heterologous open reading frames, Multiple open reading frames can be transcribed together, each separated by an IRES, creating polycistronic messages (see U.S. Pat. Nos. 5,925,565 and 5,935,819).

Multiple Cloning Sites—Expression cassettes can include a multiple cloning site (MCS), which is a nucleic acid region that contains multiple restriction enzyme sites, any of which can be used in conjunction with standard recombinant technology to digest the vector.

Polyadenylation Signals—In expression, one will typically include a polyadenylation signal to effect proper polyadenylation of the transcript. The nature of the polyadenylation signal is not believed to be crucial to the successful practice of the invention, and/or any such sequence may be employed. Preferred embodiments include the SV40 polyadenylation signal and/or the bovine growth hormone polyadenylation signal, convenient and/or known to function well in various target cells. Also contemplated as an element of the expression cassette is a transcriptional termination site. These elements can serve to enhance message levels and/or to minimize read through from the cassette into other sequences.

Other Expression Cassette Components—In certain embodiments of the invention, cells infected by the adenoviral vector may be identified in vitro by including a reporter gene in the expression vector. Generally, a selectable reporter is one that confers a property that allows for selection. A positive selectable reporter is one in which the presence of the reporter gene allows for its selection, while a negative selectable reporter is one in which its presence prevents its selection. An example of a positive selectable marker is a drug resistance marker (genes that confer resistance to neomycin, puromycin, hygrornycin, DHFR, GPT, zeocin and histidinol). Other types of reporters include screenable reporters such as GFP.

Embodiments of the invention can use current adenoviral platform technologies in the preparation of an adenoviral nucleic acid comprising a heterologous nucleic acid segment that encodes a tumor associated antigen. Aspects of the adenoviral vaccine construction include inserting genetic material into an adenoviral vector and confirming the construct through characterization and sequencing of the nucleic acid, virus and virus product. The adenoviral vaccine is then put through a series of feasibilities studies designed to assess scalability.

III. Cancer

The methods of the present invention may be used to treat cancers. Specific examples of cancer types include but are not limited to glioma, melanoma, metastases, adenocarcinoma, thyoma, lymphoma, sarcoma, lung cancer, liver cancer, colon cancer, non Hodgkins lymphoma, Hodgkins lymphoma, leukemias, uterine cancer, breast cancer, prostate cancer, ovarian cancer, cervical cancer, bladder cancer, kidney cancer, pancreatic cancer, head and neck cancer, colorectal cancer, renal cancer, thyroid cancer, hepatocellular carcinoma and the like. The term "glioma" refers to a tumor originating in the neuroglia of the brain or spinal cord. Gliomas are derived from the glial cell types such as astrocytes and oligodendrocytes, thus gliomas include astrocytomas and oligodendrogliomas, as well as anaplastic gliomas, glioblastomas, and ependymomas. Astrocytomas and ependymomas can occur in all areas of the brain and spinal cord in both children and adults. Oligodendrogliomas typically occur in the cerebral hemispheres of adults. Gliomas account for 75% of brain tumors in pediatrics and 45% of brain tumors in adults. Other brain tumors are meningiomas, ependymomas, pineal region tumors, choroid plexus tumors, neuroepithelial tumors, embryonal tumors, peripheral neuroblastic tumors, tumors of cranial nerves, tumors of the hemopoietic system, germ cell tumors, and tumors of the stellar region. The methods of the present invention may be used to treat any cancer of the brain.

The term melanoma includes, but is not limited to, melanomas, metastatic melanomas, melanomas derived from either melanocytes or melanocytes related nevus cells, melanocarcinomas, melanoepitheliomas, melanosarcomas, melanoma in situ, superficial spreading melanoma, nodular melanoma, lentigo maligna melanoma, acral lentiginous melanoma, invasive melanoma or familial atypical mole and melanoma (FAM-M) syndrome. Such melanomas in mammals may be caused by, chromosomal abnormalities, degenerative growth and developmental disorders, mitogenic agents, ultraviolet radiation (UV), viral infections, inappropriate tissue expression of a gene, alterations in expression of a gene, and presentation on a cell, or carcinogenic agents.

The aforementioned cancers can be assessed or treated by methods of the present invention. In the case of cancer, a gene encoding an antigen associated with the cancer (e.g. a tumor associated antigen (TAA)) may be incorporated into the recombinant virus genome or portion thereof along with nucleic acid encoding one or more immune cell stimulatory receptor agonist molecules. The antigen associated with the cancer may be expressed on the surface of a cancer cell, may be secreted or may be an internal antigen.

In preferred embodiments, a pharmaceutical combination comprising (a) a replication competent oncolytic adenovirus comprising an adenovirus serotype 5 (Ad5) nucleic acid backbone or a hybrid nucleic acid backbone comprising an Ad5 component and a heterologous nucleic acid sequence encoding an OX40 agonist inserted in a nonessential region of the adenovirus genome, wherein the inserted heterologous nucleic acid sequence is under the control of a sequence permitting expression of OX40 agonist in a cell and (b) one or more PD-L1 and/or PD-1 inhibitors are co-administered to treat and/or prevent a glioma in a subject. Preferably, the subject is a human. In related embodiments, the human has undergone one or more previous treatments for the glioma and/or the glioma is refractory to one or more therapies and/or the glioma is recurrent following post-surgical resection and/or temozolomide therapy.

IV. Pharmaceutical Compositions

The present invention also provides a pharmaceutical composition comprising any composition of the present invention, and a pharmaceutically acceptable carrier. The present invention also provides a vaccine composition comprising any composition of the present invention. The vaccine composition may further comprise at least one adjuvant.

The present invention also provides a method of stimulating an anti-tumor immune response in a subject, comprising administering to a subject a composition of the present invention.

According to the present invention, an adenovirus expressing one or more immune checkpoint inhibitors and optionally one or more immune cell stimulatory receptor agonists and optionally one or more tumor associated antigens is administered to a subject to induce an immune response for therapeutic or prophylatic purposes. Thus, in certain embodiments, the expression construct is formulated in a composition that is suitable for this purpose. The phrases "pharmaceutically" or "pharmacologically acceptable" refer to compositions that do not produce adverse, allergic, or other untoward reactions when administered to an animal or a human. As used herein, "pharmaceutically acceptable carrier" includes any and all solvents, carriers, dispersion media, coatings, antibacterial and antifungal agents, isotonic and absorption delaying agents, and the like. The use of such media and agents for pharmaceutically active substances is well known in the art. Except insofar as any conventional media or agent is incompatible with the expression constructs of the present invention, its use in therapeutic compositions is contemplated. Supplementary active ingredients also can be incorporated into the compositions. For example, the supplementary active ingredient may be an additional immunogenic agent.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. If needed, various antibacterial an antifungal agents can be used, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating compounds in the required amount in the appropriate solvent with various of the other ingredients enumerated above, as required, followed by filter sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum drying and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically or prophylactically effective. For parenteral administration in an aqueous solution, the solution should be suitably buffered if necessary and the liquid diluent first rendered isotonic with sufficient saline or glucose. These particular aqueous solutions are especially suitable for intravascular and intratumoral administration. In this connection, sterile aqueous media, which can be employed will be known to those of skill in the art in light of the present disclosure.

Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by the FDA.

Dosage—An effective amount of the therapeutic or preventive agent is determined based on the intended goal, for example stimulation of an immune response against a tumor. Those of skill in the art are well aware of how to apply gene delivery in vivo and ex vivo situations. For viral vectors, one generally will prepare a viral vector stock. Depending on the kind of virus and the titer attainable, one will deliver at least about, at most about, or about $1\times10^4$, $1\times10^5$, $1\times10^6$, $1\times10^7$, $1\times10^8$, $1\times10^9$, $1\times10^{11}$ or $1\times10^{12}$ infectious particles, or any value or range there between, to a subject. In other aspects, adenoviruses according to the invention may be administered in a single administration or multiple administrations. The virus may be administered at dosage of $1\times10^5$ plaque forming units (PFU), $5\times10^5$ PFU, at least $1\times10^6$ PFU, $5\times10^6$ or about $5\times10^6$ PFU, $1\times10^7$, at least $1\times10^7$ PFU, $1\times10^8$ or about $1\times10^8$ PFU, at least $1\times10^8$ PFU, about or at least $5\times10^8$ PFU, $1\times10^9$ or at least $1\times10^9$ PFU, $5\times10^9$ or at least $5\times10^9$ PFU, $1\times10^{10}$ PFU or at least $1\times10^{10}$ PFU, $5\times10^{10}$ or at least $5\times10^{10}$, PFU, $1\times10^{11}$ or at least $1\times10^{11}$, $1\times10^{12}$ or at least $1\times10^{12}$, $1\times10^{13}$ or at least $1\times10^{13}$ PFU. For example, the virus may be administered at a dosage of between about $10^7$-$10^{12}$ PFU, between about $10'$-$10^{13}$ PFU, between about $10^8$-$10^{13}$ PFU, between about $10^9$-$10^{12}$ PFU, or between about $10^8$-$10^{12}$ PFU.

Replication-competent oncolytic viruses according to the invention may be administered locally or systemically. For example, without limitation, oncolytic viruses according to the invention can be administered intravascularly (intraarterially or intravenously), intratumorally, intramuscularly, intradermally, intraperitoneally, subcutaneously, orally, parenterally, intranasally, intratracheally, percutaneously, intraspinally, ocularly, or intracranially. In preferred embodiments, an adenovirus of the invention is administered intravascularly or intratumorally. In other preferred embodiments, an adenovirus of the invention is administered intracranially.

In some embodiments, replication competent oncolytic viruses according to the invention are administered by intratumoral injection into the brain. Direct injection into a tumor within the brain e.g. to treat a glioblastoma) may be accomplished e.g. by a fine catheter or cannula. Within certain embodiments of the invention, replication competent oncolytic viruses can be delivered by a microelectromechanical (MEMS) system under MRI intra-procedural guidance. Preferably, intratumoral injection into the brain is accomplished without significant reflux or back flow by using a cannula such as Alcyone Lifesciences' Alcyone MEMS Cannula (AMC). Representative examples of devices are described in U.S. Pat. No. 8,992,458 and US Publication Nos. 2013-0035660, 2013-0035574, and 2013-0035560, all of which are incorporated by reference in their entirety.

Replication-competent oncolytic viruses according to the invention may also be administered in a cellular carrier. In this respect, neuronal and mesenchymal stem cells have high migratory potential yet remain confined to tumor tissue. A subpopulation of adult mesenchymal cells (bone marrow derived tumor infiltrating cells or BM-TICs) has been shown, following injection into gliomas, to infiltrate the entire tumor. Thus, oncolytic viruses according to the invention can be administered in a virus-producing neuronal or mesenchymal stem cell (e.g. BM-TIC) carrier (e.g. by injection of the carrier cell into the tumor).

Immune checkpoint protein inhibitors and immune cell stimulatory receptor agonists disclosed herein (when administered separately from the oncolytic virus as part of a pharmaceutical combination) can be administered by various routes including, for example, orally or parenterally, such as intravascularly (intravenously or intraarterially), intramuscularly, subcutaneously, intraorbitally, intracapsularly, intraperitoneally, intrarectally, intracisternally, intratumorally, intravasally, intradermally or by passive or facilitated absorption through the skin using, for example, a skin patch or transdermal iontophoresis, respectively. The immune checkpoint inhibitor or immune cell stimulatory receptor agonist also can be administered to the site of a pathologic condition, for example, intravenously or intraarterially into a blood vessel supplying a tumor. In a preferred embodiment, the immune checkpoint inhibitor or immune cell stimulatory receptor agonist is administered intratumorally.

The total amount of an immune checkpoint inhibitor or immune cell stimulator)/receptor agonist to be administered in practicing a method of the invention can be administered to a subject as a single dose, either as a bolus or by infusion over a relatively short period of time, or can be administered using a fractionated treatment protocol, in which multiple doses are administered over a prolonged period of time. One skilled in the art would know that the amount of the composition to treat a pathologic condition in a subject depends on many factors including the age and general health of the subject as well as the route of administration and the number of treatments to be administered. In view of these factors, the skilled artisan would adjust the particular dose as necessary. In general, the formulation of the composition and the routes and frequency of administration are determined, initially, using Phase I and Phase II clinical trials.

In certain embodiments, the immune checkpoint inhibitor or immune cell stimulatory agonist is administered in 0.01-0.05 mg/kg, 0.05-0.1 mg/kg, 0.1-0.2 mg/kg, 0.2-0.3 mg/kg, 0.3-0.5 mg/kg, 0.5-0.7 mg/kg, 0.7-1 mg/kg, 1-2 mg/kg, 2-3 mg/kg, 3-4 mg/kg, 4-5 mg/kg, 5-6 mg/kg, 6-7 mg/kg, 7-8 mg/kg, 8-9 mg/kg, 9-10 mg/kg, at least 10 mg/kg, or any combination thereof doses. Suitable dosages of the checkpoint inhibitor range from about 0.5 mg/kg to 25 mg/kg, preferably from about 1 mg/kg to about 20 mg/kg, more preferably from about 2 mg/kg to about 15 mg/kg. In certain embodiments the immune checkpoint inhibitor or immune cell stimulatory agonist is administered at least once a week, at least twice a week, at least three times a week, at least once every two weeks, or at least once every month or multiple months. In certain embodiments, the immune checkpoint inhibitor or immune cell stimulatory agonist is administered as a single dose, in two doses, in three doses, in four doses, in five doses, or in 6 or more doses. Preferably, the checkpoint inhibitor is administered intravenously (e.g. by intravenous infusion or injection) or intratumorally. By way of non-limiting example, ipilimumab may be administered by intravenous infusion at a dose of 3 mg/kg every three weeks for a total of four doses.

The quantity to be administered, both according to number of treatments and dose, depends on the subject to be treated, the state of the subject and the protection desired. Precise amounts of the therapeutic composition also depend on the judgment of the practitioner and are peculiar to each individual.

EXAMPLES

The following examples as well as the figures are included to demonstrate preferred embodiments of the invention. It should be appreciated by those of skill in the art that the techniques disclosed in the examples or figures represent techniques discovered by the inventors to function well in the practice of the invention and thus can be considered to constitute preferred modes for its practice. However, those of skill in the art should, in light of the disclosure, appreciate that many changes can be made in the specific embodiments which are disclosed and still obtain a like or similar result without departing from the spirit and scope of the invention.

Materials and Methods for Examples 1 and 2

Construction of Delta-24-RGDOX and propagation of the viruses—First, DNA coding for the RGD-4C motif was introduced via site-directed mutagenesis into the region coding for the fiber HI loop of the fiber protein using a shuttle vector, pAB26 (Microbix Biosystems, Inc.), resulting in plasmid pAB26-RGD. The mouse OX40L (mOX40L) (Origene) was subcloned into the KpnI/XbaI site in pcDNA3.1(+) (Life Technologies), and then the expression cassette for mOX40L (including the CMV promoter and bovine growth hormone polyadenylation sequences) was subcloned into the ClaI/BamHI site (in the place of the E3 region) of pAB26-RGD, producing pAB26-RGD-mOX40L. The final adenoviral genome was generated by homologous DNA recombination of pAB26-RGD-mOX40L and SwaI-linearized pVK500C.Delta-24 with a deletion of 24 by of DNA coding for the RB-binding region in the E1A gene in $E.\ coli$, BJ5183. To rescue the Delta-24-RGDOX (Delt24-RGD-mOX40L) virus, the resulting viral backbone vector was digested with PacI and then transfected into 293 cells with XtremeGENE HP DNA transfection reagent (Roche Diagnostics Corporation). Thus, the resulting virus, Delta-24-RGDOX or Delta-24-RGD-GREAT, contained the following modifications: replacement of the E3 region of the human adenovirus type 5 (hAd5) genome with mOX40L expression cassette; deletion of 24 bp in the E1A gene; and insertion of an RGD-4C motif-coding sequence in fiber gene. The modification of the viral genome was confirmed through amplification of the modified region by PCR and then sequencing the products. The viruses were propagated in A549 cells (replication-competent viruses) or 293 cells (replication-deficient AdGFP), purified by the Adenopure kit (Puresyn, Inc.), and stored at −80 C. The viral titer was assayed with the Adeno-X-Rapid Titer Kit (Clonetech) and determined as pfu/ml.

Viral replication assay—Cells were seeded at $5 \times 10^4$ cells per well in 12-well plates and infected with the virus at 10 pfu/cell. Forty-eight hours after infection, the titers of the infectious viral progenies in the whole culture were determined using the Adeno-X-Rapid Titer Kit (Clonetech) according to the manufacturer's instructions. Final viral titers were determined as PFU per milliliter.

Cell Lines and Culture Conditions—Human gliobastoma-astrocytoma U-87 MG and lung carcinoma A549 cells (ATCC), mouse glioma GL261 cells (NCI-Frederick Cancer Research Tumor Repository), GL261-5 cells (an isolated GL261 cell clone that resulted in longer life span of the mice than the parental GL261 cells when implanted intracranially); GL261-enhanced green fluorescent protein (EGFP) cells, and GL261-OVA cells were cultured in Dulbecco's modified Eagle's medium-nutrient mixture F12 (DMEM/F12) supplemented with 10% fetal bovine serum (HyClone Laboratories, Inc.). 100 µg/ml penicillin and 100 µg/ml streptomycin, except in the GL261-OVA culture, to which 1 μg/ml puromycin (Life Technologies) was also added. Mouse melanoma cell line B16-F10 (ATCC) was maintained in RPMI 1640 medium supplemented with 10% fetal bovine serum and antibiotics. Human embryonic kidney 293 (Qbiogene, Inc.), mouse glioma CT-2A and mouse lung carcinoma CMT64 (Culture Collections, Public Health England, UK) cells were maintained in DMEM supplemented with 10% fetal bovine serum and antibiotics. Mouse primary astrocytes (AllCells, LLC) were grown in AGM Astrocyte Growth Medium (Lonza). Human glioblastoma cells (GSCs) had been established from acute cell dissociation of human glioblastoma surgical specimens. The GSCs were maintained in DMEM/F12 medium supplemented with B27 (Invitrogen), epidermal growth factor, and basis fibroblast growth factor (20 ng/ml each, Sigma-Aldrich). All cells were kept at 37 C in a humidified atmosphere containing 5% $CO_2$. All GSC lines were verified through short-tandem repeat (STR) fingerprinting. Experiments were carried out within 6 months after the cell lines were obtained from a cell bank (B16-F10 and CMT64) or after verification (GSCs).

Mice—C57BL/6 and athymic mice were provided by MD Anderson Cancer Center Mouse Resource Facility. OT-I mice (C57BL/6-Tg[TcraTcrb]1100 Mjb/J) were purchased from the Jackson Laboratory.

Animal studies—For tumor implantation, GL261 cells and its derivatives ($5 \times 10^4$ cells/mouse) cells were grafted into the caudate nucleus of the 7- to 10-week old mice using a guide-screw system. The mice with implanted tumors were randomly assigned to experimental groups. Then the viruses ($5 \times 10^7$ pfu/mouse), the OX40 agonist antibody OX86 (25 μg/mouse; provided by the Monoclonal Antibody Core Facility at MD Anderson Cancer Center), the anti-mouse PD-L1 antibody and/or rat IgG (25 μg/mouse; Bio X Cell) were injected intratumorally. For rechallenging the surviving mice, GL261-5 ($5 \times 10^4$ cells/mouse) or B16-F10 ($1 \times 10^3$ cells/mouse) cells were implanted in the same hemisphere previously implanted with the cured tumor or in the contralateral hemisphere of the mouse brain. All animal studies except the survival studies with athymic mice were conducted in C57BL/6 mice.

Flow cytometry analysis—To monitor disruption of the cell membrane (cell death) induced by the viruses, cells ($2-5 \times 10^5$) were stained with 8 μM ethidium homodimer 1 (Sigma-Aldrich) in PBS solution for 15 minutes at room temperature. To analyze cell surface protein expression, cells ($2-5 \times 10^5$) were first incubated in 100 μl primary antibody solution diluted in PBS plus 3% bovine serum albumin and 1 mM ethylenediaminetetraacetic acid. After incubation at 4 C in the dark for 30 minutes, the cells were washed once with 1 ml cold PBS. If secondary antibody was to be applied, the incubation procedure was repeated with the secondary antibody. After being washed once with PBS, cells were finally resuspended in 0.5 ml PBS. The stained cells were then analyzed using flow cytometry. The antibodies used in the studies were as follows: anti-mouse CD252 (OX40L) adenomatous polyposis coli (APC, 17-5905-80), anti-mouse CD45 APC-eFluor 780 (47-0451-82), anti-mouse CD3 fluorescein isothiocyanate (FITC, 11-0031-81), Anti-mouse CD4 eFluor® 450 (48-0041-80), anti-mouse CD8a PerCP-Cyanine 5.5 (45-0081-82), anti-human PD-L1 APC (17-5983-41), and anti-mouse CD8 APC (17-0081-81), Anti-mouse CD279 (PD-1) PE-Cyanine7 (25-9985-80), Anti-Mouse CD152 (CTLA-4) APC (17-1522-80) were obtained from eBioscience; Goat Anti-Rat IgG-FITC (ab6115) was from abeam, and anti-mouse CD252 (OX40L) purified (108802) and anti-mouse PD-L1 APC (124311) were obtained from BioLegend.

ATP and HMGB1 release analysis—The medium was collected from the cell cultures. The amount of ATP in the medium was determined with an ENLITEN ATP Assay Systemic (Promega). The HMGB1 in the medium was quantitated with an HMGB1 enzyme-linked immunosorbent assay (ELISA) kit (IBL International)

Preparation of splenocyte and CD8+ lymphocytes—Mouse spleens were collected, placed in a 100-μm cell strainer set in petri dishes with RPMI 1640 medium and then smashed through the cell strainer into the dish. The mixture in the dish was gently pipetted up and down and brought up to 5 ml/spleen. The cells were pelleted by centrifugation at 350 g for 7 minutes at room temperature and then resuspended in Red Blood Cell Lysing Buffer Hybri-Max (Sigma-Aldrich) to lyse the red blood cells, according to the manufacturer's instructions. Finally, $CD8^+$ T cells were enriched with a mouse $CD8a^+$ T cell Isolation Kit (Miltenyi Biotec, Inc.).

Preparation of brain-infiltrating lymphocytes (BILs)—BILs (from a group of 5 to 9 mouse brain hemispheres) were separated from the myelin debris using Percoll (GE Healthcare Bio-Sciences) and gradient centrifuged. Bits were then enriched using a gradient centrifuge with Lympholyte-M Cell Separation Media (Cedarlane) as instructed by the manufacturer.

Preparation of bone marrow-derived dendritic cells (mDCs)—mDCs were isolated from mouse bone marrow of femurs and tibias. After 7 days in culture, mDCs were collected and 1 μg/ml Lipopolysaccharides (Sigma-Aldrich) was added for the final 18 h of culture to induce maturation. The matured mDCs were primed with 10 μg/ml OVA (257264) peptide for one hour at 37 C.

Stimulation of immune cells—To prepare the target cells, GL261 or GL261-OVA cells were infected with virus at 100 pfu/cell. Four hours later, 100 units/ml of mouse IFNγ (Prospec Protein Specialists) was added to the culture. Forty-eight hours after viral infection, the cells were fixed with 1% paraformaldehyde. To activate immune cells, pre-fixed target cells ($2 \times 10^4$/well) were incubated with splenocytes ($5 \times 10^5$/well) or BILs ($5 \times 10^4$/well). To measure the OVA-specific T cell reaction, $CD3^{'}$ T cells ($3 \times 10^5$/well) were stimulated with pre-fixed mouse dendritic cells ($1 \times 10^5$/well) primed with the OVA 257-264 peptide (InvivoGen). Forty hours after the co-culture in a round-bottom 96-well plate, the concentration of IFNγ in the supernatant was assessed with an ELISA (mouse IFNγ DuoSet, R&D Systems).

In vitro lymphocyte cell proliferation OVA-specific CD8+ T cells were isolated from the spleens of OT-I mice and labeled with 5 μM carboxyfluorescein succinimidyl ester (CFSE, Life Technologies) for 5 minutes. The labeled T-cells ($1 \times 10^5$/well) were stimulated with target cells ($5 \times 10^4$/well) in a round-bottom 96-well plate. Four days later, the cells were stained with anti-mouse CD8a allophycocyanin (APC) and analyzed with flow cytometry for green fluorescence (CFSE amount) in CD8+ cells. Proliferating cells were defined as those exhibiting lower CFSE amount than unstimulated cells.

Histopathological analysis of the brain tumors—The brains were isolated from the euthanized mice, fixed with formalin, and embedded in paraffin wax. The whole-mount coronal sections of the brain were stained with hematoxylin and eosin following conventional procedures.

Statistics—In quantitative studies of cultured cells, each group consisted of triplicate samples. Each study was repeated at least once. The difference between groups was evaluated using a 2-tailed Student's t-test. The animal survival curves were plotted according to the Kaplan-Meier method. Survival rates in the different treatment groups were compared using the log-rank test. The synergistic interactions of the agents in survival studies were analyzed based on the normal survival model using the function survreg in R, and a residual plot was used to examine the parametric assumption of the model. P values <0.05 were considered significant.

Example 1

Construction and Characterization of Delta-24-RGDOX

Delta-24-RGDOX, a replication-competent adenovirus that includes an expression cassette for mouse OX40L (mOX40L) on Delta-24-RGD backbone was generated. See FIG. 1. The mouse OX40L expression cassette with CMV promoter replaced the E3 region of human adenovirus type 5 genome. A 24-bp sequence within the CR2 portion of the E1A gene (corresponding to amino acids 122-129 in the encoded E1A protein) responsible for binding Rb protein was deleted. A RGD-4C integrin-binding motif coding sequence was inserted in the HI-loop of the fiber protein. The resulting replication competent adenovirus comprising an expression cassette for mouse OX40L was termed Delta-24-RGDOX (or D24-RGDOX)

Figure 2A:
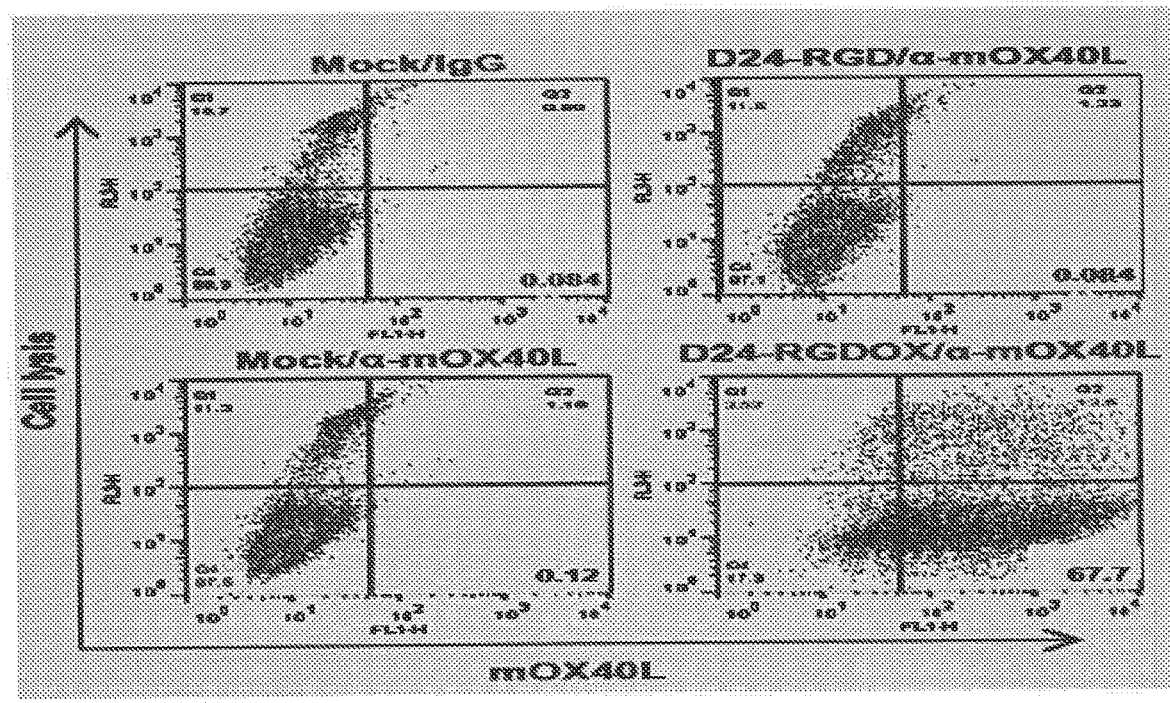
FIGS. 2A-2B. Expression of mouse OX4L (mOX40L) by Delta-24-RGD-OX40L (referred to as D24-REDOX in the figure) in mouse glioma GL261 cells (FIG. 2A) and human U-87 MG glioma cells (FIG. 2B). Cells were infected with Delta-24-RGD or Delta-24-REDOX at 50 pfu/cell (GL261) or 10 pfu/cell (11-87 MG). 48 hours later, the cells were harvested and mOX40L expression (α-mOX40L antibody (1:100 dilution)) and cell death (cells with broken membrane stained with ethidium homodimer-1 (8 μM)) were analyzed with flow cytometry. Representative dot plots for each analysis is shown. The numbers at the lower right corners indicate percentage of live cells expressing mOX40L on their cell membrane, FIG. 3. Expression of mouse OX40L (mOX40L) by D24-RGDOX on mouse melanoma B16 cells. Methods were the same as described for FIGS. 2A-2B.
Figure 2B:
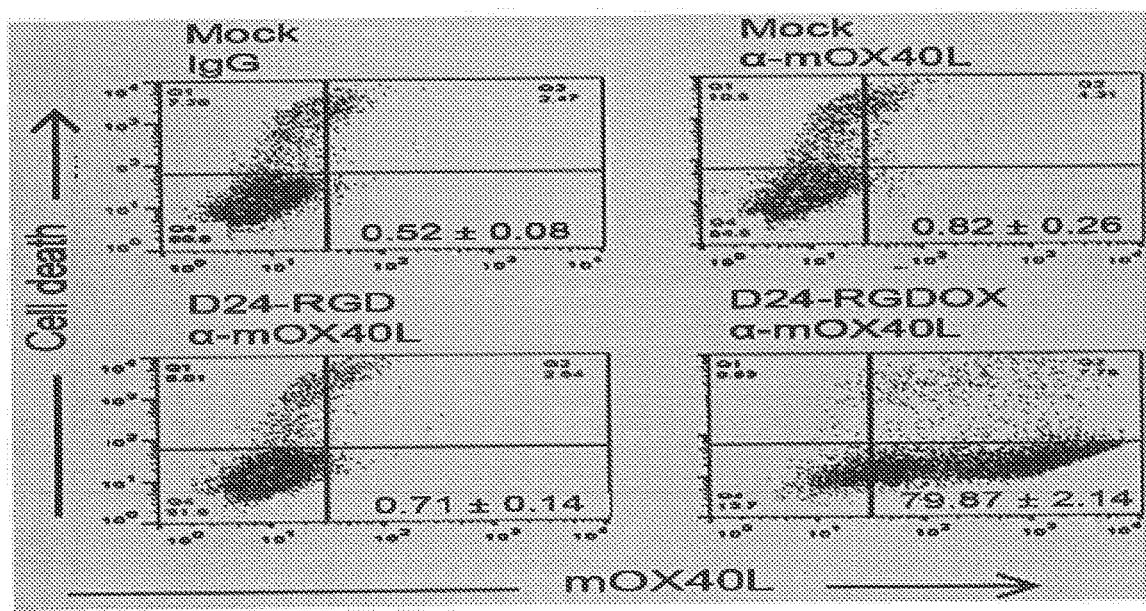
Figure 3:
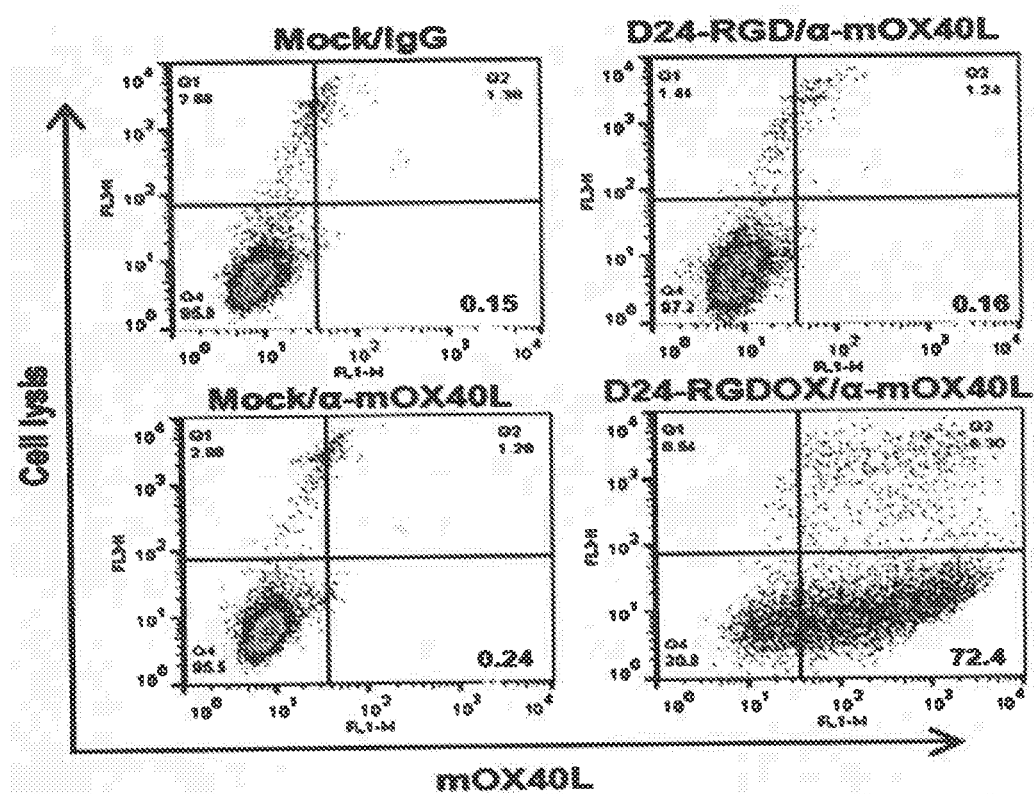
Figure 14A:
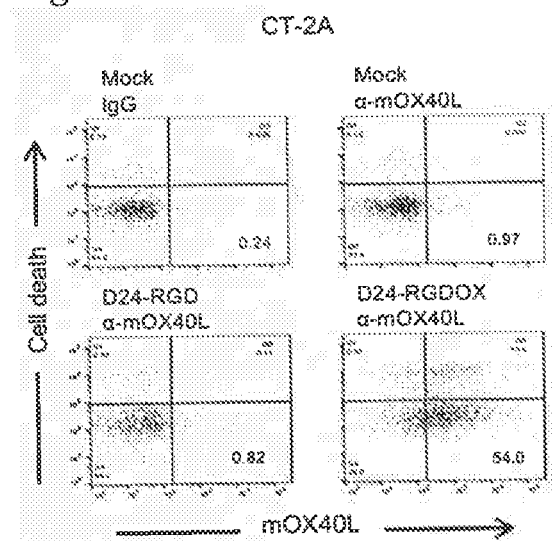
FIGS. 14A-D. Expression of mOX40L by Delta-24-RGDOX. Cells were infected with the indicated viruses (50 pfu/cell for CT-2A and B16, 20 pfu/cell for GSC20, 25 pfu/cell for CMT64). 48 hours later, cells were stained with anti-mOX40L-APC or anti-mOX40L antibody and then an FITC-labeled secondary goat anti-rat IgG antibody. The cell membrane disruption (cell death) was monitored using ethidium homodimer-1 staining. The stained cells were analyzed using flow cytometry. The numbers at the lower right corners are the percentages of the CT-2A (FIG. 14A), GSC20 (FIG. 14B), B16-F10 (FIG. 14C) and CMT64 (FIG. 14D) cells expressing mOX40L. Shown are representative results from two experiments. D24-RGD: Delta-24-RGD; D24-RGDOX: Delta-24-RGDOX.
Figure 14B:
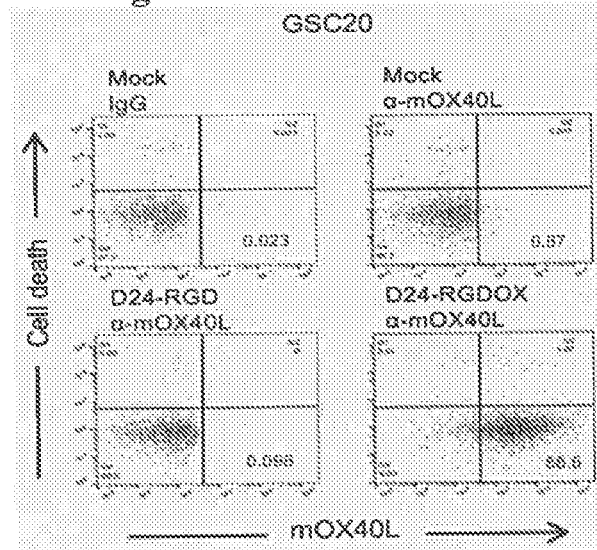
Figure 14C:
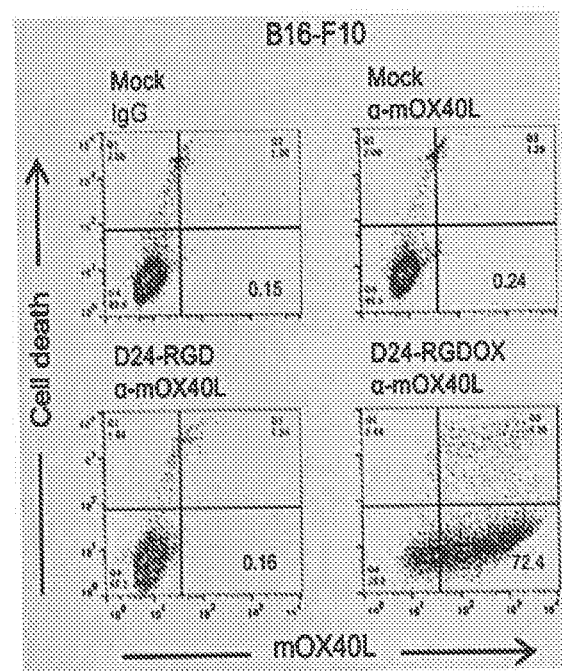
Figure 14D:
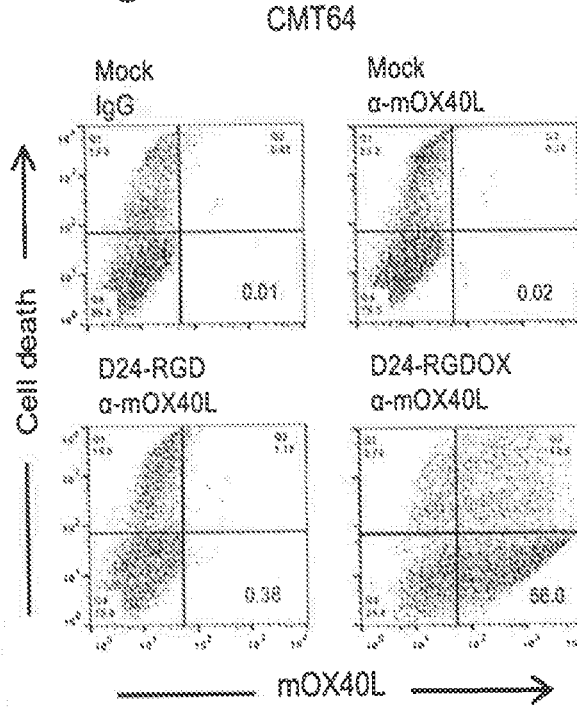

Expression of mouse OX40L (mOX40L) by D24-RGDOX on GL261 (mouse glioma) and mouse melanoma B16 cells was assessed. G-L261 or B16 cells were infected with D24-REDOX at 50 pfu/cell. 48 hours later, the cells were stained with α-mOX40L antibody (1:100 dilution) (eBioscience, San Diego, Calif.) and then with FITC-labeled secondary antibody goat anti-rat IG (1:100 dilution) (Santa Cruz Biotechnology). The cell membrane integrity was monitored with ethidium homodimer –1 staining (8 μM) (Sigma-Aldrich, St. Louis, Mo.). The stained cells were analyzed with flow cytometry. The numbers at the lower right corners of FIGS. 2A, 2B and 3 indicate the percentage of mouse GL261, human U-87 MG and mouse melanoma 1316 cells expressing mOX40L. D24-RGDOX expressed OX40L efficiently on both GL261 cells, U-87 MG cells and melanoma B16 cells. Expression of mOX40L by D24-RGDOX was also confirmed in CT-2A mouse astrocytoma cells (FIG. 14A), GSC20 cells (human mesenchymal glioma cells) (FIG. 14B) and CMT64 cells (mouse lung carcinoma cells) (FIG. 14D) using the same methodology. Thus, D24-RGDOX efficiently expresses mOX40L on the cell membranes of living cultured mouse and human cancer cells.

Figure 4A:
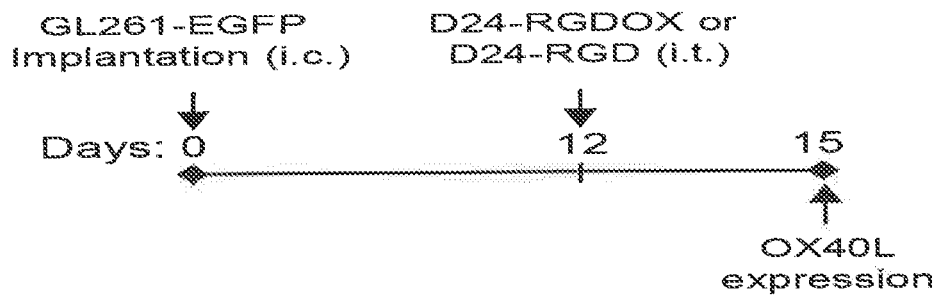
FIGS. 4A-C. In vivo expression of mouse OX40L (mOX40L) by D24-RGDOX on xenograft cells from virus-treated tumors. GL261-EGFP cells ($5 \times 10^4$ cells) were injected intracranially in C57BL/6 mice and 12 days later D24-RGDOX or D24-RGD were injected intratumorally ($5 \times 10^7$ pfu), 3 days after injection, hemispheres with tumors from treated mice (3 mice per group) were harvested and cells were dissociated and stained with rat monoclonal α-mOX40L-APC antibody (1:100 dilution) according to the scheme depicted at FIG. 4A. The stained cells were analyzed with flow cytometry. Tumor cells were gated for EGFP$^+$. A representative dot plot is shown at FIG. 4B. The numbers at the upper right corners indicate the percentage of tumor cells expressing mOX40L. The same data is represented graphically at FIG. 4C. The results from two separate experiments are shown.
Figure 4B:
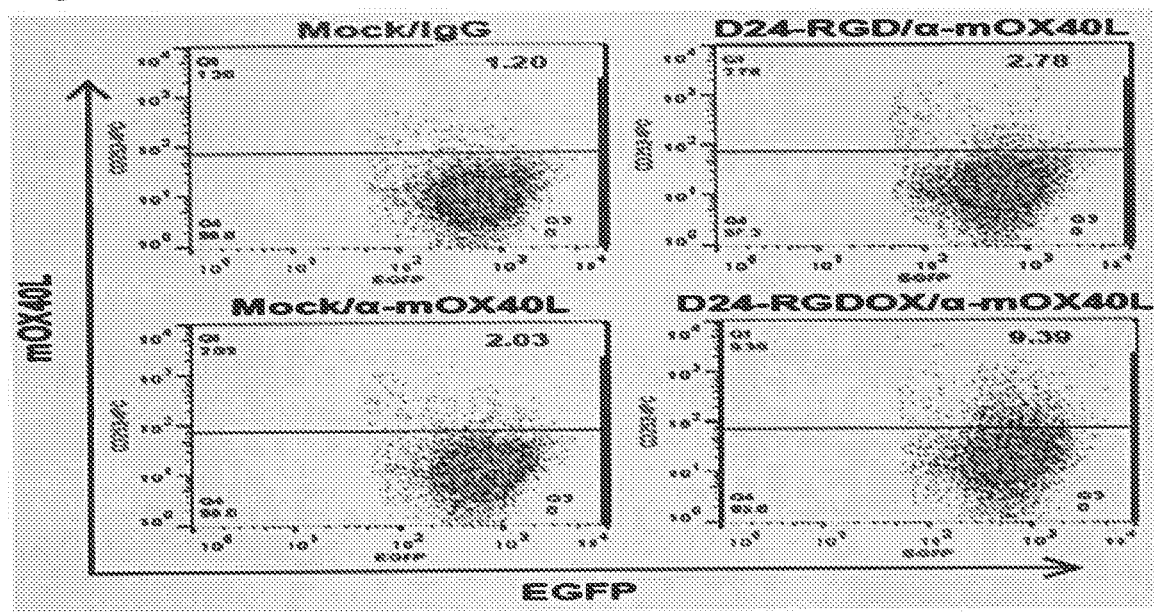
Figure 4C:
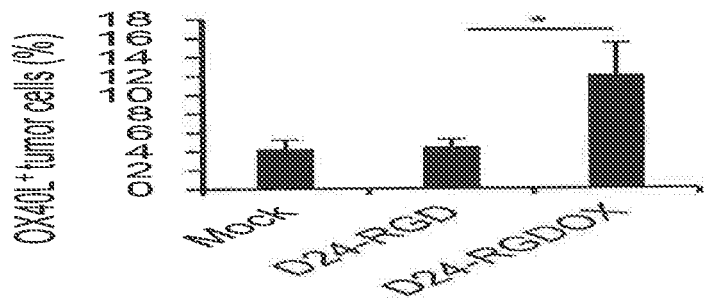

In in vivo settings, expression of mOX40L in cells from gliomas arising from intracranial injection of GL261 cells stably-expressing enhanced green fluorescent protein (GL261-EGFP, Figure) was assessed (FIG. 4A). GL261-EGFP (Enhanced Green Fluorescent Protein-expressing GL261) tumor cells ($5 \times 10^4$ cells) were injected intracranially in C57BL/6 mice. 12 days later, D24-RGDOX was injected intratumorally ($5 \times 10^7$ pfu). Three days after the injection, the tumors were harvested and dissociated with ACCUMAX cell detachment solution (EMD Millipore, Billerica, Mass.) The cells were then stained with rat monoclonal α-mOX40L APC antibody (1:40) (eBioscience). The stained cells were analyzed with flow cytometry. Tumor cells were gated as EGFP positive. The numbers at the upper right corners of FIG. 4B indicate the percentage of the tumor cells expressing mOX40L. These in vivo data demonstrate expression of OX40L in about 9-11% of the xenograft cells seventy-two hours after injection with D24-RGDOX (FIG. 4C).

Figure 5:
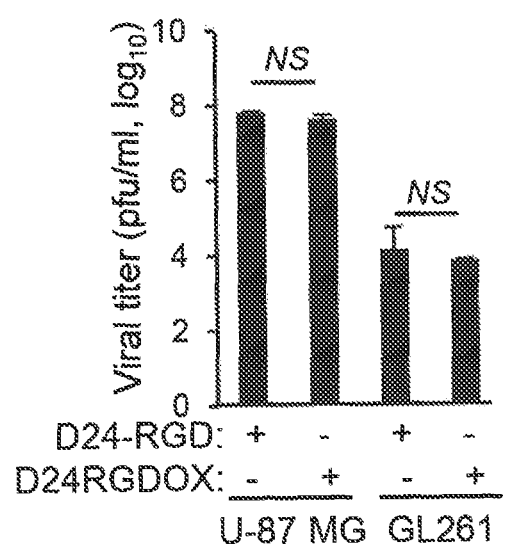
FIG. 5. Replication of D24-RGD and D24-RGDOX in U-87 MG and GL261 cells. Cells were infected with the viruses at 10 pfu/cell. 48 hours after infection, infectious viral progeny were titered and final viral titers determined as pfu/ml.

Replication of D24-RGD and D24-RGDOX in U87 MG (human primary glioblastoma cell line with epithelial morphology; American Type Culture Collection, Manassas, Va.) or GL261 cells was tested. Cells were seeded at a density of $5 \times 10^4$ cells/well in 12-well plates and infected with the viruses at 10 pfu/cell. Forty-eight hours after infection, the infectious viral progeny were titered using the ADENO-X Rapid Titer Kit (Clontech, Mountain View, Calif.) according to manufacturer's instructions. Final viral titers were determined as pfu/ml and are shown in FIG. 5 as mean±SD of three independent measurements. The replication of the two viruses was compared using the Student's T-test (two-sided). D24-RGDOX was shown to replicate as efficiently as its parental virus D24-RGD in human glioma U-87 MG cells whereas both viruses replicate very poorly in GL261 cells. Thus, the antitumoral effects described herein with the mouse glioma model significantly under-represent the expected antitumoral effects of the virus (expressing OX40L) in humans. The modification of the viral genome did not significantly change its replication capability in human U-87 MG glioma cells (P=0.05) and mouse GL261 glioma cells (P=0.44).

Figure 6A:
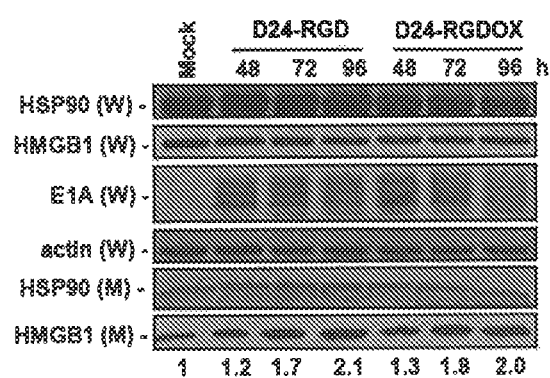
FIGS. 6A-E, Immunogenic cell death induced by Delta-24-RGDOX.
Figure 6B:
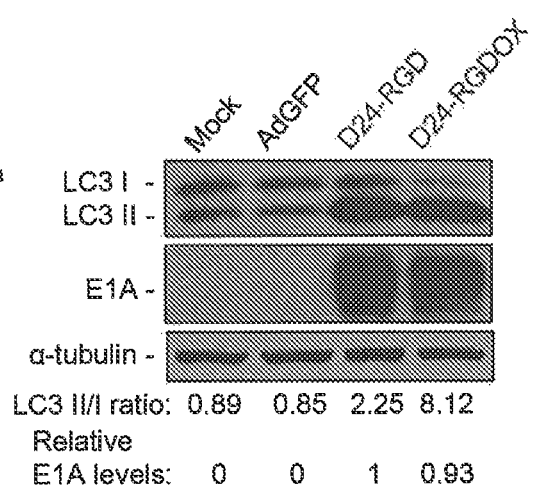
Figure 6C:
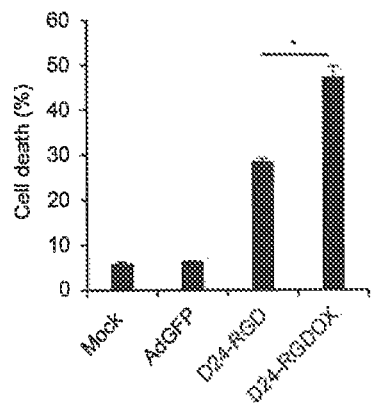
Figure 6D:
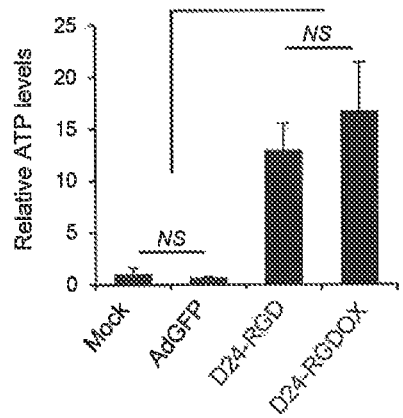
Figure 6E:
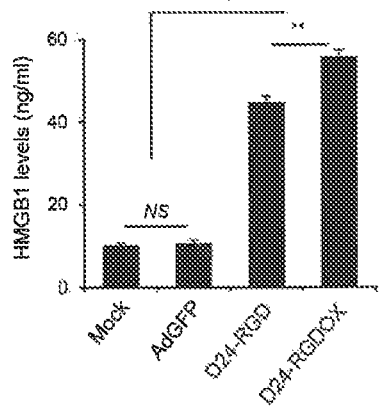

Adenoviruses potently induce autophagic cell death. This capability was found in Delta-24-RGDOX, which induced autophagy and cell lysis more robustly than Delta-24-RGD, as shown by the increased LCII/I ratio (FIG. 6B) and rupture in cell membranes (FIG. 6C). It was reported that this type of cell death attracted immune cells via the extracellular release of damage- (or danger-)associated molecular pattern (DAMP) molecules such as adenosine triphosphate (ATP) and the high-mobility group protein B1 (HMGB1). The ability of D-24-RGD and D24-RGDOX to induce HSP90 and high mobility group protein B1 (HMGB1) secretion was assessed. GL261 cells were infected with the viruses at 200 pfu/cell. 24 hours later, the concentration of the FBS was changed from 10% to 2%. Culture medium (M) and whole cell lysates (W) were collected at the time points indicated in FIG. 6A. Culture medium was concentrated 10-fold with Protein Concentrators (9K MWCO, Thermo Scientific). Then HSP90 and HMGB1 expression levels were analyzed with immunoblotting. Briefly, equal amounts of proteins from whole-cell lysates or 40 μl/lane concentrated medium were separated with 4-20% gradient sodium dodecyl sulfate-polyacrylamide gel electrophoresis, electrophoretically transferred to nitrocellulose membranes, and the membranes were probed with rabbit polyclonal anti-HSP90 and anti-HMGB1 (1:1000 dilution) (Cell Signaling Technology, Beverly, Mass.), goat polyclonal anti-actin (1:1000 dilution) (Santa Cruz Biotechnology, Santa Cruz, Calif.). The protein-antibody complexes were visualized using the enhanced chemiluminescence western blotting detection system (Amersham Pharmacia Biotech, Piscataway, N.J.). Actin was used as a loading control for whole cell lysates. The numbers at the bottom of FIG. 6A indicate the relative HMGB1 levels secreted to the medium. See also FIG. 6E. Despite the low replication efficiency of the virus in GL261 cells, both viruses induced the release of ATP and HMGB1, which are the prototype of endogenous damage-associated molecular pattern (DAMP) molecules that trigger inflammation and immunity during immunogenic cell death. Delta-24-RGDOX more efficiently induced HMGB1 release than Delta-24-RGD (25% increment). Replication deficient virus AdCMV-GFP did not induce the release of ATP and HMGB1 from the infected cells. Thus, both Delta-24-RGD and Delta-24-RGDOX induced release of ATP and HMGB1 from infected cells (FIGS. 6D and 6E) and Delta-24-RGDOX mediated HMGB1 release more efficiently than Delta-24-RGD (FIG. 6E) most likely because of its enhanced ability to induce autophagy and lysis in infected cells (FIGS. 6B and 6C).

Example 2

Enhanced Therapeutic Effect Induced by D24-RGDOX

Figure 8A:
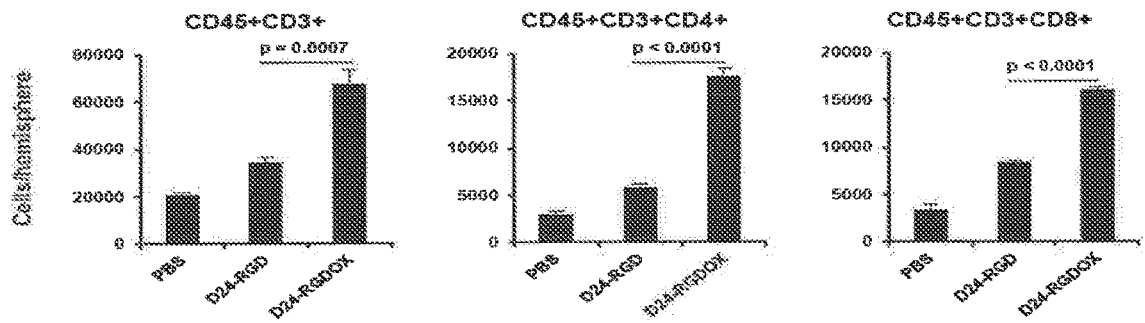
FIGS. 8A-D. Anti-glioma immunity mediated by Delta-24-RGDOX.
Figure 8B:
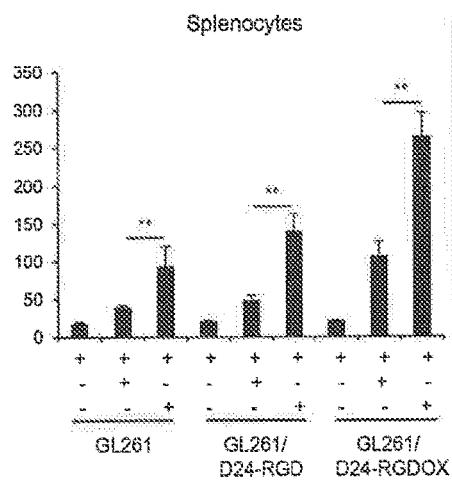
Figure 8C:
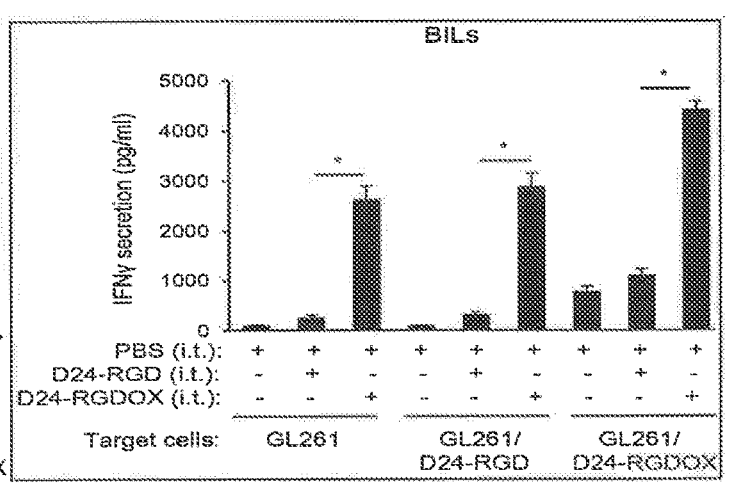
Figure 8D:
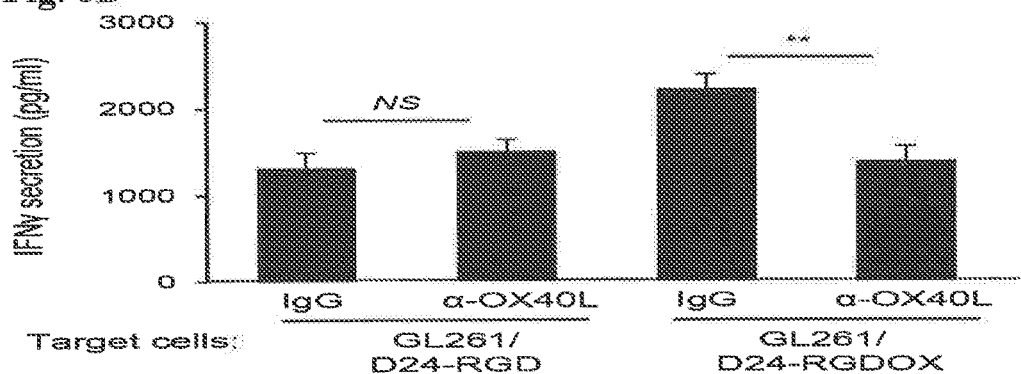

During viral therapy, the DAMPs induced by intratumoral viral injections attract immune cells to the tumor site and elicit an innate immune response that results in the development of adaptive anti-tumor immunity. To test this, a syngeneic GL-261-057BL16 immunocompetent glioma model with tumor infiltrating OX40+ T cells was used, GL261 cells ($5 \times 10^4$ cells) were injected intracranially in C57BL/6 mice (day 0) and the mice received 3 intratumoral viral injections at days 6, 8 and 10 after tumor implantation to partially compensate for the viruses' relatively poor replication in GL261 cells. On day 14, brain-infiltrated leukocytes (from group of 9 mice) were first separated from myelin debris with Percoll (GE Healthcare Bio-Sciences, Pittsburgh, Pa.) gradient centrifuge and were directly used for flow cytometry analysis. The antibodies used were as follows: anti-mouse CD45 APC-EFLUOR 780 (1:200 dilution), anti-mouse CD3 FITC (1:200 dilution), anti-mouse CD8a PerCP-Cyanine5.5 (1:80 dilution) (eBioscience), BRILLIANT VIOLET 650 anti-mouse CD4 antibody (1:100 dilution) (BioLegend, San Diego, Calif.). In mice injected with either Delta-24-RGD or Delta-24-RGDOX, more T lymphocytes ($CD45^+/CD3^+$), T helper cells ($CD45^+/CD3^+/CD4^+$), and cytotoxic T cells ($CD45^+/CD3^+/CD8^+$) were present at the tumor site than in mice with phosphate-buffered saline (PBS). Moreover, significantly more of these cells were present in Delta-24-RGDOX- than in Delta-24-RGD-injected mice (FIG. 8A). Next, the anti-tumor activity of the immune cells was examined by assessing the IFNγ secretion by these cells when they were stimulated with tumor cells. Thus, the brain-infiltrating lymphocytes (BILs) from the hemispheres with Delta-24-RGDOX-injected tumor showed significantly higher activity against the tumor cells with or without viral infection than the BILs from the Delta-24-RGD- or PBS-treated groups (FIG. 8B), indicating that Delta-24-RGDOX mediated a stronger antitumor immune response at the tumor site than did Delta-24-RGD. The same effect was observed in splenocytes from the treatment groups (FIG. 8C) although the increment of the activation induced by Delta-24-RGDOX is not as great as in BILs. Consistent with the co-stimulating activity of OX40L, Delta-24-REDOX-infected tumor cells triggered higher activation of BILs than Delta-24-RGD-infected cells (FIG. 8B) and this effect was blocked by the presence of the OX40L antibody (FIG. 8D).

Figure 9A:
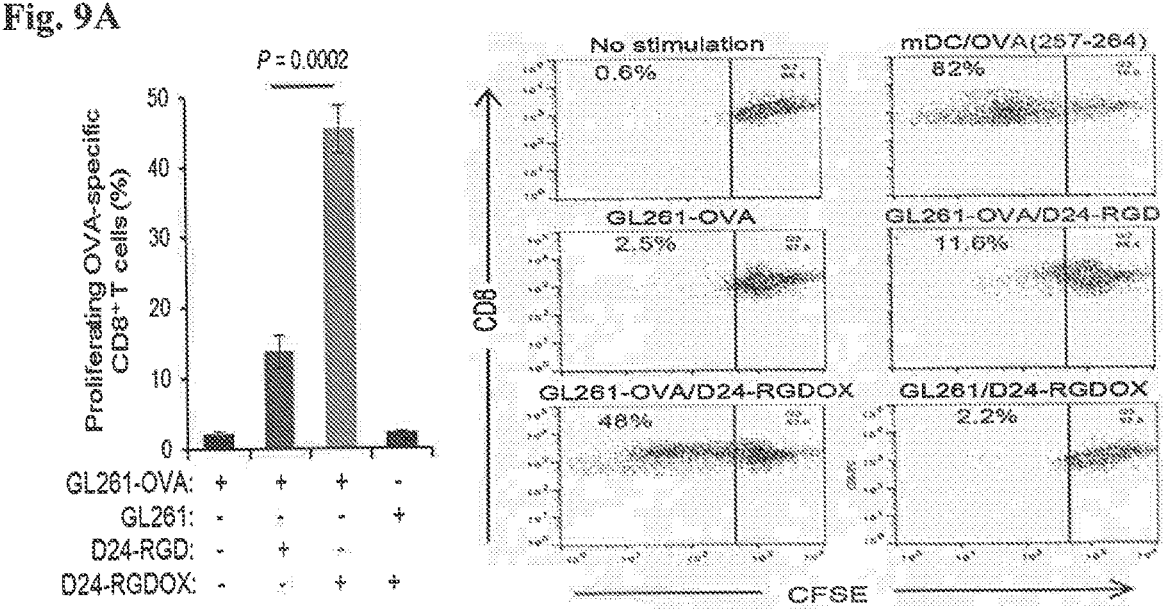
FIGS. 9A-C. Tumor-specific immunity mediated by Delta-24-RGDOX.
Figure 9B:
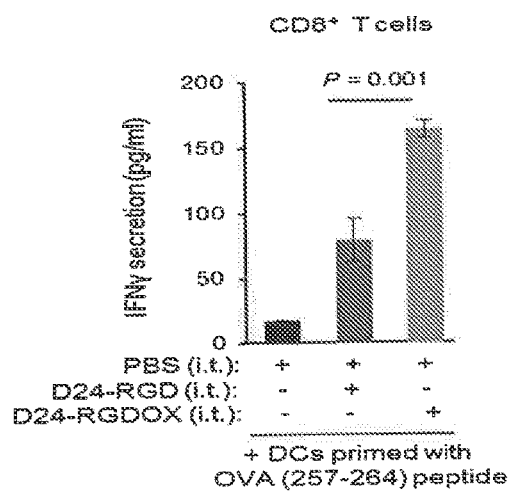

To further demonstrate the capability of Delta 24-RGDOX to stimulate immunity against tumor associated antigens (TAAs), ovalbumin protein (OVA) was used as a model antigen. Using CFSE staining to track T cell proliferation, it was found that GL261-OVA cells infected with Delta-24-REDOX induced proliferation of OVA-specific CD8+ T cells more robustly than GL261-OVA cells infected with Delta-24-RGD (FIG. 9A). Accordingly, CD8+ T cells isolated from mice harboring GL261-OVA gliomas that had been treated with Delta-24-RGDOX displayed significantly higher activity against mouse dendritic cells primed with an OVA (257-264) peptide than cells from mice treated with Delta-24-RGD (FIG. 9B). This virus-elicited immunity against OVA correlated with the tumor cell-stimulated activation of splenocytes from virus-treated glioma-bearing mice, which was not observed when the splenocytes were co-cultured with primary mouse astrocytes (FIG. 9C), indicating that Delta-24-RGDOX-elicited immunity is tumor specific. Thus, Delta-24-RGDOX is more potent than Delta-24-RGD to enhance in situ expansion of cancer-specific T-cell populations within a tumor.

Figure 7A:
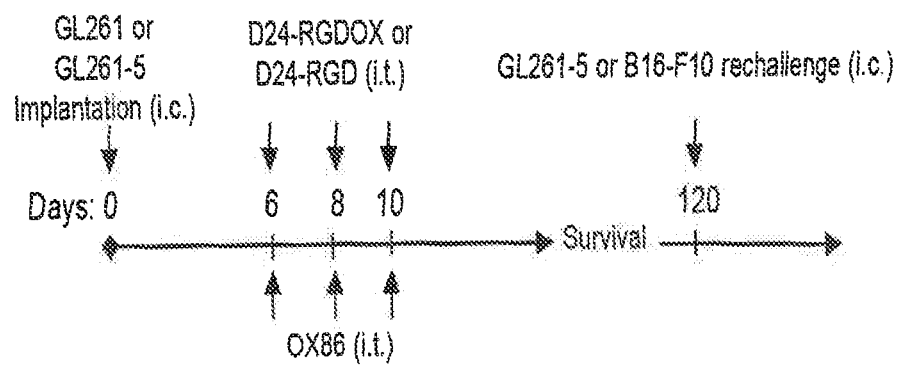
FIGS. 7A-G. D24-RGDOX enhances anti-glioma activity.
Figure 7B:
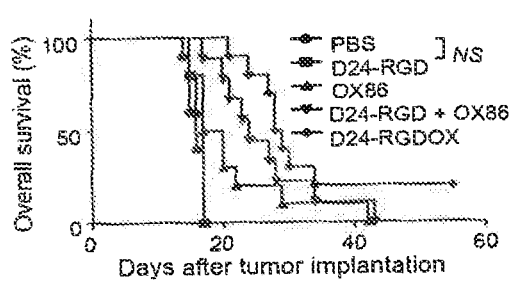

Next, survival studies were performed using the GL261-C57BL/6 mouse glioma model to evaluate the anti-glioma activity of Delta-24-RGDOX (FIG. 7A). The results revealed that GL261 tumors treated with three doses of Delta-24-RGD alone did not affect survival compared to PBS (median survivals: 17 vs. 16 days, FIG. 7B). However, the addition of the OX40 agonist antibody OX86 significantly prolonged survival (median survivals 24 vs. 17 days, FIG. 7B). The treatment of tumors with Delta-24-REDOX further extended the median survival (median survival: 28.5 vs. 17 days) producing a 20% long-term survival rate (FIG. 7B).

Figure 7C:
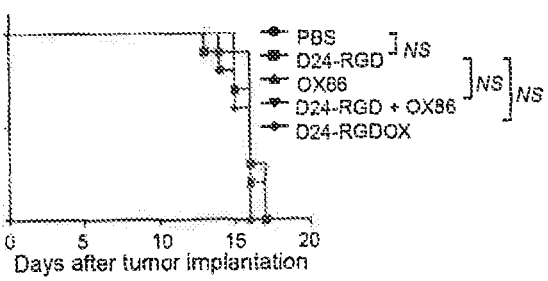

To determine the effect of anticancer immunity on survival rates, the treatments were repeated in immunodeficient mice athymic mice. Neither Delta-24-RGDOX nor the combination of Delta-24-RGD with OX86 showed a therapeutic benefit when compared to PBS (median survival 16 vs. 16 days, FIG. 7C). The dramatic difference in the therapeutic effect of Delta-24-RGDOX between immunocompetent and immunodeficient mice underscores the essential role played by virotherapy-induced immunity.

Figure 7D:
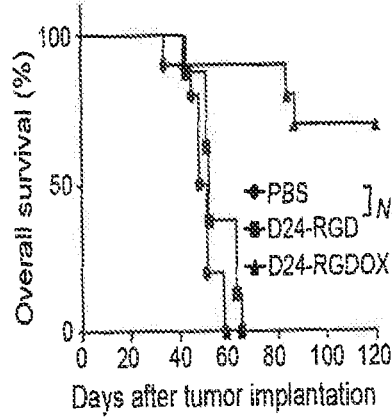
Figure 9C:
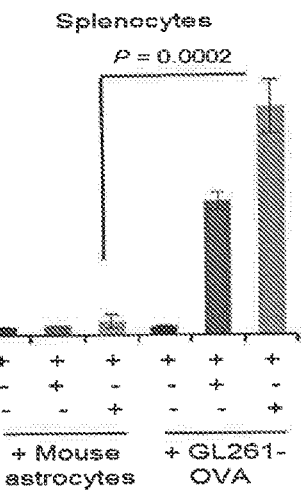
Figure 10:
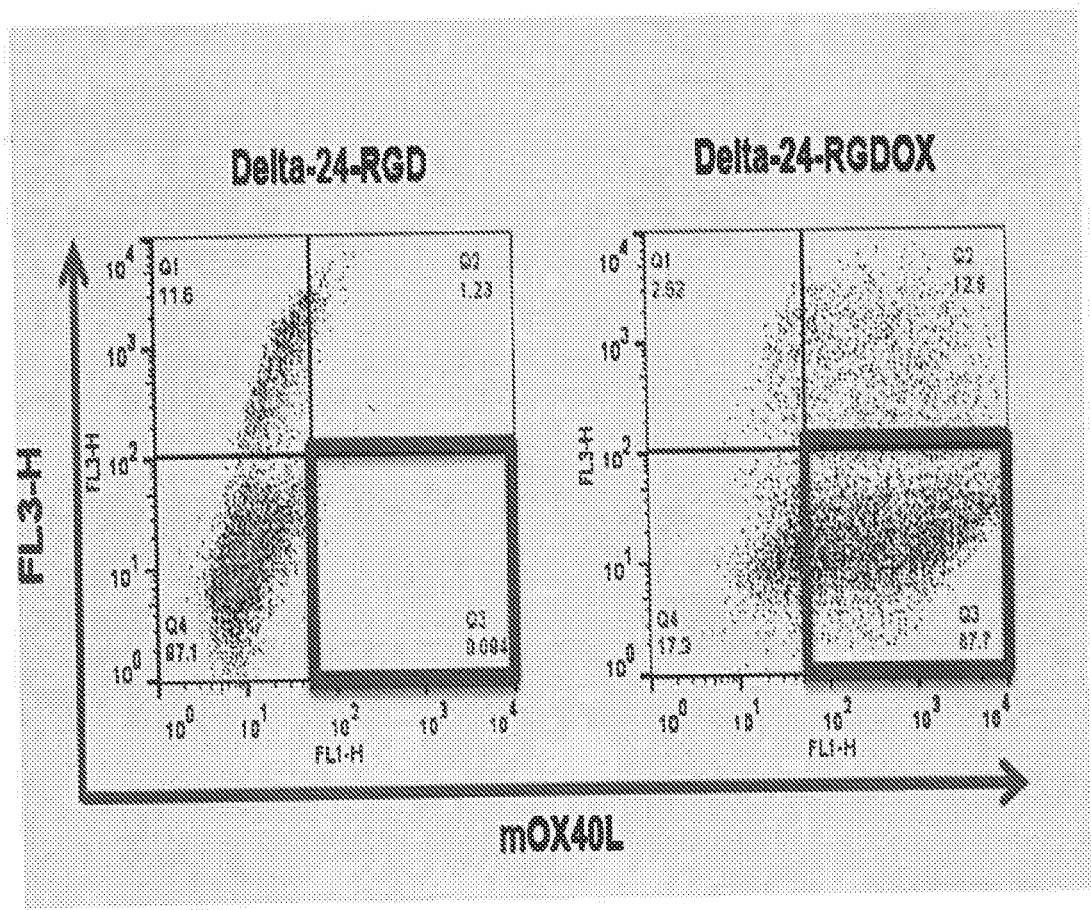
FIG. 10. Graph demonstrating expression of OX40L in infected host cells following infection with Delta-24-RGD-OX40L (referred to as Delta-24-REDOX in the figure). HeLa (human cervical epidermal adenocarcinoma) cells were infected with Delta-24-RGD-OX40L, constructed according to FIG. 1, at a multiplicity of infection (m.o.i.) of 50 pfu/cell. Briefly, viral stocks were diluted to the indicated m.o.i., added to cell monolayers (0.5 mL/60 mm dish or 5 mL/100 mm dish) and incubated at 37 C for 30 minutes with brief agitation every 5 minutes. After this, the necessary amount of culture medium was added and the cells were returned to the incubator for the prescribed time. 48 hours after infection with the virus, cells were stained with antibody against mOX40L and the percentage of cells expressing mOX40L analyzed by flow cytometry. Dead cells were excluded using EthD-1 staining (FL3-H), mOX40L positive cells are illustrated in the lower right quadrant. The images illustrate that cells infected with Delta-24-RGD-OX40L express OX40L.
Figure 11:
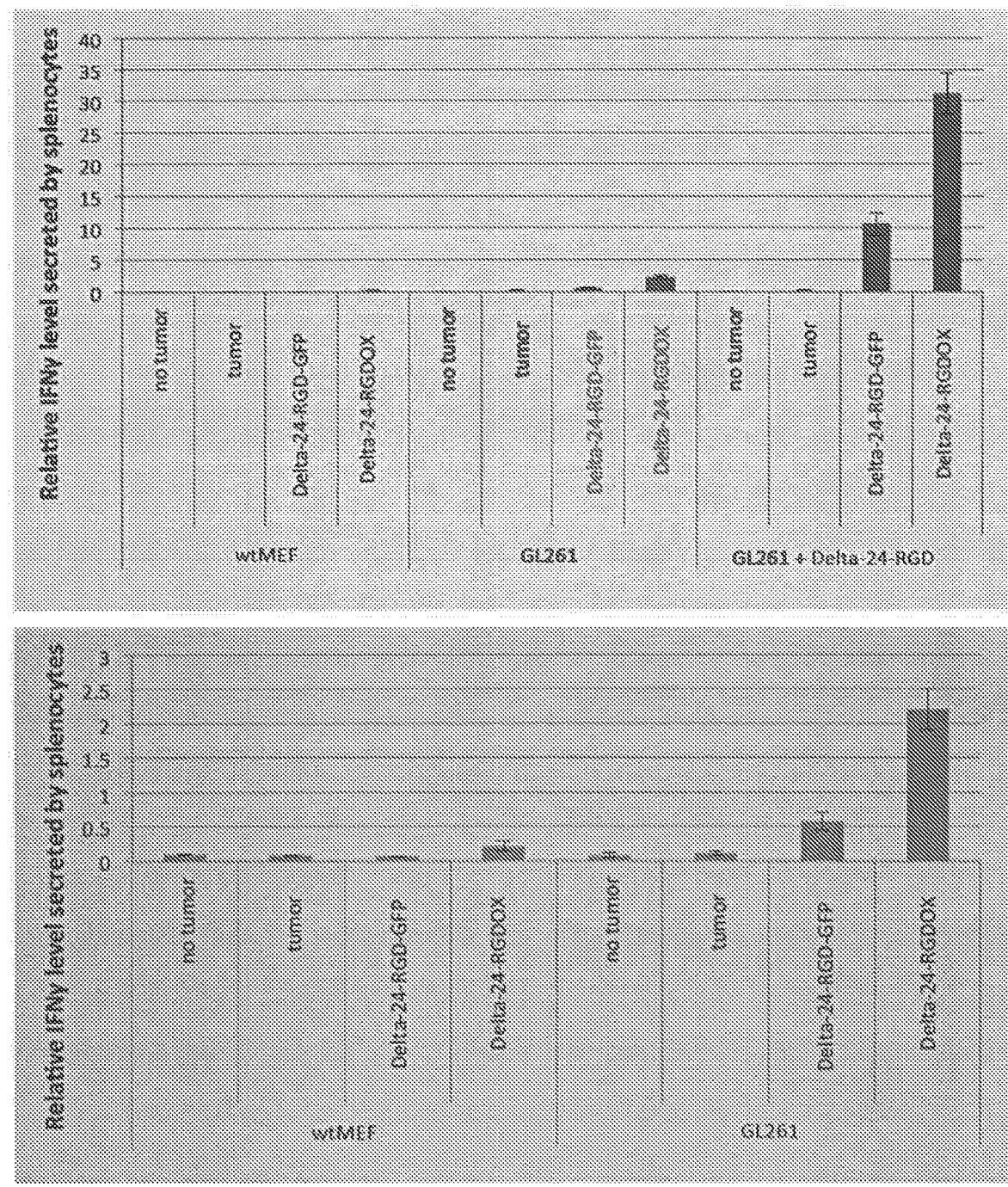
FIG. 11. Graph showing enhanced TH1 response in a mouse glioma model following treatment with Delta-24-RGD-OX40L (referred to as Delta-24-REDOX in the figure) . GL261 cells were implanted into the brain of C57BL/6 mice. Mice were treated with intratumoral injections of Delta-24-GFP or Delta-24-RGD-OX401, (days 7, 9, 11 after tumor cell implantation), At day 14, mouse splenocytes were harvested from 3-5 mice per group and incubated with wild type mouse embryonic fibroblasts (wtMEF), GL261 or Delta-24-RGD-infected GL261 cells for 40 hours. The concentration of IFNγ secreted by splenocytes, as an indicator of splenocyte activation, was measured by ELISA. The bottom panel shows similar results depicted in the top panel for the first two groups of the experiment, using a different scale range. This data demonstrates that treatment with Delta-24-RGD-OX40L enhances the TH1 immune response to the tumor in the mouse model. Moreover, this data demonstrates that in addition to initiating anti-adenovirus immunity, glioma-bearing mice treated with Delta-24-RGD_OX40L develop a specific cellular response against infected and uninfected tumor cells. Thus, infection by Delta-24-REDOX led to the development of anti-tumor immune response against cancer cells even if they had not been infected and suggests that by infecting a minority of tumor cells, Delta-24-REDOX will elicit an immune response potentially capable of the eradication of the tumor.
Figure 15:
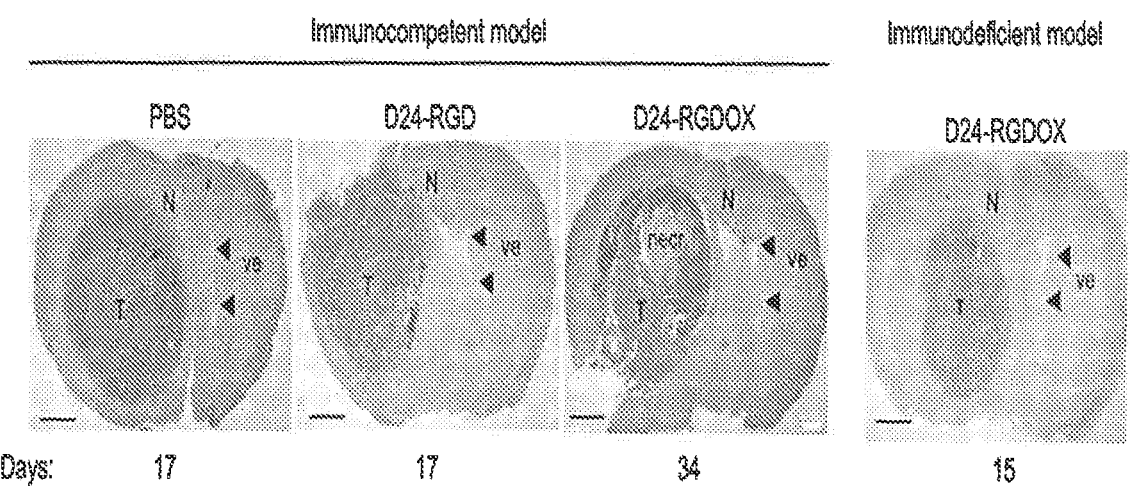
FIG. 15. Delta-24-RC DOX-induced necrosis (necr.) in the gliomas from C57BL/6 mice. Shown are representative hematoxylin and eosin-stained, whole-mount coronal sections of the brains from at least 6 mice from each group in FIGS. 7A-B. The numbers at the bottom indicate how many days after tumor implantation the mice were sacrificed. T: tumor; N: normal tissue; ye: lateral ventricle (arrowheads). Scale: 1 mm.

Consistent with these results, histopathologic studies of the mouse brains revealed that Delta-24-RGDOX induced tumor necrosis in C57BL/6 mice, which was not observed in either C57BL/6 mice treated with Delta-24-RGD or athymic mice treated with Delta-24-RGDOX (FIG. 7G), indicating the necrosis was induced by anti-tumor immunity but not by oncolysis. Moreover, the morphology and histology of the brains of the Delta-24-RGDOX-treated mice showed no signs of acute or chronic inflammation in the normal brain tissue (FIG. 7G and FIG. 15). These data are consistent with the observations of the tumor-specific immunity induced by Delta-24-RGDOX (FIG. 9C).

Because Delta-24-RGDOX only induced 20% long-term survival in the GL261-C57BL/6 model, its therapeutic efficacy may have been compromised by the rapid growth of the tumor. Accordingly, Delta-24-RGDOX demonstrated much greater therapeutic efficacy in the slow-growing GL261-5 glioma model than Delta-24-RGD (median survival: undefined vs. 50-52 days) resulting in a 70% long-term survival rate (FIG. 7D).

Figure 7E:
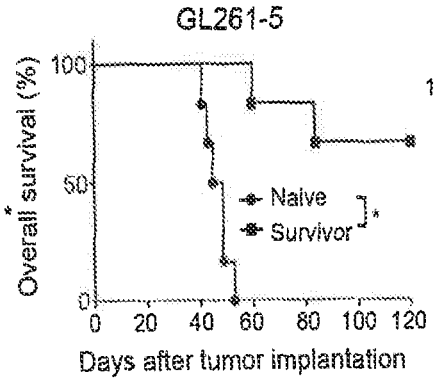
Figure 7F:
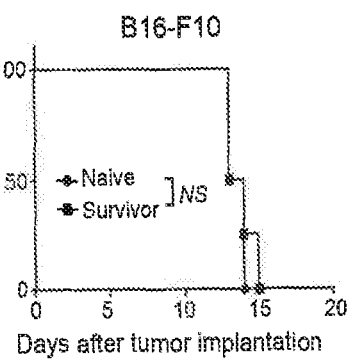
Figure 7G:
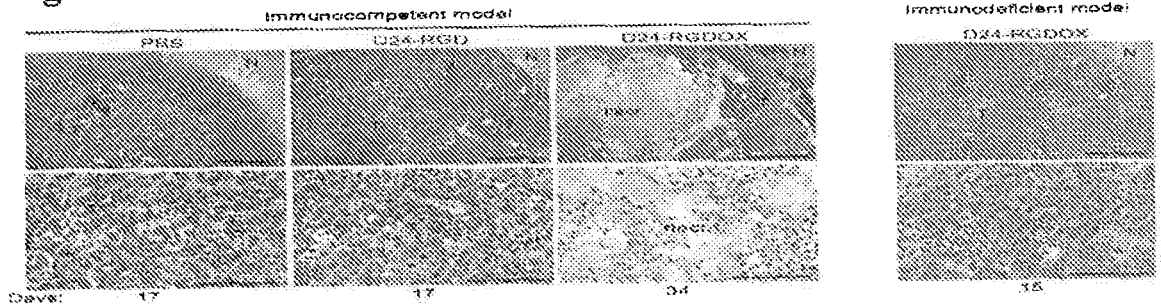

Re-challenging survivors of Delta-24-RGDOX-treated mice with GL-261-5 cells failed to produce gliomas in 4 of 6 animals, whereas all nave mice showed signs of intracranial disease and died of gliomas (median survivals: undefined vs. 47 days, FIG. 7E). These results suggest that Delta-24-RGDOX effectively induces specific immune memory against the same type of tumor that has been treated with the virus, which is potentiated by the virus-mediated OX40L expression.

The present inventors, for the first time, have combined oncolytic adenovirus D24-RGD with targeting the late costimulatory OX40L/OX40 pathway to treat gliomas in an immunocompetent syngeneic mouse model. Direct evidence is provided that expression of OX40L by replicative oncolytic adenovirus enhances the antigen-presenting function of the tumor cells, producing both increased immunity against tumor associated antigens and a specific immune response against tumor cells but not normal cells. Intratumoral injection of D24-RGDOX caused infiltration of innate and adaptive immune cells, instigating a Th1 immunity at the tumor site which resulted in specific anti-glioma immunity, shrunked tumor and prolonged survival. Importantly, D24-RGDOX displayed superior capability to elicit anti-glioma immunity than its parental virus D24-RGD. Splenocytes from mice treated with D24-RGDOX were stimulated against infected and non-infected GL261 cells to a significantly greater degree than splenocytes of mice treated with the combination of Delta-24-RGD and OX40 antibodies. Treatment with Delta-24-RGDOX did not prolong the life of immunosuppressed mice bearing intracranial GL261 tumors, demonstrating that the survival effect is mainly due to the anti-glioma immunity triggered by the virus. Moreover, more than 110 days after Delta-24-RGDOX treatment, a majority of the surviving mice were resistant to rechallenge of the tumor, suggesting the virus induces immune memory against the tumor since OX40 co-stimulatory signals potentiate the memory commitment of effector T cells. Due to the cancer selective nature of D24-RGD, OX40L should be expressed preferentially on cancer cells. Moreover, unlike ligands for CD28 which also bind CTLA4, OX40 ligand selectively binds OX40. Thus, OX40L stimulates OX40 on T lymphocytes with TCR recognizing tumor-associated viral antigens, resulting in the expansion of tumor-specific T cell populations. Accordingly, different from OX40 agonist antibody, the antagonist antibodies for CTLA-4 and PD-1 or using oncolytic viruses to express immune modulators to globally activate immune cells, the modulation of T cells by OX40L expressed by D24-.REDOX is more limited to tumor-specific T cells. Therefore, D24-REDOX is less likely to cause systemic toxicity related to those therapies. Based on the present exemplifications, it is expected that the percentage of human cancer patients with a complete response will be significantly increased with D24-RGDOX. The duration of the clinical response is also expected to increase with D24-REDOX due to the enhanced immune memory stimulated by OX40L/OX40 pathway.

This is in contrast to cancer vaccine strategies which have failed to ensure that tumor-specific T cells could home to tumors and/or exert their function within the tumor because of the immunosuppressive environment within the tumor. In contrast to just presenting antigens through professional antigen-presenting cells in cancer vaccine therapies, the effect of Delta-24-REDOX is multiplex. The infection of cancer cells by the virus releases PAMPs and DAMPS to induce innate immune response within the tumor, changing the tumor microenvironment from immunosuppressive to immune active, and enlarging the pool of tumor-specific T cells from the naïve repertoire and reactivating existing tumor-specific T cells that may be in a dormant or anergic state. Before the TAAs from the debris of the cancer cells lysed by the virus are presented through professional antigen-presenting cells, the OX40L expression and IFNγ-mediated expression of MHCs on the tumor cells induced by the virus enhance the role of cancer cells as ad hoc antigen-presenting cells. Moreover, since the vaccine strategy only covers a part of the cancer antigen repertoire, after immune editing during the therapy, cancer cells with different antigens can escape and give rise to new tumor cell populations that are resistant to the vaccine therapy. In contrast, Delta-24-RGDOX is designed to infect the whole cancer cell population and can mediate the presentation of the entire cancer antigen repertoire to the immune system during the therapy. This enables the virus to overcome the resistance of cancers due to the heterogeneity and therapy-induced evolution of the tumor cells, which are the main challenges in developing targeted cancer therapies.

Example 3

Synergism of D24-RGDOX with an Immune Checkpoint Inhibitor

Figure 12A:
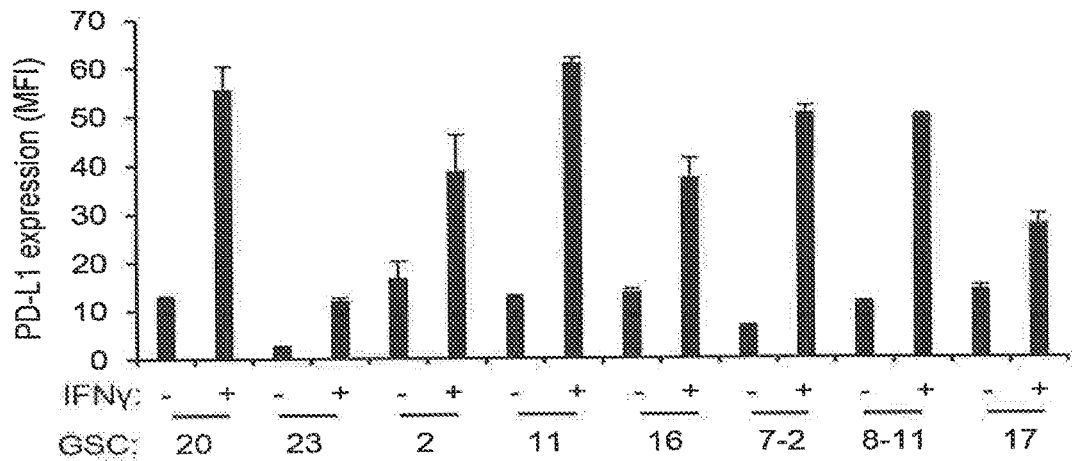
FIGS. 12A-E. Therapeutic effect of combining Delta-24-REDOX and anti-PD-L1 antibody.
Figure 12B:
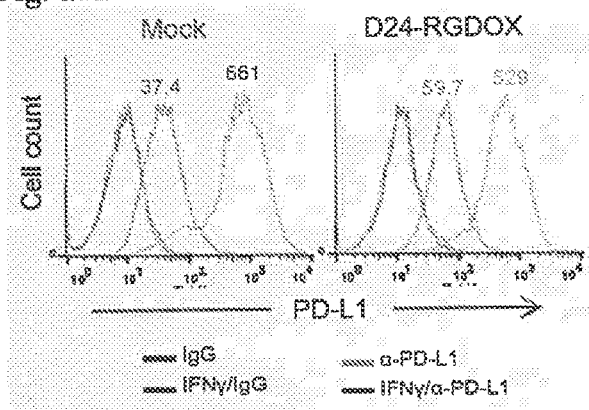
Figure 12C:
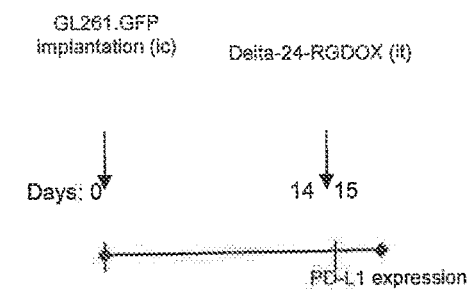
Figure 12D:
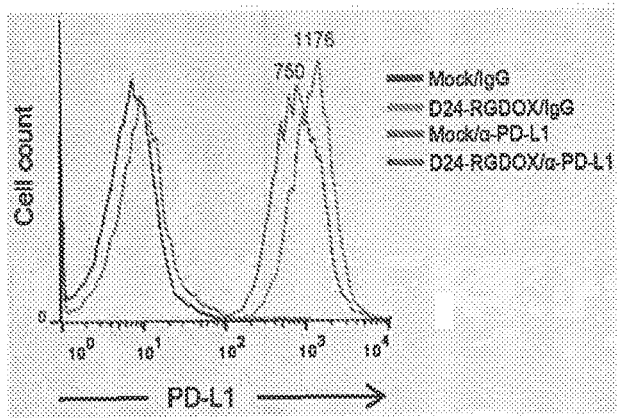
Figure 12E:
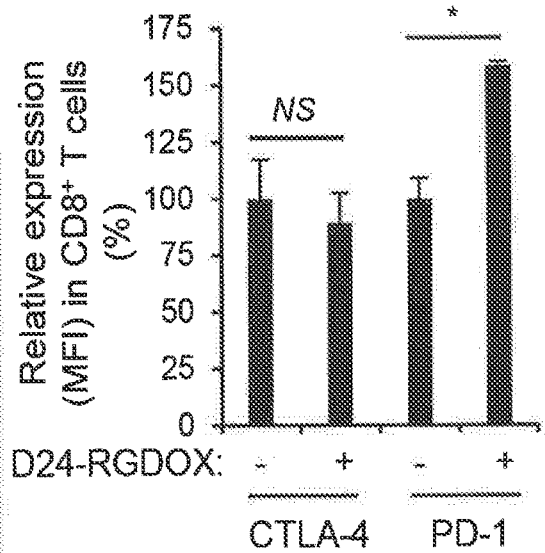
Figure 16:
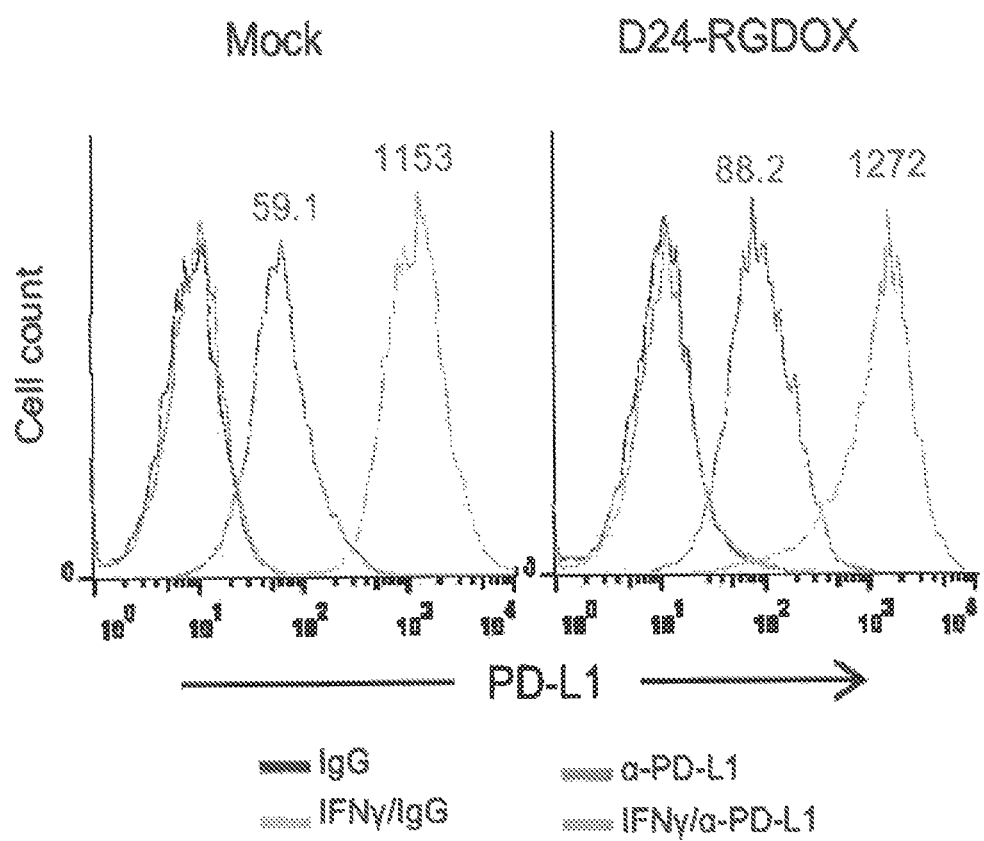
FIG. 16. PD-L1 expression in mouse glioma GL261-EGFP cells. Cells were mock-infected or infected with D24-RGDOX (100 pfu/cell) in the presence and absence of mouse IFNγ (100 U/ml) for 48 hours and then analyzed with flow cytometry for PD-L1 expression. The colored numbers indicate the MFI for the curve of the same color: "Mock": 59.1=α-PD-L1; 1153=IFNγ/αt-PD-L1; "D24-RGDOX": 88.2==α-PD-L1; 1272=IFNγ/α-PD-L1.

PD-L1 expression was examined in 8 human glioma stem cell (GCS) lines. In all cases, these cells expressed relatively low levels of PD-L1 that were dramatically increased with IFN-γ stimulation (FIG. 12A, P<0.002). Similarly, mouse glioma GL261-5 cells also expressed a low level of PD-L1 (median fluorescence intensity [MFI]=37.4) which was slightly enhanced by infection with Delta-24-RGDOX (MFI=59.7, FIG. 12B). However, IFNγ dramatically increased PD-L1 expression in GL261-5 cells both with (MFI=529) and without (MFI=661) Delta-24-RGDOX infection (FIG. 12B). Basal PD-L1 expression levels were slightly high in GL261-EGFP cells and also increased in response to IFNγ treatment (FIG. 16). Moreover, Delta-24-RGDOX injection in the gliomas derived from GL261-EGFP cells further upregulated PD-L1 levels in the tumor cells that was already higher than in the cultured cells (MFI increased from 750 to 1176, FIG. 12D). Furthermore, after Delta-24-RGDOX treatment, the expression of PD-1 on tumor-infiltrating CD8+ T cells increased by 58%, whereas the expression of another immune checkpoint inhibitor, CTLA-4, remained unchanged (FIG. 12E). These results suggest that the virotherapy results in a feedback activation of PD-L1/PD-1 pathway to compromise the anti-tumor immunity induced by the virus.

Figure 13A:
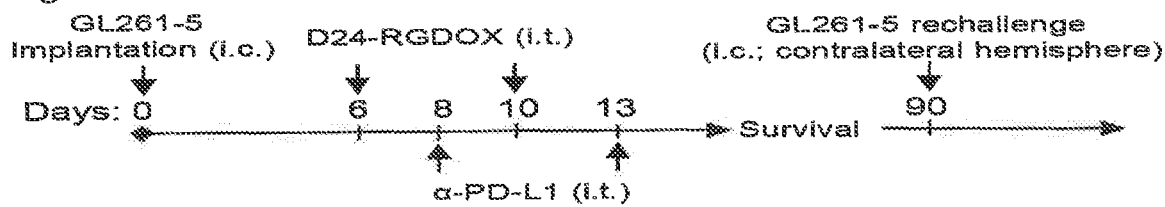
FIGS. 13A-D. Therapeutic effect of combining Delta-24-RGDOX and anti-PD-L1 antibody
Figure 13B:
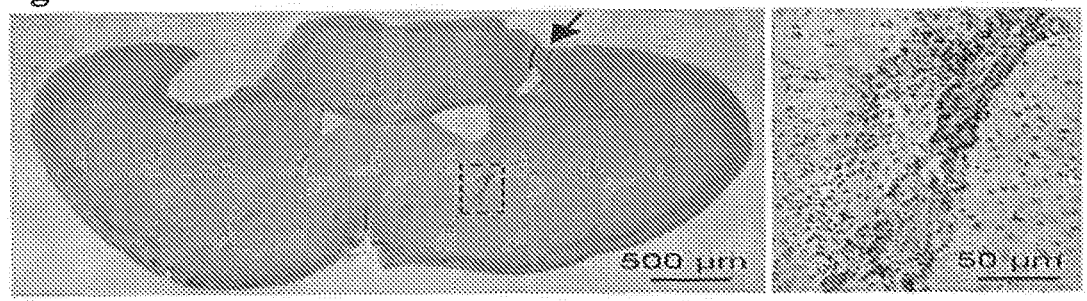
Figure 13C:
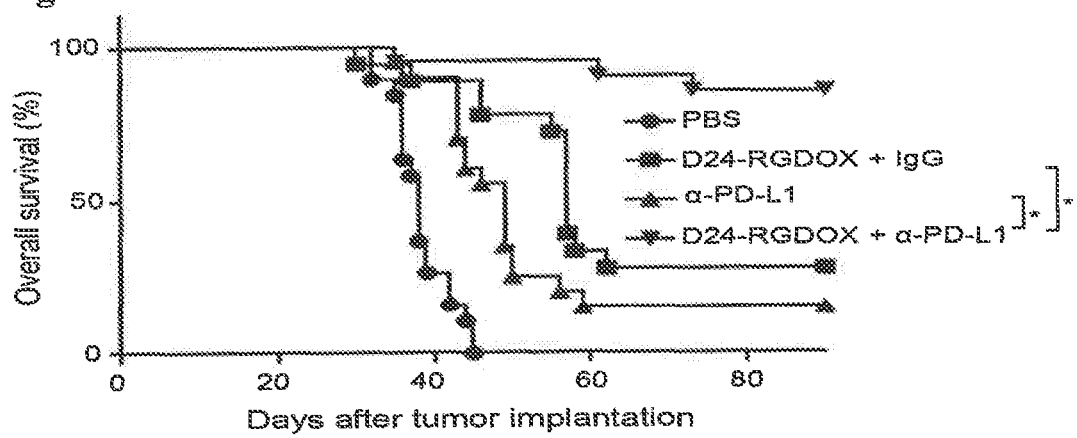

To further potentiate efficacy, Delta-24-RGDOX was combined with an anti-PD-L1 antibody to treat the gliomas derived from GL261-5 cells in C57BL/6 mice. The antibody was intratumorally injected to confine its effect mainly in the tumor, 2 days after the first viral dose and 3 days after the second to diminish the potential adverse effects of the antibody on the virus (FIG. 13A). The combination resulted in a long-term survival rate of 85%, whereas 2 injections of the virus alone extended the median survival time by 19 days, which corresponded to a long-term survival rate of only 28% (median survival: undefined vs, 57 days); the antibody alone extended the median survival time by 11 days, which corresponded to a long-term survival rate of only 15% (median survival: undefined vs. 49 days). These results demonstrated that these two agents synergized to reject the tumor (FIG. 13C).

Figure 13D:
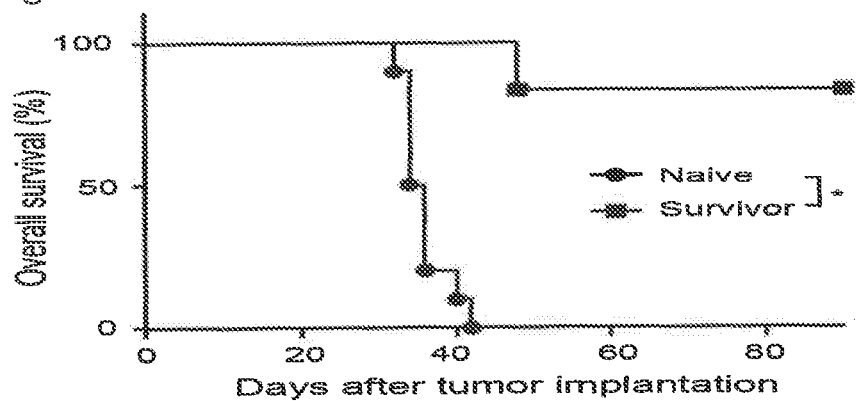

In the long-term surviving mice treated with the combination, tumor remnant was found in the brains at the tumor implantation site (FIG. 13B), suggesting that the treatment induced complete regression. Moreover, five of the six surviving mice in the combination treatment group also survived a re-challenge with the same tumor cells in the contralateral hemisphere, whereas all nave mice died of gliomas (median survival: undefined vs. 35 days, FIG. 13D). These findings suggest that the combination treatment induced the development of an immune memory that prevented growth at a distant site.

The combination of Delta-24-REDOX with anti-PD-L1 antibody synergistically increased antitumor efficacy and promotes the development of a systemic immune memory that can attack cancer cells in a distant location, resulting in 100% long-term survival rate in the treated glioma-bearing mice. This is particularly important in gliobastoma where post-surgical resection and temozolomide therapy, recurrence at distant sites is common, if not inevitable. Although these therapies were delivered locally to the tumor, their antitumor effect was not limited to the treated tumor site. The surviving mice that received the combination treatment were resistant to tumor cells implanted in the other hemisphere of the brain, suggesting that tumor-specific memory T cells can migrate to the new tumor site and attack the cancer cells there. Combination treatment with replicative oncolytic adenovirus and an inhibitor of an immune checkpoint protein such as PD-L1 achieved exceptional, cancer specific efficacy. Because human adenoviruses replicate less efficiently in mouse cells, fewer virions are available for subsequent re-infection in mice and immunity against viral antigens present on tumor cells in mice is weaker, the surprising efficacy of the combination therapy is expected to be even more potent in human patients than in the mouse models.

inhibitor inhibits a checkpoint protein selected from the group consisting of PD-L1, programmed cell death protein 1 (PD-1), and PD-L2.

2. The replication competent oncolytic adenovirus of claim 1, wherein the OX40 agonist is an OX40 ligand polypeptide.

3. The method of claim 1, wherein the sequence permitting expression of the OX40 agonist is a CMV or RSV promoter.

4. The method of claim 1, wherein the adenovirus genome further comprises a heterologous nucleic acid sequence encoding a tumor antigen.

5. The method of claim 1, wherein the replication competent oncolytic adenovirus and the checkpoint inhibitor are administered simultaneously.

6. The method of claim 1, wherein the replication competent oncolytic adenovirus and the checkpoint inhibitor are administered sequentially and wherein a first administration of oncolytic adenovirus occurs prior to a first administration of checkpoint inhibitor and preferably occurs within 30 days of a first administration of checkpoint inhibitor.

7. The method of claim 1, wherein the checkpoint inhibitor is an antibody or fusion protein and is administered as one or more doses of 0.01-10 mg/kg, 0.1-10 mg/kg, 1-10 mg/kg, 2-8 mg/kg, 3-7 mg/kg, 4-5 mg/kg or at least 10 mg/kg.

8. The method of claim 1, wherein the adenovirus is administered intratumorally, intravascularly, intratumorally and intravascularly or in a neuronal or mesenchymal stem cell carrier.

The invention claimed is:

1. A method for treating and/or preventing a glioma in a mammal in need thereof, comprising administering to the mammal an effective amount of a combination comprising (a) a Delta24-RGD nucleic acid backbone, and a heterologous nucleic acid sequence encoding an OX40 agonist inserted in a nonessential region of the adenovirus genome, wherein the inserted heterologous nucleic acid sequence is under the control of a sequence permitting expression of the OX40 agonist and (b) one or more immune checkpoint inhibitors, wherein said one or more immune checkpoint 9. The method of claim 1, wherein the adenovirus is administered once or multiple times at a dose of $10^8$-$10^{14}$ plaque forming units (pfu).

10. The method of claim 1, wherein the mammal is a human.

11. The method of claim 10, wherein the human has failed one or more treatments with an immune checkpoint inhibitor.

12. A method for treating and/or preventing cancer and/or treating and/or preventing a metastasis in a human subject in need thereof, comprising administering to the subject an effective amount of a replication competent oncolytic adenovirus according to claim 1, wherein the immune checkpoint inhibitor and optionally the immune cell co-stimulatory receptor agonist is expressed in a cancer cell of the subject.

13. The method according to claim 1 wherein said wherein said one or more immune checkpoint inhibitor inhibits PD-1.

14. The method according to claim 13, wherein said inhibitor of PD-1 is selected from the group consisting of Nivolumab, Pembrolizumab, and Pidilizumab.

\* \* \* \* \*